(12) United States Patent
Blakely et al.

(10) Patent No.: US 7,338,799 B2
(45) Date of Patent: Mar. 4, 2008

(54) POLYNUCLEOTIDE ENCODING A MOUSE CHOLINE TRANSPORTER

(75) Inventors: Randy D. Blakely, Brentwood, TN (US); Subramaniam Apparsundaram, Lexington, KY (US); Shawn Ferguson, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 554 days.

(21) Appl. No.: 10/724,806

(22) Filed: Dec. 1, 2003

(65) Prior Publication Data

US 2004/0248838 A1 Dec. 9, 2004

Related U.S. Application Data

(62) Division of application No. 09/911,077, filed on Jul. 23, 2001, now abandoned.

(51) Int. Cl.
- C07H 21/04 (2006.01)
- C12N 5/00 (2006.01)
- C12N 15/00 (2006.01)
- C12N 7/01 (2006.01)
- C07K 14/47 (2006.01)

(52) U.S. Cl. ............. 435/325; 435/235.1; 435/252.3; 435/320.1; 536/23.5; 530/350

(58) Field of Classification Search ............... None
See application file for complete search history.

(56) References Cited

U.S. PATENT DOCUMENTS

| 5,658,786 A | 8/1997 | Smith et al. ............... 435/365 |
| 6,500,643 B1 | 12/2002 | Wu et al. ................... 435/69.1 |

FOREIGN PATENT DOCUMENTS

| CA | 2382464 A1 * | 2/2002 |
| DE | 10009055 | 8/2001 |
| WO | WO-0116315 A1 * | 3/2001 |

OTHER PUBLICATIONS

Kaufman et al. Blood 94: 3178-3184, 1999.*
Wang et al. Rapid analysis of gene expression (RAGE) facilitates universal expression profiling. Nucleic Acids Res 27(23): 4609-4618, 1999.*
Invitrogen 2001 catalog, p. 155.*
Ferguson et al. Lethal impairment of cholinergic neurotransmission in hemicholinium-3-sensitive choline transporter knockout mice. Proc Natl Acad Sci U S A. 101(23):8762-8767, 2004.*
Apparsundaram et al., "Immunocytochemical localization of hemicholinium-3-sensitive choline transporters," *Soc. For Neuroscience*, ABSTRACT,Nov. 10-15, 2001, San Diego.
Apparsundaram et al., "Molecular cloning and characterization of human and murine high-affinity choline transporters," *Soc. Neurosci.*, ABSTRACT, 26:15350, 2000. Abstract found at the Society for Neuroscience website. www.nfs.org, Dec. 26, 2001.

Apparsundaram et al., "Molecular cloning and characterization of a murine, hemicholinium-3-sensitive choline transporter," *Biochemical Society Transactions*, 29(6):711-716, 2001.
Apparsundaram et al., "Molecular cloning of a human, hemicholinium-3-sensitive choline transporter," *Biochem. Biophys. Res. Communications*, 276:862-867, 2000.
Barnwell et al., "Cloning and sequencing of a cDNA encoding a novel member of the human brain GABA/noradrenaline neurotransmitter transporter family," *Gene*, 159:287-288, 1995.
Bork et al., "Go hunting in sequence databases but watch out for the traps," *Trends in Genetics*, 12(10):425-427, 1996.
Bork, "Powers and pitfalls in sequence analysis: the 70% hurdle," *Genome Res.*, 10:398-400, 2000.
Brenner, "Errors in genome function," *Trends in Genetics*, 15(4):132-133, 1999.
Dai et al., "Cloning and characterization of the thyroid iodide transporter," *Nature*, 379:458-459, 1996.
Doerks et al., "Protein annotation: detective work for function prediction," *Trends in Genetics*, 14(6):248-250, 1998.
Ferguson et al., "Regulated subcellular localization of high-affinity choline transporters (CHTs) supported by protein phosphatase 2A interactions," *Soc. For Neuroscience*, ABSTRACT, Nov. 10-15, 2001, San Diego.
Fisher et al., "Transport of choline by plasma membrane vesicles from lung-derived epithelial cells," *Am. J. Physiol.*, 263(6 pt 1):C1250-1257, 1992.
GenBank Accession No. AB030947, Okuda et al., Feb. 2000.
GenBank Accession No. AB043997, Okuda et al., Nov. 2000.
GenBank Accession No. AC009933, Heath, Jul. 2001.
GenBank Accession No. AC009963, Waterston, Aug. 2001.
GenBank Accession No. AC023672, Waterston, Nov. 2001.
GenBank Accession No. AF276871, Apparsundaram et al., Nov. 2000.
GenBank Accession No. AF276872, Apparsundaram et al., Feb. 2001.
GenBank Accession No. AJ401466, Wieland et al., Aug. 2000.
GenBank Accession No. Z17178, Weissenbach, Nov. 1994.
GenBank Accession No. Z23978, Weissenbach, Nov. 1994.
GenBank Accession No. Z53730, Weissenbach, Mar. 1996.
Guimbal and Kilimann, "A $Na^+$-dependent creatine transporter in rabbit brain, muscle, heart, and kidney," *J Biol Chem*, 268(12):8418-8421, 1993.

(Continued)

*Primary Examiner*—Bridget E. Bunner
(74) *Attorney, Agent, or Firm*—Fulbright & Jaworski

(57) ABSTRACT

Human high affinity choline transporter (CHT) cDNA was cloned from spinal cord and the primary structure and chromosomal localization have been determined. Mouse high affinity CHT cDNA was also cloned and characterized. An isolated polynucleotide, an isolated polypeptide, a recombinant host cell, a recombinant vector, a purified protein, an antibody, a nucleic acid detection kit, a method for screening cholinergic therapeutics, a method of treating a patient, a method of gene therapy and transgenic CHT mice are discussed.

7 Claims, 17 Drawing Sheets

OTHER PUBLICATIONS

Hediger et al., "Expression cloning and cDNA sequencing of the Na+/glucose co-transporter," *Nature*, 330:379-381, 1987.

Lockman et al., "The transport of choline," *Drug Develop. Indust. Pharm.*, 28(7):749-771, 2002.

Mayser et al., "Primary structure and functional expression of a choline transporter expressed in the rat nervous system," *FEBS*, 305(1):31-36, 1992.

Ngo et al., "Computational complexity, protein structure prediction, and the Levinthal paradox," *The Protein Folding Problem and Tertiary Structure Prediction*, 492-495, 1994.

Nikawa et al., "Primary structure of the yeast choline transport gene and regulation of its expression," *J. Biol. Chem.*, 265(26):15996-16003, 1990.

O'Regan et al., "An electric lobe suppressor for a yeast choline transport mutation belongs to a new family of transporter-like proteins," *PNAS*, 97(4):1835-1840, 2000.

Okuda and Haga, "Functional characterization of the human high-affinity choline transporter," *FEBS Letters*, 484:92-97, 2000.

Okuda et al., "Identification and characterization of the high-affinity choline transporter," *Nature Neuroscience*, 3(2):120-125, 2000.

Okuda et al., "Single nucleotide polymorphism of the human high affinity choline transporter alters transport rate," *J. Biol. Chem.*, 277(47):45315-43522, 2002.

Phillips, "The challenge of gene therapy and DNA delivery," *Pharm. Pharmacol.*, 53:1169-1174, 2001.

Schloss et al., "The putative rat choline transporter CHOT1 transports creatine and is highly expressed in neural and muscle-rich tissues," *Biochem Biophys Res Commun*, 198(2):637-645, 1994.

Skolnick et al., "From genes to protein structure and function: novel applications of computational approaches in the genomic era," *Trends in Biotech.*, 18(1):34-39, 2000.

Smith et al., "The challenges of genome sequence annotation or 'The devil is in the details,'" *Nature Biotech.*, 15:1222-1223, 1997.

Turk and Wright, "Membrane topology motifs in the SGLT cotransporter family," *J Membr Biol*, 159:1-20, 1997.

Wells, "Additivity of mutational effects in proteins," *Biochemistry*, 2(37):8509-8517, 1990.

Zoli et al., "Increased neurodegeneration during ageing in mice lacking high-affinity nicotine receptors," *EMBO Journal*, 18(5):1235-1244, 1999.

* cited by examiner

SEQUENCE LISTING

```
<160> NUMBER OF SEQ ID NOS: 29

<210> SEQ ID NO 1
<211> LENGTH: 1743
<212> TYPE: DNA
<213> ORGANISM: Homo sapiens
<220> FEATURE:
<221> NAME/KEY: CDS
<222> LOCATION: (1)..(1743)

<400> SEQUENCE: 1 atg gct ttc cat gtg gaa gga ctg ata gct atc atc gtg ttc tac ctt        48
Met Ala Phe His Val Glu Gly Leu Ile Ala Ile Ile Val Phe Tyr Leu
 1               5                  10                  15 cta att ttg ctg gtt gga ata tgg gct gcc tgg aga acc aaa aac agt        96
Leu Ile Leu Leu Val Gly Ile Trp Ala Ala Trp Arg Thr Lys Asn Ser
             20                  25                  30 ggc agc gca gaa gag cgc agc gaa gcc atc ata gtt ggt ggc cga gat       144
Gly Ser Ala Glu Glu Arg Ser Glu Ala Ile Ile Val Gly Gly Arg Asp
         35                  40                  45 att ggt tta ttg gtt ggt gga ttt acc atg aca gct acc tgg gtc gga       192
Ile Gly Leu Leu Val Gly Gly Phe Thr Met Thr Ala Thr Trp Val Gly
     50                  55                  60 gga ggg tat atc aat ggc aca gct gaa gca gtt tat gta cca ggt tat       240
Gly Gly Tyr Ile Asn Gly Thr Ala Glu Ala Val Tyr Val Pro Gly Tyr
 65                  70                  75                  80 ggc cta gct tgg gct cag gca cca att gga tat tct ctt agt ctg att       288
Gly Leu Ala Trp Ala Gln Ala Pro Ile Gly Tyr Ser Leu Ser Leu Ile
                 85                  90                  95 tta ggt ggc ctg ttc ttt gca aaa cct atg cgt tca aag ggg tat gtg       336
Leu Gly Gly Leu Phe Phe Ala Lys Pro Met Arg Ser Lys Gly Tyr Val
            100                 105                 110 acc atg tta gac ccg ttt cag caa atc tat gga aaa cgc atg ggc gga       384
Thr Met Leu Asp Pro Phe Gln Gln Ile Tyr Gly Lys Arg Met Gly Gly
        115                 120                 125 ctc ctg ttt att cct gca ctg atg gga gaa atg ttc tgg gct gca gca       432
Leu Leu Phe Ile Pro Ala Leu Met Gly Glu Met Phe Trp Ala Ala Ala
    130                 135                 140 att ttc tct gct ttg gga gcc acc atc agc gtg atc atc gat gtg gat       480
Ile Phe Ser Ala Leu Gly Ala Thr Ile Ser Val Ile Ile Asp Val Asp
```

```
                    145                 150                 155                 160
atg cac att tct gtc atc atc tct gca ctc att gcc act ctg tac aca        528
Met His Ile Ser Val Ile Ile Ser Ala Leu Ile Ala Thr Leu Tyr Thr
                165                 170                 175 ctg gtg gga ggg ctc tat tct gtg gcc tac act gat gtc gtt cag ctc        576
Leu Val Gly Gly Leu Tyr Ser Val Ala Tyr Thr Asp Val Val Gln Leu
            180                 185                 190 ttt tgc att ttt gta ggg ctg tgg atc agc gtc ccc ttt gca ttg tca        624
Phe Cys Ile Phe Val Gly Leu Trp Ile Ser Val Pro Phe Ala Leu Ser
        195                 200                 205 cat cct gca gtc gca gac atc ggg ttc act gct gtg cat gcc aaa tac        672
His Pro Ala Val Ala Asp Ile Gly Phe Thr Ala Val His Ala Lys Tyr
    210                 215                 220 caa aag ccg tgg ctg gga act gtt gac tca tct gaa gtc tac tct tgg        720
Gln Lys Pro Trp Leu Gly Thr Val Asp Ser Ser Glu Val Tyr Ser Trp
225                 230                 235                 240 ctt gat agt ttt ctg ttg ttg atg ctg ggt gga atc cca tgg caa gca        768
Leu Asp Ser Phe Leu Leu Leu Met Leu Gly Gly Ile Pro Trp Gln Ala
                245                 250                 255 tac ttt cag agg gtt ctc tct tct tcc tca gcc acc tat gct caa gtg        816
Tyr Phe Gln Arg Val Leu Ser Ser Ser Ser Ala Thr Tyr Ala Gln Val
            260                 265                 270 ctg tcc ttc ctg gca gct ttc ggg tgc ctg gtg atg gcc atc cca gcc        864
Leu Ser Phe Leu Ala Ala Phe Gly Cys Leu Val Met Ala Ile Pro Ala
        275                 280                 285 ata ctc att ggg gcc att gga gca tca aca gac tgg aac cag act gca        912
Ile Leu Ile Gly Ala Ile Gly Ala Ser Thr Asp Trp Asn Gln Thr Ala
    290                 295                 300 tat ggg ctt cca gat ccc aag act aca gaa gag gca gac atg att tta        960
Tyr Gly Leu Pro Asp Pro Lys Thr Thr Glu Glu Ala Asp Met Ile Leu
305                 310                 315                 320 cca att gtt ctg cag tat ctc tgc cct gtg tat att tct ttc ttt ggt       1008
Pro Ile Val Leu Gln Tyr Leu Cys Pro Val Tyr Ile Ser Phe Phe Gly
                325                 330                 335 ctt ggt gca gtt tct gct gct gtt atg tca tca gca gat tct tcc atc       1056
Leu Gly Ala Val Ser Ala Ala Val Met Ser Ser Ala Asp Ser Ser Ile
            340                 345                 350 ttg tca gca agt tcc atg ttt gca cgg aac atc tac cag ctt tcc ttc       1104
Leu Ser Ala Ser Ser Met Phe Ala Arg Asn Ile Tyr Gln Leu Ser Phe
        355                 360                 365 aga caa aat gct tcg gac aaa gaa atc gtt tgg gtt atg cga atc aca       1152
Arg Gln Asn Ala Ser Asp Lys Glu Ile Val Trp Val Met Arg Ile Thr
    370                 375                 380 gtg ttt gtg ttt gga gca tct gca aca gcc atg gcc ttg ctg acg aaa       1200
Val Phe Val Phe Gly Ala Ser Ala Thr Ala Met Ala Leu Leu Thr Lys
385                 390                 395                 400 act gtg tat ggg ctc tgg tac ctc agt tct gac ctt gtt tac atc gtt       1248
Thr Val Tyr Gly Leu Trp Tyr Leu Ser Ser Asp Leu Val Tyr Ile Val
                405                 410                 415 atc ttc ccc cag ctg ctt tgt gta ctc ttt gtt aag gga acc aac acc       1296
Ile Phe Pro Gln Leu Leu Cys Val Leu Phe Val Lys Gly Thr Asn Thr
            420                 425                 430 tat ggg gcc gtg gca ggt tat gtt tct ggc ctc ttc ctg aga ata act       1344
Tyr Gly Ala Val Ala Gly Tyr Val Ser Gly Leu Phe Leu Arg Ile Thr
        435                 440                 445 gga ggg gag cca tat ctg tat ctt cag ccc ttg atc ttc tac cct ggc       1392
Gly Gly Glu Pro Tyr Leu Tyr Leu Gln Pro Leu Ile Phe Tyr Pro Gly
    450                 455                 460 tat tac cct gat gat aat ggt ata tat aat cag aaa ttt cca ttt aaa       1440
```

```
Tyr Tyr Pro Asp Asp Asn Gly Ile Tyr Asn Gln Lys Phe Pro Phe Lys
465                 470                 475                 480 aca ctt gcc atg gtt aca tca ttc tta acc aac att tgc atc tcc tat      1488
Thr Leu Ala Met Val Thr Ser Phe Leu Thr Asn Ile Cys Ile Ser Tyr
                485                 490                 495 cta gcc aag tat cta ttt gaa agt gga acc ttg cca cct aaa tta gat      1536
Leu Ala Lys Tyr Leu Phe Glu Ser Gly Thr Leu Pro Pro Lys Leu Asp
        500                 505                 510 gta ttt gat gct gtt gtt gca aga cac agt gaa gaa aac atg gat aag      1584
Val Phe Asp Ala Val Val Ala Arg His Ser Glu Glu Asn Met Asp Lys
    515                 520                 525 aca att ctt gtc aaa aat gaa aat att aaa tta gat gaa ctt gca ctt      1632
Thr Ile Leu Val Lys Asn Glu Asn Ile Lys Leu Asp Glu Leu Ala Leu
530                 535                 540 gtg aag cca cga cag agc atg acc ctc agc tca act ttc acc aat aaa      1680
Val Lys Pro Arg Gln Ser Met Thr Leu Ser Ser Thr Phe Thr Asn Lys
545                 550                 555                 560 gag gcc ttc ctt gat gtt gat tcc agt cca gaa ggg tct ggg act gaa      1728
Glu Ala Phe Leu Asp Val Asp Ser Ser Pro Glu Gly Ser Gly Thr Glu
                565                 570                 575 gat aat tta cag tga                                                  1743
Asp Asn Leu Gln
            580

<210> SEQ ID NO 2
<211> LENGTH: 580
<212> TYPE: PRT
<213> ORGANISM: Homo sapiens

<400> SEQUENCE: 2

Met Ala Phe His Val Glu Gly Leu Ile Ala Ile Ile Val Phe Tyr Leu
 1               5                  10                  15

Leu Ile Leu Leu Val Gly Ile Trp Ala Ala Trp Arg Thr Lys Asn Ser
             20                  25                  30

Gly Ser Ala Glu Glu Arg Ser Glu Ala Ile Ile Val Gly Gly Arg Asp
         35                  40                  45

Ile Gly Leu Leu Val Gly Gly Phe Thr Met Thr Ala Thr Trp Val Gly
     50                  55                  60

Gly Gly Tyr Ile Asn Gly Thr Ala Glu Ala Val Tyr Val Pro Gly Tyr
 65                  70                  75                  80

Gly Leu Ala Trp Ala Gln Ala Pro Ile Gly Tyr Ser Leu Ser Leu Ile
                 85                  90                  95

Leu Gly Gly Leu Phe Phe Ala Lys Pro Met Arg Ser Lys Gly Tyr Val
            100                 105                 110

Thr Met Leu Asp Pro Phe Gln Gln Ile Tyr Gly Lys Arg Met Gly Gly
        115                 120                 125

Leu Leu Phe Ile Pro Ala Leu Met Gly Glu Met Phe Trp Ala Ala Ala
    130                 135                 140

Ile Phe Ser Ala Leu Gly Ala Thr Ile Ser Val Ile Ile Asp Val Asp
145                 150                 155                 160

Met His Ile Ser Val Ile Ser Ala Leu Ile Ala Thr Leu Tyr Thr
                165                 170                 175

Leu Val Gly Gly Leu Tyr Ser Val Ala Tyr Thr Asp Val Gln Leu
            180                 185                 190

Phe Cys Ile Phe Val Gly Leu Trp Ile Ser Val Pro Phe Ala Leu Ser
        195                 200                 205

His Pro Ala Val Ala Asp Ile Gly Phe Thr Ala Val His Ala Lys Tyr
```

```
            210                 215                 220
Gln Lys Pro Trp Leu Gly Thr Val Asp Ser Ser Glu Val Tyr Ser Trp
225                 230                 235                 240

Leu Asp Ser Phe Leu Leu Leu Met Leu Gly Gly Ile Pro Trp Gln Ala
                245                 250                 255

Tyr Phe Gln Arg Val Leu Ser Ser Ser Ala Thr Tyr Ala Gln Val
            260                 265                 270

Leu Ser Phe Leu Ala Ala Phe Gly Cys Leu Val Met Ala Ile Pro Ala
            275                 280                 285

Ile Leu Ile Gly Ala Ile Gly Ala Ser Thr Asp Trp Asn Gln Thr Ala
290                 295                 300

Tyr Gly Leu Pro Asp Pro Lys Thr Thr Glu Glu Ala Asp Met Ile Leu
305                 310                 315                 320

Pro Ile Val Leu Gln Tyr Leu Cys Pro Val Tyr Ile Ser Phe Phe Gly
                325                 330                 335

Leu Gly Ala Val Ser Ala Ala Val Met Ser Ser Ala Asp Ser Ser Ile
                340                 345                 350

Leu Ser Ala Ser Ser Met Phe Ala Arg Asn Ile Tyr Gln Leu Ser Phe
            355                 360                 365

Arg Gln Asn Ala Ser Asp Lys Glu Ile Val Trp Val Met Arg Ile Thr
    370                 375                 380

Val Phe Val Phe Gly Ala Ser Ala Thr Ala Met Ala Leu Leu Thr Lys
385                 390                 395                 400

Thr Val Tyr Gly Leu Trp Tyr Leu Ser Ser Asp Leu Val Tyr Ile Val
                405                 410                 415

Ile Phe Pro Gln Leu Leu Cys Val Leu Phe Val Lys Gly Thr Asn Thr
                420                 425                 430

Tyr Gly Ala Val Ala Gly Tyr Val Ser Gly Leu Phe Leu Arg Ile Thr
            435                 440                 445

Gly Gly Glu Pro Tyr Leu Tyr Leu Gln Pro Leu Ile Phe Tyr Pro Gly
    450                 455                 460

Tyr Tyr Pro Asp Asp Asn Gly Ile Tyr Asn Gln Lys Phe Pro Phe Lys
465                 470                 475                 480

Thr Leu Ala Met Val Thr Ser Phe Leu Thr Asn Ile Cys Ile Ser Tyr
                485                 490                 495

Leu Ala Lys Tyr Leu Phe Glu Ser Gly Thr Leu Pro Pro Lys Leu Asp
            500                 505                 510

Val Phe Asp Ala Val Val Ala Arg His Ser Glu Asn Met Asp Lys
            515                 520                 525

Thr Ile Leu Val Lys Asn Glu Asn Ile Lys Leu Asp Glu Leu Ala Leu
    530                 535                 540

Val Lys Pro Arg Gln Ser Met Thr Leu Ser Ser Thr Phe Thr Asn Lys
545                 550                 555                 560

Glu Ala Phe Leu Asp Val Asp Ser Ser Pro Gly Ser Gly Thr Glu
                565                 570                 575

Asp Asn Leu Gln
            580

<210> SEQ ID NO 3
<211> LENGTH: 1743
<212> TYPE: DNA
<213> ORGANISM: Mus musculus
<220> FEATURE:
<221> NAME/KEY: CDS
<222> LOCATION: (1)..(1743)
```

<400> SEQUENCE: 3

```
atg cct ttc cat gtg gaa gga ctg gta gct att atc ctc ttc tac ctc      48
Met Pro Phe His Val Glu Gly Leu Val Ala Ile Ile Leu Phe Tyr Leu
  1               5                  10                  15 ctt ata ttt ctg gtt gga ata tgg gct gca tgg aaa acc aaa aac agc      96
Leu Ile Phe Leu Val Gly Ile Trp Ala Ala Trp Lys Thr Lys Asn Ser
             20                  25                  30 ggc aac cca gaa gag cgc agt gaa gcc atc ata gtc ggg ggc cgt gac     144
Gly Asn Pro Glu Glu Arg Ser Glu Ala Ile Ile Val Gly Gly Arg Asp
         35                  40                  45 att ggt ttg ttg gtt ggt ggt ttt acc atg aca gcc acc tgg gtt gga     192
Ile Gly Leu Leu Val Gly Gly Phe Thr Met Thr Ala Thr Trp Val Gly
     50                  55                  60 gga ggc tac atc aat ggg aca gca gaa gca gtg tat ggg cca ggt tgt     240
Gly Gly Tyr Ile Asn Gly Thr Ala Glu Ala Val Tyr Gly Pro Gly Cys
 65                  70                  75                  80 ggt cta gct tgg gct cat gca ccc att gga tat tct ctg agt cta att     288
Gly Leu Ala Trp Ala His Ala Pro Ile Gly Tyr Ser Leu Ser Leu Ile
                 85                  90                  95 tta ggt ggt ctg ttt ttt gcg aaa cct atg cgt tcc aag gga tat gtg     336
Leu Gly Gly Leu Phe Phe Ala Lys Pro Met Arg Ser Lys Gly Tyr Val
            100                 105                 110 act atg tta gac cca ttc aaa cag atc tat gga aag cgc atg ggt ggg     384
Thr Met Leu Asp Pro Phe Lys Gln Ile Tyr Gly Lys Arg Met Gly Gly
        115                 120                 125 ctg ctc ttc atc cct gca ctg atg gga gag atg ttc tgg gct gca gca     432
Leu Leu Phe Ile Pro Ala Leu Met Gly Glu Met Phe Trp Ala Ala Ala
    130                 135                 140 att ttc tct gca tta ggg gcc acc atc agc gtg atc att gat gtg gat     480
Ile Phe Ser Ala Leu Gly Ala Thr Ile Ser Val Ile Ile Asp Val Asp
145                 150                 155                 160 gtg aac ata tcg gtc att gtc tct gca ctc att gcc att ctt tat acc     528
Val Asn Ile Ser Val Ile Val Ser Ala Leu Ile Ala Ile Leu Tyr Thr
                165                 170                 175 cta gtg ggt ggg ctc tac tct gtg gca tat act gat gtt gtc cag cta     576
Leu Val Gly Gly Leu Tyr Ser Val Ala Tyr Thr Asp Val Val Gln Leu
            180                 185                 190 ttc tgc att ttt ata gga ctg tgg atc agt gtc cct ttt gcc ctg tca     624
Phe Cys Ile Phe Ile Gly Leu Trp Ile Ser Val Pro Phe Ala Leu Ser
        195                 200                 205 cat cct gca gtc acc gac atc gga ttc aca gct gtg cat gct aaa tac     672
His Pro Ala Val Thr Asp Ile Gly Phe Thr Ala Val His Ala Lys Tyr
    210                 215                 220 cag agt ccc tgg ctg gga acc att gaa tca gtt gaa gtc tac acc tgg     720
Gln Ser Pro Trp Leu Gly Thr Ile Glu Ser Val Glu Val Tyr Thr Trp
225                 230                 235                 240 ctt gat aat ttt ctg tta ttg atg ctg ggt gga atc cca tgg caa gcc     768
Leu Asp Asn Phe Leu Leu Leu Met Leu Gly Gly Ile Pro Trp Gln Ala
                245                 250                 255 tac ttc cag agg gtc ctc tct tca tcc tca gcc acc tat gct cag gta     816
Tyr Phe Gln Arg Val Leu Ser Ser Ser Ser Ala Thr Tyr Ala Gln Val
            260                 265                 270 ctg tcc ttc ctg gca gct ttt ggg tgc ctg gtg atg gct cta ccc gcc     864
Leu Ser Phe Leu Ala Ala Phe Gly Cys Leu Val Met Ala Leu Pro Ala
        275                 280                 285 ata tgc ata gga gct att gga gct tcc aca gac tgg aac cag act gcc     912
Ile Cys Ile Gly Ala Ile Gly Ala Ser Thr Asp Trp Asn Gln Thr Ala
    290                 295                 300
```

```
tac ggg tat cca gat ccc aag act aag gag gaa gca gac atg att ctc      960
Tyr Gly Tyr Pro Asp Pro Lys Thr Lys Glu Glu Ala Asp Met Ile Leu
305                 310                 315                 320 ccg atc gtt ctg cag tac ctc tgc cct gtg tac atc tcc ttc ttt ggg     1008
Pro Ile Val Leu Gln Tyr Leu Cys Pro Val Tyr Ile Ser Phe Phe Gly
                325                 330                 335 ctt ggt gct gtt tca gct gct gtc atg tcc tca gct gac tcg tcc atc     1056
Leu Gly Ala Val Ser Ala Ala Val Met Ser Ser Ala Asp Ser Ser Ile
            340                 345                 350 ctg tcg gcg agt tct atg ttt gct cgg aat atc tac cag ctt tcc ttc     1104
Leu Ser Ala Ser Ser Met Phe Ala Arg Asn Ile Tyr Gln Leu Ser Phe
        355                 360                 365 aga caa aat gca tca gac aag gaa att gtg tgg gtc atg agg atc act     1152
Arg Gln Asn Ala Ser Asp Lys Glu Ile Val Trp Val Met Arg Ile Thr
    370                 375                 380 gtg ctt gtg ttc gga gca tct gca aca gcc atg gct ttg ctg acg aag     1200
Val Leu Val Phe Gly Ala Ser Ala Thr Ala Met Ala Leu Leu Thr Lys
385                 390                 395                 400 act gtg tat ggg ctc tgg tac ctg agc tct gac ctt gtc tac atc atc     1248
Thr Val Tyr Gly Leu Trp Tyr Leu Ser Ser Asp Leu Val Tyr Ile Ile
                405                 410                 415 atc ttc cca cag ctg ctc tgt gta ctc ttc atc aaa gga acc aac act     1296
Ile Phe Pro Gln Leu Leu Cys Val Leu Phe Ile Lys Gly Thr Asn Thr
            420                 425                 430 tat ggg gca gtt gct ggt tat att ttt gga cta ttc ctg aga att act     1344
Tyr Gly Ala Val Ala Gly Tyr Ile Phe Gly Leu Phe Leu Arg Ile Thr
        435                 440                 445 gga gga gag cca tat cta tac ttg cag ccc tta atc ttc tac cct ggt     1392
Gly Gly Glu Pro Tyr Leu Tyr Leu Gln Pro Leu Ile Phe Tyr Pro Gly
    450                 455                 460 tat tac tct gac aag aat ggt ata tac aat cag agg ttc cca ttt aaa     1440
Tyr Tyr Ser Asp Lys Asn Gly Ile Tyr Asn Gln Arg Phe Pro Phe Lys
465                 470                 475                 480 act ctc tcc atg gtt acc tca ttc ttt acc aac att tgt gtt tct tat     1488
Thr Leu Ser Met Val Thr Ser Phe Phe Thr Asn Ile Cys Val Ser Tyr
                485                 490                 495 cta gcc aag tat cta ttt gaa agt gga acc ttg cct cca aaa tta gat     1536
Leu Ala Lys Tyr Leu Phe Glu Ser Gly Thr Leu Pro Pro Lys Leu Asp
            500                 505                 510 gta ttt gat gct gtt gtc gca agg cac agt gaa gag aac atg gac aag     1584
Val Phe Asp Ala Val Val Ala Arg His Ser Glu Glu Asn Met Asp Lys
        515                 520                 525 acc att cta gtc aga aat gaa aat atc aaa tta aat gaa ctt gca cct     1632
Thr Ile Leu Val Arg Asn Glu Asn Ile Lys Leu Asn Glu Leu Ala Pro
    530                 535                 540 gtg aaa cct cgg cag agc cta acc ctc agt tca act ttc acc aat aag     1680
Val Lys Pro Arg Gln Ser Leu Thr Leu Ser Ser Thr Phe Thr Asn Lys
545                 550                 555                 560 gag gcc ctc ctt gat gtt gat tcc agt ccg gag ggg tct ggg act gaa     1728
Glu Ala Leu Leu Asp Val Asp Ser Ser Pro Glu Gly Ser Gly Thr Glu
                565                 570                 575 gat aat tta caa tga                                                  1743
Asp Asn Leu Gln
            580

<210> SEQ ID NO 4
<211> LENGTH: 580
<212> TYPE: PRT
<213> ORGANISM: Mus musculus

<400> SEQUENCE: 4
```

-continued

```
Met Pro Phe His Val Glu Gly Leu Val Ala Ile Ile Leu Phe Tyr Leu
  1               5                  10                  15

Leu Ile Phe Leu Val Gly Ile Trp Ala Ala Trp Lys Thr Lys Asn Ser
             20                  25                  30

Gly Asn Pro Glu Glu Arg Ser Glu Ala Ile Ile Val Gly Gly Arg Asp
             35                  40                  45

Ile Gly Leu Leu Val Gly Gly Phe Thr Met Thr Ala Thr Trp Val Gly
         50                  55                  60

Gly Gly Tyr Ile Asn Gly Thr Ala Glu Ala Val Tyr Gly Pro Gly Cys
 65                  70                  75                  80

Gly Leu Ala Trp Ala His Ala Pro Ile Gly Tyr Ser Leu Ser Leu Ile
                 85                  90                  95

Leu Gly Gly Leu Phe Phe Ala Lys Pro Met Arg Ser Lys Gly Tyr Val
            100                 105                 110

Thr Met Leu Asp Pro Phe Lys Gln Ile Tyr Gly Lys Arg Met Gly Gly
            115                 120                 125

Leu Leu Phe Ile Pro Ala Leu Met Gly Glu Met Phe Trp Ala Ala Ala
130                 135                 140

Ile Phe Ser Ala Leu Gly Ala Thr Ile Ser Val Ile Ile Asp Val Asp
145                 150                 155                 160

Val Asn Ile Ser Val Ile Val Ser Ala Leu Ile Ala Ile Leu Tyr Thr
                165                 170                 175

Leu Val Gly Gly Leu Tyr Ser Val Ala Tyr Thr Asp Val Val Gln Leu
            180                 185                 190

Phe Cys Ile Phe Ile Gly Leu Trp Ile Ser Val Pro Phe Ala Leu Ser
            195                 200                 205

His Pro Ala Val Thr Asp Ile Gly Phe Thr Ala Val His Ala Lys Tyr
            210                 215                 220

Gln Ser Pro Trp Leu Gly Thr Ile Glu Ser Val Glu Val Tyr Thr Trp
225                 230                 235                 240

Leu Asp Asn Phe Leu Leu Leu Met Leu Gly Gly Ile Pro Trp Gln Ala
                245                 250                 255

Tyr Phe Gln Arg Val Leu Ser Ser Ser Ala Thr Tyr Ala Gln Val
            260                 265                 270

Leu Ser Phe Leu Ala Ala Phe Gly Cys Leu Val Met Ala Leu Pro Ala
            275                 280                 285

Ile Cys Ile Gly Ala Ile Gly Ala Ser Thr Asp Trp Asn Gln Thr Ala
290                 295                 300

Tyr Gly Tyr Pro Asp Pro Lys Thr Lys Glu Glu Ala Asp Met Ile Leu
305                 310                 315                 320

Pro Ile Val Leu Gln Tyr Leu Cys Pro Val Tyr Ile Ser Phe Phe Gly
                325                 330                 335

Leu Gly Ala Val Ser Ala Ala Val Met Ser Ser Ala Asp Ser Ser Ile
            340                 345                 350

Leu Ser Ala Ser Ser Met Phe Ala Arg Asn Ile Tyr Gln Leu Ser Phe
            355                 360                 365

Arg Gln Asn Ala Ser Asp Lys Glu Ile Val Trp Val Met Arg Ile Thr
            370                 375                 380

Val Leu Val Phe Gly Ala Ser Ala Thr Ala Met Ala Leu Leu Thr Lys
385                 390                 395                 400

Thr Val Tyr Gly Leu Trp Tyr Leu Ser Ser Asp Leu Val Tyr Ile Ile
                405                 410                 415
```

```
Ile Phe Pro Gln Leu Leu Cys Val Leu Phe Ile Lys Gly Thr Asn Thr
            420                 425                 430

Tyr Gly Ala Val Ala Gly Tyr Ile Phe Gly Leu Phe Leu Arg Ile Thr
            435                 440                 445

Gly Gly Glu Pro Tyr Leu Tyr Leu Gln Pro Leu Ile Phe Tyr Pro Gly
            450                 455                 460

Tyr Tyr Ser Asp Lys Asn Gly Ile Tyr Asn Gln Arg Phe Pro Phe Lys
465                 470                 475                 480

Thr Leu Ser Met Val Thr Ser Phe Phe Thr Asn Ile Cys Val Ser Tyr
                485                 490                 495

Leu Ala Lys Tyr Leu Phe Glu Ser Gly Thr Leu Pro Pro Lys Leu Asp
            500                 505                 510

Val Phe Asp Ala Val Ala Arg His Ser Glu Glu Asn Met Asp Lys
            515                 520                 525

Thr Ile Leu Val Arg Asn Glu Asn Ile Lys Leu Asn Glu Leu Ala Pro
            530                 535                 540

Val Lys Pro Arg Gln Ser Leu Thr Leu Ser Ser Thr Phe Thr Asn Lys
545                 550                 555                 560

Glu Ala Leu Leu Asp Val Asp Ser Ser Pro Gly Ser Gly Thr Glu
                565                 570                 575

Asp Asn Leu Gln
            580

<210> SEQ ID NO 5
<211> LENGTH: 4904
<212> TYPE: DNA
<213> ORGANISM: Rattus norvegicus
<220> FEATURE:
<221> NAME/KEY: CDS
<222> LOCATION: (224)..(1966)

<400> SEQUENCE: 5
cttttttcca ataccgaat tgattgatcg cctcgcccca cggagacctc agcgagctcc      60
ttgtcggcac cctccactca cctcgcgcct ccctccctcg ctgtcccaca cagctccgta     120 ctgggggga cacccggacc cctaaatcag ctccgggtga cgccaagaag atttgatgaa     180
gtagccctct gtggaaggat cttcacggta ccctaaataa aaa atg cct ttc cat      235
                                                Met Pro Phe His
                                                  1 gta gaa gga cta gta gcg att atc ctg ttc tac ctt ctt ata ttt ctg      283
Val Glu Gly Leu Val Ala Ile Ile Leu Phe Tyr Leu Leu Ile Phe Leu
  5                  10                  15                  20 gtt gga ata tgg gct gca tgg aaa acc aaa aac agc ggt aat gca gaa      331
Val Gly Ile Trp Ala Ala Trp Lys Thr Lys Asn Ser Gly Asn Ala Glu
                 25                  30                  35 gaa cgc agc gaa gcc atc ata gtt ggg ggc cga gac att ggt ttg ttg      379
Glu Arg Ser Glu Ala Ile Ile Val Gly Gly Arg Asp Ile Gly Leu Leu
             40                  45                  50 gtt ggt ggt ttt acc atg aca gcc acc tgg gtt gga gga ggt tac atc      427
Val Gly Gly Phe Thr Met Thr Ala Thr Trp Val Gly Gly Gly Tyr Ile
         55                  60                  65 aac ggg aca gct gaa gca gtt tat ggg cca ggt tgt ggt cta gct tgg      475
Asn Gly Thr Ala Glu Ala Val Tyr Gly Pro Gly Cys Gly Leu Ala Trp
     70                  75                  80 gct cag gca ccc att gga tat tct ctg agt ctg att tta ggt ggc ctg      523
Ala Gln Ala Pro Ile Gly Tyr Ser Leu Ser Leu Ile Leu Gly Gly Leu
 85                  90                  95                 100 ttt ttt gca aaa cct atg cgt tcc aag gga tat gtg act atg tta gac      571
```

```
                Phe Phe Ala Lys Pro Met Arg Ser Lys Gly Tyr Val Thr Met Leu Asp
                            105                 110                 115 ccg ttt caa cag atc tat gga aag cgc atg ggt ggg ctg ctg ttc atc             619
Pro Phe Gln Gln Ile Tyr Gly Lys Arg Met Gly Gly Leu Leu Phe Ile
            120                 125                 130 cct gca ctg atg gga gag atg ttc tgg gct gca gca att ttc tct gca             667
Pro Ala Leu Met Gly Glu Met Phe Trp Ala Ala Ala Ile Phe Ser Ala
        135                 140                 145 tta ggg gct acc atc agc gta atc att gat gtg gat gtg aac ata tcg             715
Leu Gly Ala Thr Ile Ser Val Ile Ile Asp Val Asp Val Asn Ile Ser
    150                 155                 160 gtc att gtc tcc gca ctc att gcc att ctt tat acc ctc gtg gga ggg             763
Val Ile Val Ser Ala Leu Ile Ala Ile Leu Tyr Thr Leu Val Gly Gly
165                 170                 175                 180 ctc tac tct gtg gca tat act gat gtt gta cag cta ttc tgc att ttt             811
Leu Tyr Ser Val Ala Tyr Thr Asp Val Val Gln Leu Phe Cys Ile Phe
                185                 190                 195 ata gga ttg tgg atc agt gtc cca ttt gcc ctg tca cat cct gca gtc             859
Ile Gly Leu Trp Ile Ser Val Pro Phe Ala Leu Ser His Pro Ala Val
            200                 205                 210 acc gac att gga ttc act gct gtg cat gct aaa tac cag agt ccc tgg             907
Thr Asp Ile Gly Phe Thr Ala Val His Ala Lys Tyr Gln Ser Pro Trp
        215                 220                 225 ctg gga acc att gaa tca gtt gaa gtc tac acc tgg ctt gat aat ttt             955
Leu Gly Thr Ile Glu Ser Val Glu Val Tyr Thr Trp Leu Asp Asn Phe
    230                 235                 240 ctg ttg ttg atg ctg ggt gga ata cca tgg caa gcc tac ttc cag agg            1003
Leu Leu Leu Met Leu Gly Gly Ile Pro Trp Gln Ala Tyr Phe Gln Arg
245                 250                 255                 260 gtc ctc tct tca tcg tca gcg acc tat gct cag gtg ctg tcc ttc ctg            1051
Val Leu Ser Ser Ser Ser Ala Thr Tyr Ala Gln Val Leu Ser Phe Leu
                265                 270                 275 gca gct ttt ggg tgc ctg gtg atg gct cta cca gcc att tgc att ggg            1099
Ala Ala Phe Gly Cys Leu Val Met Ala Leu Pro Ala Ile Cys Ile Gly
            280                 285                 290 gcc att gga gcc tcc aca gac tgg aac caa act gca tat ggg ttt cca            1147
Ala Ile Gly Ala Ser Thr Asp Trp Asn Gln Thr Ala Tyr Gly Phe Pro
        295                 300                 305 gat ccc aag acc aag gag gaa gca gac atg att ctc ccg att gtt cta            1195
Asp Pro Lys Thr Lys Glu Glu Ala Asp Met Ile Leu Pro Ile Val Leu
    310                 315                 320 cag tac ctc tgc cct gtg tac att tcc ttc ttt ggg ctt ggt gct gtt            1243
Gln Tyr Leu Cys Pro Val Tyr Ile Ser Phe Phe Gly Leu Gly Ala Val
325                 330                 335                 340 tct gct gct gtc atg tcc tcg gct gac tca tcc atc cta tca gca agt            1291
Ser Ala Ala Val Met Ser Ser Ala Asp Ser Ser Ile Leu Ser Ala Ser
                345                 350                 355 tcc atg ttt gct cgg aat atc tac cag ctt tcc ttc aga caa aat gca            1339
Ser Met Phe Ala Arg Asn Ile Tyr Gln Leu Ser Phe Arg Gln Asn Ala
            360                 365                 370 tca gac aag gaa att gtg tgg gtc atg agg atc act gtg ttt gtg ttt            1387
Ser Asp Lys Glu Ile Val Trp Val Met Arg Ile Thr Val Phe Val Phe
        375                 380                 385 gga gca tct gca aca gcc atg gcc ttg ctc acg aag act gtg tat ggg            1435
Gly Ala Ser Ala Thr Ala Met Ala Leu Leu Thr Lys Thr Val Tyr Gly
    390                 395                 400 ctc tgg tac ctg agc tct gac ctt gtc tac atc atc atc ttc cca cag            1483
Leu Trp Tyr Leu Ser Ser Asp Leu Val Tyr Ile Ile Ile Phe Pro Gln
405                 410                 415                 420
```

```
ctg ctc tgt gta ctc ttc atc aaa gga acc aac act tat ggg gca gtt       1531
Leu Leu Cys Val Leu Phe Ile Lys Gly Thr Asn Thr Tyr Gly Ala Val
                425                 430                 435 gct ggt tat att ttt gga ctt ttc ctg aga att acc gga gga gag cca       1579
Ala Gly Tyr Ile Phe Gly Leu Phe Leu Arg Ile Thr Gly Gly Glu Pro
            440                 445                 450 tat cta tac ttg cag ccc tta atc ttc tac cct ggt tat tac cct gac       1627
Tyr Leu Tyr Leu Gln Pro Leu Ile Phe Tyr Pro Gly Tyr Tyr Pro Asp
        455                 460                 465 aag aat ggt ata tac aat cag agg ttc cca ttt aaa act ctc tcc atg       1675
Lys Asn Gly Ile Tyr Asn Gln Arg Phe Pro Phe Lys Thr Leu Ser Met
    470                 475                 480 gtt acc tca ttc ttt acc aac att tgt gtt tcc tat cta gcc aag tat       1723
Val Thr Ser Phe Phe Thr Asn Ile Cys Val Ser Tyr Leu Ala Lys Tyr
485                 490                 495                 500 cta ttt gaa agt gga acc ttg cct cca aaa tta gat ata ttt gat gct       1771
Leu Phe Glu Ser Gly Thr Leu Pro Pro Lys Leu Asp Ile Phe Asp Ala
                505                 510                 515 gtt gtc tca agg cac agt gaa gag aac atg gac aag acc att cta gtc       1819
Val Val Ser Arg His Ser Glu Glu Asn Met Asp Lys Thr Ile Leu Val
            520                 525                 530 aga aat gaa aac atc aaa tta aat gaa ctt gca cct gta aag cct cga       1867
Arg Asn Glu Asn Ile Lys Leu Asn Glu Leu Ala Pro Val Lys Pro Arg
        535                 540                 545 cag agc cta acc ctc agt tca act ttc acc aat aaa gag gct ctc ctt       1915
Gln Ser Leu Thr Leu Ser Ser Thr Phe Thr Asn Lys Glu Ala Leu Leu
    550                 555                 560 gat gtt gat tcc agt cca gag gga tct ggg act gaa gat aac tta caa       1963
Asp Val Asp Ser Ser Pro Glu Gly Ser Gly Thr Glu Asp Asn Leu Gln
565                 570                 575                 580 tga ccccatgtaa aatatacaga acagggcatt gctgtagggt aatactggga            2016
aaaaggtttg gagcatatct tatacatgtt acaatataaa tgtttgagga aaaaagttttt    2076 tcagaaataa gatattatgg atgagttcag aaaaataaca attgcacagt gaggcagaag    2136
caagcgtgaa ggcaacagct ttatttctca tcgtagcact tttcattttg aatagctttg    2196
ttaagcacat aaaaatgcat aaagccccag ccaaagaaag tggccaaata ttatttatct    2256
ttattatgga aggaaggaat atttattaaa aagtccattg gaaggagatt ggatggtccc    2316
gatcattttc actggcgaat gcactggata acagattaat tactacaaca tggaggttat    2376
gcatgtattc acggtcacta ctgtgaagga tgcagtgggt tagccagtac acttttcccc    2436
atgggtaggt tgtctggctc tcccataatc ttaactatgg catttaccca tttttcaagg    2496
tgtgctttct tacccttttt tgccatctag catgtgtact ctctccattc atccctccat    2556
ctatctatcc ctccttcttt ctacactctc tcctttcttc tgctctttcc ctttcactcc    2616
ctttctccct tctctttatc tctttatatt ttgtttctgt gaggggctgg aactctatta    2676
cagggccttg cacatgctaa gtaagagctc tcctactgag ctacattgca acctcacaat    2736
aatttatttt tttagtaata tcgtacatta ttctaagcac aagcaacaca acaatatctt    2796
atttaatagt gacattttta tgtgaaaatg atagaaaaca gagtttatgt tggagtaaga    2856
tagaagcact gagcccttta agtgtgacca cagttgctat atgctcaaag agaagggtcc    2916
aaaaccaagc atgaaatggt tgttgggcag cattacagca ataagtcaag aagaaaagga    2976
aaagaaggag aagaagaaaa acggatttct gtctccagct tttatacatt aaatgttgtt    3036
acacattata aatataatgt cttggcttat cttctaagag tattggaggc aaagttgagc    3096
catatataaa gtgtggtttc tgtctaacat ctgttacaag tgccacctgc ttcatcagca    3156
```

-continued

```
tgcattcgac gcatatatat taccagcagt tcccaaataa ctctctgaga aactgggaaa   3216
caaaccctgc ttacttttgg acatccaata atgtaagagt ttagtgctaa ggatctactc   3276
ttgacacttt tccacataag ccattttag ggactggaca gatcaccaca agtgtgtata    3336
ttgattttca aatgtaatag aaaacaaaaa gtaaaacaa gtcatagaag aagccatcat    3396
ttttaatgtc ttttgtgtac atggatttca ggaggtcaat cattaaatgt aattttgctt   3456
ttctttgtag cattcagaat tacatataaa acttgtgcca ccaaaccta gaattctttt    3516
tataagttac agttattatc tcttaaagca tcacatttgg aactcctttc tttaaaaagg   3576
atgacttaaa aattcctact gtgactttta aaatgtaaaa ttaaataatt ttacatattg   3636
taatgtccta tttttcagga ttgtctcaat ccttaaacca ctttactgat ttgtgtatgt   3696
acgtaaggaa gagaattcat ttaccctcca gtttatctca gaatcagctc actagctatg   3756
gagtagttat ggaaattatg gagtctgaga tgttcaaaca tggtgtgaga aaagagtcaa   3816
aggaaaaaag aaaacacaga taaaaagta gtaaactttg tacttgaaaa tctactagtg    3876
acaatgaaat ttctggtaaa catggtattt cagatgcaca aagtcttcca acagagacaa   3936
aagagaaact tttgcccaac tcatgatctt ccatgaaatt gttgaggtgt ttgcttgcat   3996
taggaacatc acagaacctc actcacacta gatctcacag cgaagcaggt tcctttcaca   4056
gacattacac tttgtaatgc tcttagtcaa caactgtcca actaagctta aaatatttaa   4116
agtatcataa tagcaaaaat gagagaagaa tcccaagata tttatttatg catactcttg   4176
aatggaattc cccatgattt ccaagaaaga gatgatgctt caaggtatat tggattggag   4236
acatctctaa attattccag attcaagcag cagacctcat tttcaaatcc ccaatgaaat   4296
caaaataacc caaatgtttc agcctcttgc ttgggaagta atacatgtgg atagcatttg   4356
agcaagatag gagtttcact cctatatatt aacaatgatt gtgctatgtt tcttaggtaa   4416
tttgtgttcc tctccatgtg ttcagaacat caagcttgta gctggaacga tatgttaaca   4476
agctgtcaaa tgctcagtgc caaaatccaa tttcattgtt atacttacaa gtaatgaatt   4536
ttatgtgcat attatatgaa tgtaagcttg aaatgaatgc atttaatatt taatataatg   4596
tatattgaaa atgtcatttg taaataatga attagcatta tattttaaac ataaatcatc   4656
atttcccttt ttgtccttct acaaaatttg ctctggtatc ctatgtaacg tataataagt   4716
ttgttataat gtatgttggc tactgcatag acaaatgcat agaattgttc caaaacttat   4776
atttttatct gtcaaaatgt tatacaaaat tatacagaaa taagtagatt tacaagtaca   4836
catgtatgtg ttcaaatgta atgatactgt attaaattat tccattgcaa ttcaaaaaaa   4896
aaaaaaaa                                                            4904
```

<210> SEQ ID NO 6
<211> LENGTH: 580
<212> TYPE: PRT
<213> ORGANISM: Rattus norvegicus

<400> SEQUENCE: 6

```
Met Pro Phe His Val Glu Gly Leu Val Ala Ile Ile Leu Phe Tyr Leu
 1               5                  10                  15

Leu Ile Phe Leu Val Gly Ile Trp Ala Ala Trp Lys Thr Lys Asn Ser
            20                  25                  30

Gly Asn Ala Glu Glu Arg Ser Glu Ala Ile Ile Val Gly Gly Arg Asp
        35                  40                  45

Ile Gly Leu Leu Val Gly Gly Phe Thr Met Thr Ala Thr Trp Val Gly
```

-continued

```
            50                  55                  60
Gly Gly Tyr Ile Asn Gly Thr Ala Glu Ala Val Tyr Gly Pro Gly Cys
 65                  70                  75                  80

Gly Leu Ala Trp Ala Gln Ala Pro Ile Gly Tyr Ser Leu Ser Leu Ile
                 85                  90                  95

Leu Gly Gly Leu Phe Phe Ala Lys Pro Met Arg Ser Lys Gly Tyr Val
                100                 105                 110

Thr Met Leu Asp Pro Phe Gln Gln Ile Tyr Gly Lys Arg Met Gly Gly
                115                 120                 125

Leu Leu Phe Ile Pro Ala Leu Met Gly Glu Met Phe Trp Ala Ala Ala
130                 135                 140

Ile Phe Ser Ala Leu Gly Ala Thr Ile Ser Val Ile Asp Val Asp
145                 150                 155                 160

Val Asn Ile Ser Val Ile Val Ser Ala Leu Ile Ala Ile Leu Tyr Thr
                165                 170                 175

Leu Val Gly Gly Leu Tyr Ser Val Ala Tyr Thr Asp Val Val Gln Leu
                180                 185                 190

Phe Cys Ile Phe Ile Gly Leu Trp Ile Ser Val Pro Phe Ala Leu Ser
195                 200                 205

His Pro Ala Val Thr Asp Ile Gly Phe Thr Ala Val His Ala Lys Tyr
        210                 215                 220

Gln Ser Pro Trp Leu Gly Thr Ile Glu Ser Val Glu Val Tyr Thr Trp
225                 230                 235                 240

Leu Asp Asn Phe Leu Leu Leu Met Leu Gly Gly Ile Pro Trp Gln Ala
                245                 250                 255

Tyr Phe Gln Arg Val Leu Ser Ser Ser Ala Thr Tyr Ala Gln Val
                260                 265                 270

Leu Ser Phe Leu Ala Ala Phe Gly Cys Leu Val Met Ala Leu Pro Ala
        275                 280                 285

Ile Cys Ile Gly Ala Ile Gly Ala Ser Thr Asp Trp Asn Gln Thr Ala
290                 295                 300

Tyr Gly Phe Pro Asp Pro Lys Thr Lys Glu Glu Ala Asp Met Ile Leu
305                 310                 315                 320

Pro Ile Val Leu Gln Tyr Leu Cys Pro Val Tyr Ile Ser Phe Phe Gly
                325                 330                 335

Leu Gly Ala Val Ser Ala Ala Val Met Ser Ser Ala Asp Ser Ser Ile
                340                 345                 350

Leu Ser Ala Ser Ser Met Phe Ala Arg Asn Ile Tyr Gln Leu Ser Phe
        355                 360                 365

Arg Gln Asn Ala Ser Asp Lys Glu Ile Val Trp Val Met Arg Ile Thr
370                 375                 380

Val Phe Val Phe Gly Ala Ser Ala Thr Ala Met Ala Leu Leu Thr Lys
385                 390                 395                 400

Thr Val Tyr Gly Leu Trp Tyr Leu Ser Ser Asp Leu Val Tyr Ile Ile
                405                 410                 415

Ile Phe Pro Gln Leu Leu Cys Val Leu Phe Ile Lys Gly Thr Asn Thr
                420                 425                 430

Tyr Gly Ala Val Ala Gly Tyr Ile Phe Gly Leu Phe Leu Arg Ile Thr
        435                 440                 445

Gly Gly Glu Pro Tyr Leu Tyr Leu Gln Pro Leu Ile Phe Tyr Pro Gly
        450                 455                 460

Tyr Tyr Pro Asp Lys Asn Gly Ile Tyr Asn Gln Arg Phe Pro Phe Lys
465                 470                 475                 480
```

```
Thr Leu Ser Met Val Thr Ser Phe Phe Thr Asn Ile Cys Val Ser Tyr
                485                 490                 495

Leu Ala Lys Tyr Leu Phe Glu Ser Gly Thr Leu Pro Pro Lys Leu Asp
            500                 505                 510

Ile Phe Asp Ala Val Val Ser Arg His Ser Glu Glu Asn Met Asp Lys
            515                 520                 525

Thr Ile Leu Val Arg Asn Glu Asn Ile Lys Leu Asn Glu Leu Ala Pro
        530                 535                 540

Val Lys Pro Arg Gln Ser Leu Thr Leu Ser Ser Thr Phe Thr Asn Lys
545                 550                 555                 560

Glu Ala Leu Leu Asp Val Asp Ser Ser Pro Glu Gly Ser Gly Thr Glu
                565                 570                 575

Asp Asn Leu Gln
            580

<210> SEQ ID NO 7
<211> LENGTH: 1985
<212> TYPE: DNA
<213> ORGANISM: Caenorhabditis elegans
<220> FEATURE:
<221> NAME/KEY: CDS
<222> LOCATION: (9)..(1739)

<400> SEQUENCE: 7 tgacaaat atg gcc gac tta ttg ggt atc gtg gcc att gtg ttc ttc tac        50
        Met Ala Asp Leu Leu Gly Ile Val Ala Ile Val Phe Phe Tyr
          1               5                  10 gtg ctc att ctt gtc gtt gga ata tgg gcg ggt aga aaa tcg aaa agt        98
Val Leu Ile Leu Val Val Gly Ile Trp Ala Gly Arg Lys Ser Lys Ser
 15                  20                  25                  30 tca aaa gag ctt gaa tca gaa gcc ggc gcg gcg acg gaa gag gtg atg       146
Ser Lys Glu Leu Glu Ser Glu Ala Gly Ala Ala Thr Glu Glu Val Met
                 35                  40                  45 tta gct ggg aga aac atc gga act ctt gtc gga att ttc aca atg act       194
Leu Ala Gly Arg Asn Ile Gly Thr Leu Val Gly Ile Phe Thr Met Thr
             50                  55                  60 gcc acg tgg gtt ggc ggt gct tat atc aat gga acc gcc gag gct ctg       242
Ala Thr Trp Val Gly Gly Ala Tyr Ile Asn Gly Thr Ala Glu Ala Leu
         65                  70                  75 tat aat gga ggt ctc ctt gga tgt cag gct cca gtt gga tat gca att       290
Tyr Asn Gly Gly Leu Leu Gly Cys Gln Ala Pro Val Gly Tyr Ala Ile
     80                  85                  90 tcc ctt gtt atg gga gga cta ctt ttc gca aag aaa atg cga gaa gaa       338
Ser Leu Val Met Gly Gly Leu Leu Phe Ala Lys Lys Met Arg Glu Glu
 95                 100                 105                 110 gga tat att aca atg ctc gat cct ttt cag cac aaa tat ggc caa cga       386
Gly Tyr Ile Thr Met Leu Asp Pro Phe Gln His Lys Tyr Gly Gln Arg
                115                 120                 125 atc ggt ggc ttg atg tat gtt cca gca ctt ctt ggt gaa aca ttc tgg       434
Ile Gly Gly Leu Met Tyr Val Pro Ala Leu Leu Gly Glu Thr Phe Trp
            130                 135                 140 aca gca gcc att ctt tcg gca ctt ggt gca aca ctg tcg gta att ctt       482
Thr Ala Ala Ile Leu Ser Ala Leu Gly Ala Thr Leu Ser Val Ile Leu
        145                 150                 155 gga atc gac atg aat gca tca gtg acc ctg tcg gcc tgt att gcc gta       530
Gly Ile Asp Met Asn Ala Ser Val Thr Leu Ser Ala Cys Ile Ala Val
    160                 165                 170 ttc tac aca ttc acc ggt gga tac tat gca gtc gcg tac act gac gtc       578
Phe Tyr Thr Phe Thr Gly Gly Tyr Tyr Ala Val Ala Tyr Thr Asp Val
```

```
                                                      -continued
         175                 180                 185                 190
gtt caa cta ttt tgc att ttc gtc ggt ttg tgg gtt tgc gtg ccg gcg            626
Val Gln Leu Phe Cys Ile Phe Val Gly Leu Trp Val Cys Val Pro Ala
                    195                 200                 205 gct atg gtg cat gat ggt gcg aag gat att tcc agg aat gca ggc gac            674
Ala Met Val His Asp Gly Ala Lys Asp Ile Ser Arg Asn Ala Gly Asp
            210                 215                 220 tgg att gga gag att gga gga ttc aaa gaa aca tct ctc tgg att gat            722
Trp Ile Gly Glu Ile Gly Gly Phe Lys Glu Thr Ser Leu Trp Ile Asp
        225                 230                 235 tgc atg ctt ctc ctt gtc ttt gga gga att cca tgg caa gtg tac ttc            770
Cys Met Leu Leu Leu Val Phe Gly Gly Ile Pro Trp Gln Val Tyr Phe
    240                 245                 250 caa aga gtt ctc tcc tca aaa act gct cat gga gca cag acg ttg tcg            818
Gln Arg Val Leu Ser Ser Lys Thr Ala His Gly Ala Gln Thr Leu Ser
255                 260                 265                 270 ttt gtg gcg ggc gtc gga tgc att ctc atg gcg att cca cca gcg ttg            866
Phe Val Ala Gly Val Gly Cys Ile Leu Met Ala Ile Pro Pro Ala Leu
                275                 280                 285 atc ggt gca att gcc agg aac aca gac tgg aga atg act gat tat tcc            914
Ile Gly Ala Ile Ala Arg Asn Thr Asp Trp Arg Met Thr Asp Tyr Ser
            290                 295                 300 cca tgg aac aat gga act aag gtc gaa tcg att cca ccg gat aag aga            962
Pro Trp Asn Asn Gly Thr Lys Val Glu Ser Ile Pro Pro Asp Lys Arg
        305                 310                 315 aac atg gtg gtc ccg ttg gta ttc cag tat ctt acg cca aga tgg gtc           1010
Asn Met Val Val Pro Leu Val Phe Gln Tyr Leu Thr Pro Arg Trp Val
    320                 325                 330 gcc ttt att gga ctc ggc gca gtg tcg gct gct gta atg tca tct gca           1058
Ala Phe Ile Gly Leu Gly Ala Val Ser Ala Ala Val Met Ser Ser Ala
335                 340                 345                 350 gat tca tct gta cta tca gca gca tca atg ttt gct cac aac atc tgg           1106
Asp Ser Ser Val Leu Ser Ala Ala Ser Met Phe Ala His Asn Ile Trp
                355                 360                 365 aag ctc aca att cgc cct cac gcg tct gaa aaa gaa gtg ata att gtg           1154
Lys Leu Thr Ile Arg Pro His Ala Ser Glu Lys Glu Val Ile Ile Val
            370                 375                 380 atg aga ata gcc atc atc tgt gtt ggt atc atg gca acc atc atg gca           1202
Met Arg Ile Ala Ile Ile Cys Val Gly Ile Met Ala Thr Ile Met Ala
        385                 390                 395 ctt acc att caa tcc atc tat ggg ctt tgg tat ctt tgt gca gat ttg           1250
Leu Thr Ile Gln Ser Ile Tyr Gly Leu Trp Tyr Leu Cys Ala Asp Leu
    400                 405                 410 gtc tac gtc ata ctc ttc cct caa cta tta tgt gtt gta tat atg cca           1298
Val Tyr Val Ile Leu Phe Pro Gln Leu Leu Cys Val Val Tyr Met Pro
415                 420                 425                 430 cgt agc aat acg tat ggc tca ttg gct ggc tat gca gtc ggt ctt gtg           1346
Arg Ser Asn Thr Tyr Gly Ser Leu Ala Gly Tyr Ala Val Gly Leu Val
                435                 440                 445 ctc cgt ttg att gga ggc gag cca ctt gta tcg ctg cca gcg ttc ttc           1394
Leu Arg Leu Ile Gly Gly Glu Pro Leu Val Ser Leu Pro Ala Phe Phe
            450                 455                 460 cat tat cca atg tat acg gat ggg gta cag tat ttc cca ttc agg aca           1442
His Tyr Pro Met Tyr Thr Asp Gly Val Gln Tyr Phe Pro Phe Arg Thr
        465                 470                 475 act gct atg tta tct tca atg gct act atc tac att gta tca ata caa           1490
Thr Ala Met Leu Ser Ser Met Ala Thr Ile Tyr Ile Val Ser Ile Gln
    480                 485                 490 tcg gag aag ctg ttc aaa tcg gga cgt ttg tct ccg gag tgg gac gta           1538
```

```
Ser Glu Lys Leu Phe Lys Ser Gly Arg Leu Ser Pro Glu Trp Asp Val
495                 500                 505                 510 atg ggt tgt gta gtg aat att ccg ata gat cat gta ccc ctt ccg tca      1586
Met Gly Cys Val Val Asn Ile Pro Ile Asp His Val Pro Leu Pro Ser
                    515                 520                 525 gat gta tcg ttt gct gtt agt agt gag acc ttg aat atg aag gct cca      1634
Asp Val Ser Phe Ala Val Ser Ser Glu Thr Leu Asn Met Lys Ala Pro
                530                 535                 540 aac gga aca ccg gct cca gta cat ccg aac caa cag ccg tct gat gaa      1682
Asn Gly Thr Pro Ala Pro Val His Pro Asn Gln Gln Pro Ser Asp Glu
            545                 550                 555 aat aca tta tta cat cca tat tcg gac caa agt tat tat tcc aca aat      1730
Asn Thr Leu Leu His Pro Tyr Ser Asp Gln Ser Tyr Tyr Ser Thr Asn
        560                 565                 570 agc aat taa aagagacgaa cttgttccac gtgttcactt aatttcctcc              1779
Ser Asn
575 caaattttt  tttgtatttt  ttttagtttt  cgttaacttt  tttctcactt  tctcaaattt  1839
cagatctcta  ttaatagacc  catccggtgg  atacacttta  gtttttattt  attttcctaa  1899
aatttgaaag  aaaaaaattt  gatgaatttt  gacatgttca  gaaattccaa  taaaaacgtg  1959
accaattaat  taaaaaaaaa  aaaaaa                                         1985

<210> SEQ ID NO 8
<211> LENGTH: 576
<212> TYPE: PRT
<213> ORGANISM: Caenorhabditis elegans

<400> SEQUENCE: 8

Met Ala Asp Leu Leu Gly Ile Val Ala Ile Val Phe Phe Tyr Val Leu
1               5                   10                  15

Ile Leu Val Val Gly Ile Trp Ala Gly Arg Lys Ser Lys Ser Ser Lys
                20                  25                  30

Glu Leu Glu Ser Glu Ala Gly Ala Ala Thr Glu Glu Val Met Leu Ala
            35                  40                  45

Gly Arg Asn Ile Gly Thr Leu Val Gly Ile Phe Thr Met Thr Ala Thr
        50                  55                  60

Trp Val Gly Gly Ala Tyr Ile Asn Gly Thr Ala Glu Ala Leu Tyr Asn
65                  70                  75                  80

Gly Gly Leu Leu Gly Cys Gln Ala Pro Val Gly Tyr Ala Ile Ser Leu
                85                  90                  95

Val Met Gly Gly Leu Leu Phe Ala Lys Lys Met Arg Glu Glu Gly Tyr
            100                 105                 110

Ile Thr Met Leu Asp Pro Phe Gln His Lys Tyr Gly Gln Arg Ile Gly
        115                 120                 125

Gly Leu Met Tyr Val Pro Ala Leu Leu Gly Glu Thr Phe Trp Thr Ala
    130                 135                 140

Ala Ile Leu Ser Ala Leu Gly Ala Thr Leu Ser Val Ile Leu Gly Ile
145                 150                 155                 160

Asp Met Asn Ala Ser Val Thr Leu Ser Ala Cys Ile Ala Val Phe Tyr
                165                 170                 175

Thr Phe Thr Gly Gly Tyr Tyr Ala Val Ala Tyr Thr Asp Val Val Gln
            180                 185                 190

Leu Phe Cys Ile Phe Val Gly Leu Trp Val Cys Val Pro Ala Ala Met
        195                 200                 205

Val His Asp Gly Ala Lys Asp Ile Ser Arg Asn Ala Gly Asp Trp Ile
```

```
                210                 215                 220
Gly Glu Ile Gly Gly Phe Lys Glu Thr Ser Leu Trp Ile Asp Cys Met
225                 230                 235                 240

Leu Leu Leu Val Phe Gly Gly Ile Pro Trp Gln Val Tyr Phe Gln Arg
                245                 250                 255

Val Leu Ser Ser Lys Thr Ala His Gly Ala Gln Thr Leu Ser Phe Val
                260                 265                 270

Ala Gly Val Gly Cys Ile Leu Met Ala Ile Pro Pro Ala Leu Ile Gly
                275                 280                 285

Ala Ile Ala Arg Asn Thr Asp Trp Arg Met Thr Asp Tyr Ser Pro Trp
290                 295                 300

Asn Asn Gly Thr Lys Val Glu Ser Ile Pro Pro Asp Lys Arg Asn Met
305                 310                 315                 320

Val Val Pro Leu Val Phe Gln Tyr Leu Thr Pro Arg Trp Val Ala Phe
                325                 330                 335

Ile Gly Leu Gly Ala Val Ser Ala Ala Val Met Ser Ser Ala Asp Ser
                340                 345                 350

Ser Val Leu Ser Ala Ala Ser Met Phe Ala His Asn Ile Trp Lys Leu
                355                 360                 365

Thr Ile Arg Pro His Ala Ser Glu Lys Glu Val Ile Ile Val Met Arg
370                 375                 380

Ile Ala Ile Ile Cys Val Gly Ile Met Ala Thr Ile Met Ala Leu Thr
385                 390                 395                 400

Ile Gln Ser Ile Tyr Gly Leu Trp Tyr Leu Cys Ala Asp Leu Val Tyr
                405                 410                 415

Val Ile Leu Phe Pro Gln Leu Leu Cys Val Val Tyr Met Pro Arg Ser
                420                 425                 430

Asn Thr Tyr Gly Ser Leu Ala Gly Tyr Ala Val Gly Leu Val Leu Arg
                435                 440                 445

Leu Ile Gly Gly Glu Pro Leu Val Ser Leu Pro Ala Phe Phe His Tyr
                450                 455                 460

Pro Met Tyr Thr Asp Gly Val Gln Tyr Phe Pro Phe Arg Thr Thr Ala
465                 470                 475                 480

Met Leu Ser Ser Met Ala Thr Ile Tyr Ile Val Ser Ile Gln Ser Glu
                485                 490                 495

Lys Leu Phe Lys Ser Gly Arg Leu Ser Pro Glu Trp Asp Val Met Gly
                500                 505                 510

Cys Val Val Asn Ile Pro Ile Asp His Val Pro Leu Pro Ser Asp Val
                515                 520                 525

Ser Phe Ala Val Ser Ser Glu Thr Leu Asn Met Lys Ala Pro Asn Gly
                530                 535                 540

Thr Pro Ala Pro Val His Pro Asn Gln Gln Pro Ser Asp Glu Asn Thr
545                 550                 555                 560

Leu Leu His Pro Tyr Ser Asp Gln Ser Tyr Tyr Ser Thr Asn Ser Asn
                565                 570                 575

<210> SEQ ID NO 9
<211> LENGTH: 1813
<212> TYPE: DNA
<213> ORGANISM: Homo sapiens
<220> FEATURE:
<221> NAME/KEY: CDS
<222> LOCATION: (19)..(1761)

<400> SEQUENCE: 9
```

-continued

| | |
|---|---|
| ctggatcatt agataaaa atg gct ttc cat gtg gaa gga ctg ata gct atc<br>           Met Ala Phe His Val Glu Gly Leu Ile Ala Ile<br>            1       5           10 | 51 |
| atc gtg ttc tac ctt cta att ttg ctg gtt gga ata tgg gct gcc tgg<br>Ile Val Phe Tyr Leu Leu Ile Leu Leu Val Gly Ile Trp Ala Ala Trp<br>     15          20          25 | 99 |
| aga acc aaa aac agt ggc agc gca gaa gag cgc agc gaa gcc atc ata<br>Arg Thr Lys Asn Ser Gly Ser Ala Glu Glu Arg Ser Glu Ala Ile Ile<br>     30          35          40 | 147 |
| gtt ggt ggc cga gat att ggt tta ttg gtt ggt gga ttt acc atg aca<br>Val Gly Gly Arg Asp Ile Gly Leu Leu Val Gly Gly Phe Thr Met Thr<br>   45          50          55 | 195 |
| gct acc tgg gtc gga gga ggg tat atc aat ggc aca gct gaa gca gtt<br>Ala Thr Trp Val Gly Gly Gly Tyr Ile Asn Gly Thr Ala Glu Ala Val<br>60         65          70         75 | 243 |
| tat gta cca ggt tat ggc cta gct tgg gct cag gca cca att gga tat<br>Tyr Val Pro Gly Tyr Gly Leu Ala Trp Ala Gln Ala Pro Ile Gly Tyr<br>        80          85         90 | 291 |
| tct ctt agt ctg att tta ggt ggc ctg ttc ttt gca aaa cct atg cgt<br>Ser Leu Ser Leu Ile Leu Gly Gly Leu Phe Phe Ala Lys Pro Met Arg<br>     95          100        105 | 339 |
| tca aag ggg tat gtg acc atg tta gac ccg ttt cag caa atc tat gga<br>Ser Lys Gly Tyr Val Thr Met Leu Asp Pro Phe Gln Gln Ile Tyr Gly<br>     110         115        120 | 387 |
| aaa cgc atg ggc gga ctc ctg ttt att cct gca ctg atg gga gaa atg<br>Lys Arg Met Gly Gly Leu Leu Phe Ile Pro Ala Leu Met Gly Glu Met<br>   125          130        135 | 435 |
| ttc tgg gct gca gca att ttc tct gct ttg gga gcc acc atc agc gtg<br>Phe Trp Ala Ala Ala Ile Phe Ser Ala Leu Gly Ala Thr Ile Ser Val<br>140         145          150        155 | 483 |
| atc atc gat gtg gat atg cac att tct gtc atc atc tct gca ctc att<br>Ile Ile Asp Val Asp Met His Ile Ser Val Ile Ile Ser Ala Leu Ile<br>        160          165        170 | 531 |
| gcc act ctg tac aca ctg gtg gga ggg ctc tat tct gtg gcc tac act<br>Ala Thr Leu Tyr Thr Leu Val Gly Gly Leu Tyr Ser Val Ala Tyr Thr<br>     175          180        185 | 579 |
| gat gtc gtt cag ctc ttt tgc att ttt gta ggg ctg tgg atc agc gtc<br>Asp Val Val Gln Leu Phe Cys Ile Phe Val Gly Leu Trp Ile Ser Val<br>   190          195        200 | 627 |
| ccc ttt gca ttg tca cat cct gca gtc gca gac atc ggg ttc act gct<br>Pro Phe Ala Leu Ser His Pro Ala Val Ala Asp Ile Gly Phe Thr Ala<br>205         210          215 | 675 |
| gtg cat gcc aaa tac caa aag ccg tgg ctg gga act gtt gac tca tct<br>Val His Ala Lys Tyr Gln Lys Pro Trp Leu Gly Thr Val Asp Ser Ser<br>220         225          230        235 | 723 |
| gaa gtc tac tct tgg ctt gat agt ttt ctg ttg ttg atg ctg ggt gga<br>Glu Val Tyr Ser Trp Leu Asp Ser Phe Leu Leu Leu Met Leu Gly Gly<br>     240          245        250 | 771 |
| atc cca tgg caa gca tac ttt cag agg gtt ctc tct tct tcc tca gcc<br>Ile Pro Trp Gln Ala Tyr Phe Gln Arg Val Leu Ser Ser Ser Ser Ala<br>   255          260        265 | 819 |
| acc tat gct caa gtg ctg tcc ttc ctg gca gct ttc ggg tgc ctg gtg<br>Thr Tyr Ala Gln Val Leu Ser Phe Leu Ala Ala Phe Gly Cys Leu Val<br>270         275          280 | 867 |
| atg gcc atc cca gcc ata ctc att ggg gcc att gga gca tca aca gac<br>Met Ala Ile Pro Ala Ile Leu Ile Gly Ala Ile Gly Ala Ser Thr Asp<br>   285          290        295 | 915 |
| tgg aac cag act gca tat ggg ctt cca gat ccc aag act aca gaa gag<br>Trp Asn Gln Thr Ala Tyr Gly Leu Pro Asp Pro Lys Thr Thr Glu Glu<br>300         305          310        315 | 963 |

| | | | | | | | | | | | | | | |
|---|---|---|---|---|---|---|---|---|---|---|---|---|---|---|
| gca | gac | atg | att | tta | cca | att | gtt | ctg | cag | tat | ctc | tgc | cct | gtg | tat | 1011
| Ala | Asp | Met | Ile | Leu | Pro | Ile | Val | Leu | Gln | Tyr | Leu | Cys | Pro | Val | Tyr |
| | | | 320 | | | | | 325 | | | | | 330 | | |

```
gca gac atg att tta cca att gtt ctg cag tat ctc tgc cct gtg tat    1011
Ala Asp Met Ile Leu Pro Ile Val Leu Gln Tyr Leu Cys Pro Val Tyr
            320                 325                 330 att tct ttc ttt ggt ctt ggt gca gtt tct gct gct gtt atg tca tca    1059
Ile Ser Phe Phe Gly Leu Gly Ala Val Ser Ala Ala Val Met Ser Ser
            335                 340                 345 gca gat tct tcc atc ttg tca gca agt tcc atg ttt gca cgg aac atc    1107
Ala Asp Ser Ser Ile Leu Ser Ala Ser Ser Met Phe Ala Arg Asn Ile
            350                 355                 360 tac cag ctt tcc ttc aga caa aat gct tcg gac aaa gaa atc gtt tgg    1155
Tyr Gln Leu Ser Phe Arg Gln Asn Ala Ser Asp Lys Glu Ile Val Trp
    365                 370                 375 gtt atg cga atc aca gtg ttt gtg ttt gga gca tct gca aca gcc atg    1203
Val Met Arg Ile Thr Val Phe Val Phe Gly Ala Ser Ala Thr Ala Met
380                 385                 390                 395 gcc ttg ctg acg aaa act gtg tat ggg ctc tgg tac ctc agt tct gac    1251
Ala Leu Leu Thr Lys Thr Val Tyr Gly Leu Trp Tyr Leu Ser Ser Asp
                400                 405                 410 ctt gtt tac atc gtt atc ttc ccc cag ctg ctt tgt gta ctc ttt gtt    1299
Leu Val Tyr Ile Val Ile Phe Pro Gln Leu Leu Cys Val Leu Phe Val
        415                 420                 425 aag gga acc aac acc tat ggg gcc gtg gca ggt tat gtt tct ggc ctc    1347
Lys Gly Thr Asn Thr Tyr Gly Ala Val Ala Gly Tyr Val Ser Gly Leu
            430                 435                 440 ttc ctg aga ata act gga ggg gag cca tat ctg tat ctt cag ccc ttg    1395
Phe Leu Arg Ile Thr Gly Gly Glu Pro Tyr Leu Tyr Leu Gln Pro Leu
            445                 450                 455 atc ttc tac cct ggc tat tac cct gat gat aat ggt ata tat aat cag    1443
Ile Phe Tyr Pro Gly Tyr Tyr Pro Asp Asp Asn Gly Ile Tyr Asn Gln
460                 465                 470                 475 aaa ttt cca ttt aaa aca ctt gcc atg gtt aca tca ttc tta acc aac    1491
Lys Phe Pro Phe Lys Thr Leu Ala Met Val Thr Ser Phe Leu Thr Asn
                480                 485                 490 att tgc atc tcc tat cta gcc aag tat cta ttt gaa agt gga acc ttg    1539
Ile Cys Ile Ser Tyr Leu Ala Lys Tyr Leu Phe Glu Ser Gly Thr Leu
            495                 500                 505 cca cct aaa tta gat gta ttt gat gct gtt gtt gca aga cac agt gaa    1587
Pro Pro Lys Leu Asp Val Phe Asp Ala Val Val Ala Arg His Ser Glu
            510                 515                 520 gaa aac atg gat aag aca att ctt gtc aaa aat gaa aat att aaa tta    1635
Glu Asn Met Asp Lys Thr Ile Leu Val Lys Asn Glu Asn Ile Lys Leu
    525                 530                 535 gat gaa ctt gca ctt gtg aag cca cga cag agc atg acc ctc agc tca    1683
Asp Glu Leu Ala Leu Val Lys Pro Arg Gln Ser Met Thr Leu Ser Ser
540                 545                 550                 555 act ttc acc aat aaa gag gcc ttc ctt gat gtt gat tcc agt cca gaa    1731
Thr Phe Thr Asn Lys Glu Ala Phe Leu Asp Val Asp Ser Ser Pro Glu
                560                 565                 570 ggg tct ggg act gaa gat aat tta cag tga ccccatctaa ataaaatact      1781
Gly Ser Gly Thr Glu Asp Asn Leu Gln
            575                 580 gcttttgcaa acagaacact gtaatagggt ag                                1813
```

<210> SEQ ID NO 10
<211> LENGTH: 580
<212> TYPE: PRT
<213> ORGANISM: Homo sapiens
<400> SEQUENCE: 10

-continued

```
Met Ala Phe His Val Glu Gly Leu Ile Ala Ile Ile Val Phe Tyr Leu
 1               5                  10                  15

Leu Ile Leu Leu Val Gly Ile Trp Ala Trp Arg Thr Lys Asn Ser
             20                  25                  30

Gly Ser Ala Glu Glu Arg Ser Glu Ala Ile Ile Val Gly Gly Arg Asp
             35                  40                  45

Ile Gly Leu Leu Val Gly Gly Phe Thr Met Thr Ala Thr Trp Val Gly
 50                  55                  60

Gly Gly Tyr Ile Asn Gly Thr Ala Glu Ala Val Tyr Val Pro Gly Tyr
 65                  70                  75                  80

Gly Leu Ala Trp Ala Gln Ala Pro Ile Gly Tyr Ser Leu Ser Leu Ile
                 85                  90                  95

Leu Gly Gly Leu Phe Phe Ala Lys Pro Met Arg Ser Lys Gly Tyr Val
             100                 105                 110

Thr Met Leu Asp Pro Phe Gln Gln Ile Tyr Gly Lys Arg Met Gly Gly
             115                 120                 125

Leu Leu Phe Ile Pro Ala Leu Met Gly Glu Met Phe Trp Ala Ala Ala
     130                 135                 140

Ile Phe Ser Ala Leu Gly Ala Thr Ile Ser Val Ile Ile Asp Val Asp
145                 150                 155                 160

Met His Ile Ser Val Ile Ile Ser Ala Leu Ile Ala Thr Leu Tyr Thr
                 165                 170                 175

Leu Val Gly Gly Leu Tyr Ser Val Ala Tyr Thr Asp Val Val Gln Leu
             180                 185                 190

Phe Cys Ile Phe Val Gly Leu Trp Ile Ser Val Pro Phe Ala Leu Ser
             195                 200                 205

His Pro Ala Val Ala Asp Ile Gly Phe Thr Ala Val His Ala Lys Tyr
     210                 215                 220

Gln Lys Pro Trp Leu Gly Thr Val Asp Ser Ser Glu Val Tyr Ser Trp
225                 230                 235                 240

Leu Asp Ser Phe Leu Leu Leu Met Leu Gly Gly Ile Pro Trp Gln Ala
                 245                 250                 255

Tyr Phe Gln Arg Val Leu Ser Ser Ser Ala Thr Tyr Ala Gln Val
             260                 265                 270

Leu Ser Phe Leu Ala Ala Phe Gly Cys Leu Val Met Ala Ile Pro Ala
     275                 280                 285

Ile Leu Ile Gly Ala Ile Gly Ala Ser Thr Asp Trp Asn Gln Thr Ala
290                 295                 300

Tyr Gly Leu Pro Asp Pro Lys Thr Thr Glu Glu Ala Asp Met Ile Leu
305                 310                 315                 320

Pro Ile Val Leu Gln Tyr Leu Cys Pro Val Tyr Ile Ser Phe Phe Gly
                 325                 330                 335

Leu Gly Ala Val Ser Ala Ala Val Met Ser Ser Ala Asp Ser Ser Ile
             340                 345                 350

Leu Ser Ala Ser Ser Met Phe Ala Arg Asn Ile Tyr Gln Leu Ser Phe
     355                 360                 365

Arg Gln Asn Ala Ser Asp Lys Glu Ile Val Trp Val Met Arg Ile Thr
370                 375                 380

Val Phe Val Phe Gly Ala Ser Ala Thr Ala Met Ala Leu Leu Thr Lys
385                 390                 395                 400

Thr Val Tyr Gly Leu Trp Tyr Leu Ser Ser Asp Leu Val Tyr Ile Val
                 405                 410                 415

Ile Phe Pro Gln Leu Leu Cys Val Leu Phe Val Lys Gly Thr Asn Thr
```

-continued

```
                420                 425                 430
Tyr Gly Ala Val Ala Gly Tyr Val Ser Gly Leu Phe Leu Arg Ile Thr
            435                 440                 445
Gly Gly Glu Pro Tyr Leu Tyr Leu Gln Pro Leu Ile Phe Tyr Pro Gly
        450                 455                 460
Tyr Tyr Pro Asp Asp Asn Gly Ile Tyr Asn Gln Lys Phe Pro Phe Lys
465                 470                 475                 480
Thr Leu Ala Met Val Thr Ser Phe Leu Thr Asn Ile Cys Ile Ser Tyr
                485                 490                 495
Leu Ala Lys Tyr Leu Phe Glu Ser Gly Thr Leu Pro Pro Lys Leu Asp
            500                 505                 510
Val Phe Asp Ala Val Ala Arg His Ser Glu Glu Asn Met Asp Lys
        515                 520                 525
Thr Ile Leu Val Lys Asn Glu Asn Ile Lys Leu Asp Glu Leu Ala Leu
        530                 535                 540
Val Lys Pro Arg Gln Ser Met Thr Leu Ser Ser Thr Phe Thr Asn Lys
545                 550                 555                 560
Glu Ala Phe Leu Asp Val Asp Ser Ser Pro Glu Gly Ser Gly Thr Glu
                565                 570                 575
Asp Asn Leu Gln
            580

<210> SEQ ID NO 11
<211> LENGTH: 580
<212> TYPE: PRT
<213> ORGANISM: Homo sapiens

<400> SEQUENCE: 11

Met Ala Phe His Val Glu Gly Leu Ile Ala Ile Ile Val Phe Tyr Leu
 1               5                  10                  15
Leu Ile Leu Leu Val Gly Ile Trp Ala Ala Trp Arg Thr Lys Asn Ser
            20                  25                  30
Gly Ser Ala Glu Glu Arg Ser Glu Ala Ile Ile Val Gly Gly Arg Asp
        35                  40                  45
Ile Gly Leu Leu Val Gly Gly Phe Thr Met Thr Ala Thr Trp Val Gly
    50                  55                  60
Gly Gly Tyr Ile Asn Gly Thr Ala Glu Ala Val Tyr Val Pro Gly Tyr
65                  70                  75                  80
Gly Leu Ala Trp Ala Gln Ala Pro Ile Gly Tyr Ser Leu Ser Leu Ile
                85                  90                  95
Leu Gly Gly Leu Phe Phe Ala Lys Pro Met Arg Ser Lys Gly Tyr Val
            100                 105                 110
Thr Met Leu Asp Pro Phe Gln Gln Ile Tyr Gly Lys Arg Met Gly Gly
        115                 120                 125
Leu Leu Phe Ile Pro Ala Leu Met Gly Glu Met Phe Trp Ala Ala Ala
    130                 135                 140
Ile Phe Ser Ala Leu Gly Ala Thr Ile Ser Val Ile Asp Val Asp
145                 150                 155                 160
Met His Ile Ser Val Ile Ile Ser Ala Leu Ile Ala Thr Leu Tyr Thr
                165                 170                 175
Leu Val Gly Gly Leu Tyr Ser Val Ala Tyr Thr Asp Val Val Gln Leu
            180                 185                 190
Phe Cys Ile Phe Val Gly Leu Trp Ile Ser Val Pro Phe Ala Leu Ser
        195                 200                 205
```

-continued

```
His Pro Ala Val Ala Asp Ile Gly Phe Thr Ala Val His Ala Lys Tyr
    210                 215                 220
Gln Lys Pro Trp Leu Gly Thr Val Asp Ser Ser Glu Val Tyr Ser Trp
225                 230                 235                 240
Leu Asp Ser Phe Leu Leu Met Leu Gly Gly Ile Pro Trp Gln Ala
                245                 250                 255
Tyr Phe Gln Arg Val Leu Ser Ser Ser Ala Thr Tyr Ala Gln Val
            260                 265                 270
Leu Ser Phe Leu Ala Ala Phe Gly Cys Leu Val Met Ala Ile Pro Ala
        275                 280                 285
Ile Leu Ile Gly Ala Ile Gly Ala Ser Thr Asp Trp Asn Gln Thr Ala
    290                 295                 300
Tyr Gly Leu Pro Asp Pro Lys Thr Thr Glu Glu Ala Asp Met Ile Leu
305                 310                 315                 320
Pro Ile Val Leu Gln Tyr Leu Cys Pro Val Tyr Ile Ser Phe Phe Gly
                325                 330                 335
Leu Gly Ala Val Ser Ala Ala Val Met Ser Ser Ala Asp Ser Ser Ile
                340                 345                 350
Leu Ser Ala Ser Ser Met Phe Ala Arg Asn Ile Tyr Gln Leu Ser Phe
            355                 360                 365
Arg Gln Asn Ala Ser Asp Lys Glu Ile Val Trp Val Met Arg Ile Thr
    370                 375                 380
Val Phe Val Phe Gly Ala Ser Ala Thr Ala Met Ala Leu Leu Thr Lys
385                 390                 395                 400
Thr Val Tyr Gly Leu Trp Tyr Leu Ser Ser Asp Leu Val Tyr Ile Val
                405                 410                 415
Ile Phe Pro Gln Leu Leu Cys Val Leu Phe Val Lys Gly Thr Asn Thr
            420                 425                 430
Tyr Gly Ala Val Ala Gly Tyr Val Ser Gly Leu Phe Leu Arg Ile Thr
        435                 440                 445
Gly Gly Glu Pro Tyr Leu Tyr Leu Gln Pro Leu Ile Phe Tyr Pro Gly
    450                 455                 460
Tyr Tyr Pro Asp Asp Asn Gly Ile Tyr Asn Gln Lys Phe Pro Phe Lys
465                 470                 475                 480
Thr Leu Ala Met Val Thr Ser Phe Leu Thr Asn Ile Cys Ile Ser Tyr
                485                 490                 495
Leu Ala Lys Tyr Leu Phe Glu Ser Gly Thr Leu Pro Pro Lys Leu Asp
            500                 505                 510
Val Phe Asp Ala Val Val Ala Arg His Ser Glu Glu Asn Met Asp Lys
        515                 520                 525
Thr Ile Leu Val Lys Asn Glu Asn Ile Lys Leu Asp Glu Leu Ala Leu
    530                 535                 540
Val Lys Pro Arg Gln Ser Met Thr Leu Ser Ser Thr Phe Thr Asn Lys
545                 550                 555                 560
Glu Ala Phe Leu Asp Val Asp Ser Ser Pro Glu Gly Ser Gly Thr Glu
                565                 570                 575
Asp Asn Leu Gln
            580
```

<210> SEQ ID NO 12
<211> LENGTH: 580
<212> TYPE: PRT
<213> ORGANISM: Homo sapiens

<400> SEQUENCE: 12

-continued

```
Met Ala Phe His Val Glu Gly Leu Ile Ala Ile Ile Val Phe Tyr Leu
 1               5                  10                  15

Leu Ile Leu Leu Val Gly Ile Trp Ala Ala Trp Arg Thr Lys Asn Ser
            20                  25                  30

Gly Ser Ala Glu Glu Arg Ser Glu Ala Ile Ile Val Gly Gly Arg Asp
            35                  40                  45

Ile Gly Leu Leu Val Gly Gly Phe Thr Met Thr Ala Thr Trp Val Gly
        50                  55                  60

Gly Gly Tyr Ile Asn Gly Thr Ala Glu Ala Val Tyr Val Pro Gly Tyr
 65              70                  75                  80

Gly Leu Ala Trp Ala Gln Ala Pro Ile Gly Tyr Ser Leu Ser Leu Ile
                85                  90                  95

Leu Gly Gly Leu Phe Phe Ala Lys Pro Met Arg Ser Lys Gly Tyr Val
                100                 105                 110

Thr Met Leu Asp Pro Phe Gln Gln Ile Tyr Gly Lys Arg Met Gly Gly
            115                 120                 125

Leu Leu Phe Ile Pro Ala Leu Met Gly Glu Met Phe Trp Ala Ala Ala
130                 135                 140

Ile Phe Ser Ala Leu Gly Ala Thr Ile Ser Val Ile Ile Asp Val Asp
145                 150                 155                 160

Met His Ile Ser Val Ile Ser Ala Leu Ile Ala Thr Leu Tyr Thr
                165                 170                 175

Leu Val Gly Gly Leu Tyr Ser Val Ala Tyr Thr Asp Val Val Gln Leu
                180                 185                 190

Phe Cys Ile Phe Val Gly Leu Trp Ile Ser Val Pro Phe Ala Leu Ser
            195                 200                 205

His Pro Ala Val Ala Asp Ile Gly Phe Thr Ala Val His Ala Lys Tyr
            210                 215                 220

Gln Lys Pro Trp Leu Gly Thr Val Asp Ser Ser Glu Val Tyr Ser Trp
225                 230                 235                 240

Leu Asp Ser Phe Leu Leu Leu Met Leu Gly Gly Ile Pro Trp Gln Ala
                245                 250                 255

Tyr Phe Gln Arg Val Leu Ser Ser Ser Ala Thr Tyr Ala Gln Val
            260                 265                 270

Leu Ser Phe Leu Ala Ala Phe Gly Cys Leu Val Met Ala Ile Pro Ala
        275                 280                 285

Ile Leu Ile Gly Ala Ile Gly Ala Ser Thr Asp Trp Asn Gln Thr Ala
        290                 295                 300

Tyr Gly Leu Pro Asp Pro Lys Thr Thr Glu Glu Ala Asp Met Ile Leu
305                 310                 315                 320

Pro Ile Val Leu Gln Tyr Leu Cys Pro Val Tyr Ile Ser Phe Phe Gly
                325                 330                 335

Leu Gly Ala Val Ser Ala Ala Val Met Ser Ser Ala Asp Ser Ser Ile
                340                 345                 350

Leu Ser Ala Ser Ser Met Phe Ala Arg Asn Ile Tyr Gln Leu Ser Phe
            355                 360                 365

Arg Gln Asn Ala Ser Asp Lys Glu Ile Val Trp Val Met Arg Ile Thr
370                 375                 380

Val Phe Val Phe Gly Ala Ser Ala Thr Ala Met Ala Leu Leu Thr Lys
385                 390                 395                 400

Thr Val Tyr Gly Leu Trp Tyr Leu Ser Ser Asp Leu Val Tyr Ile Val
                405                 410                 415
```

```
Ile Phe Pro Gln Leu Leu Cys Val Leu Phe Val Lys Gly Thr Asn Thr
                420                 425                 430

Tyr Gly Ala Val Ala Gly Tyr Val Ser Gly Leu Phe Leu Arg Ile Thr
            435                 440                 445

Gly Gly Glu Pro Tyr Leu Tyr Leu Gln Pro Leu Ile Phe Tyr Pro Gly
        450                 455                 460

Tyr Tyr Pro Asp Asp Asn Gly Ile Tyr Asn Gln Lys Phe Pro Phe Lys
465                 470                 475                 480

Thr Leu Ala Met Val Thr Ser Phe Leu Thr Asn Ile Cys Ile Ser Tyr
                485                 490                 495

Leu Ala Lys Tyr Leu Phe Glu Ser Gly Thr Leu Pro Pro Lys Leu Asp
            500                 505                 510

Val Phe Asp Ala Val Ala Arg His Ser Glu Glu Asn Met Asp Lys
        515                 520                 525

Thr Ile Leu Val Lys Asn Glu Asn Ile Lys Leu Asp Glu Leu Ala Leu
    530                 535                 540

Val Lys Pro Arg Gln Ser Met Thr Leu Ser Ser Thr Phe Thr Asn Lys
545                 550                 555                 560

Glu Ala Phe Leu Asp Val Asp Ser Ser Pro Gly Ser Gly Thr Glu
                565                 570                 575

Asp Asn Leu Gln
            580

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ataaaaatgg ctttccatgt ggaaggactg                                      30

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
tcactgtaaa ttatcttcca gtcccagacc c                                    31

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gctgcatacc atctctcc                                                   18

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
```

Primer

<400> SEQUENCE: 16
ctgtgtatgg gctctggtac c                                                 21

<210> SEQ ID NO 17
<211> LENGTH: 379
<212> TYPE: DNA
<213> ORGANISM: Homo sapiens
<220> FEATURE:
<221> NAME/KEY: modified_base
<222> LOCATION: (12)..(364)
<223> OTHER INFORMATION: N = A, T, C, or G

<400> SEQUENCE: 17
agctccgaag tnctatcact catttncagc aaaagttaaa ataaattaat gtatacaagg        60
cctcagccca gcgttggcaa attgacgtgt tcgataaatg tnagcttta actactattt      120 cattagtagt agtagtaata aatgtcttct ggaaccccag tagccagtta tccttgagta      180
acagtgattt acatctcctg ctttctcctt ttggtgcatt taaaagtctt ccctcaatac      240
aacantgaca acacacacac acacacacac acacacacac acacacacac acaatgcaaa      300
actgggcaaa gcagatattt ctcccacaaa tggccaataa gcatgnggaa gntgctcaac      360
atcnttagga cattagggg                                                   379

<210> SEQ ID NO 18
<211> LENGTH: 300
<212> TYPE: DNA
<213> ORGANISM: Homo sapiens

<400> SEQUENCE: 18
ccctattgtg aactgtgcat gcaagggacc taggttgtgc actcgttatg agaatgtaac       60
taatgcctga tgatctgaga tggaacagtt tcatcccaaa accgtcacac acacacacac      120
acacacacac acacacacac acaggtttgt ggaaaagttg tcttccacaa agccaatcca      180
ggttggggac tactgatata gaaagaaatg tctgatcttt aaggcccana gtgattattt      240
ntcncttttg ttaactgtct tacttgcctt aacctccatc aggtttccca cagcacagct      300

<210> SEQ ID NO 19
<211> LENGTH: 343
<212> TYPE: DNA
<213> ORGANISM: Homo sapiens

<400> SEQUENCE: 19
gatcgcacca ctncactcca gcctgggcaa caaggtgagg ctctgtctca ctctcacaca       60
cacacacaca cacacacaca cacacacaca cacacacaca cacaaatata cataacaaac      120
aagaaatgta taaattaaag aaaaagagaa aattttttaa agcacccaca atctagctgt      180
catgctctgg tagttgtctt ccagccttgt ctctgtgcat agatttataa gattttttaa      240
aatacagtga tattagtgta cttgccatct ggtatcctgc ttcattttta gagccaacac      300
ttttctattg aattagtctt cataaaaacc cattttattt tat                        343

<210> SEQ ID NO 20
<211> LENGTH: 1743
<212> TYPE: DNA
<213> ORGANISM: Mus musculus
<220> FEATURE:
<221> NAME/KEY: CDS
<222> LOCATION: (1)..(1743)

-continued

```
<400> SEQUENCE: 20 atg cct ttc cat gtg gaa gga ctg gta gct att atc ctc ttc tac ctc      48
Met Pro Phe His Val Glu Gly Leu Val Ala Ile Ile Leu Phe Tyr Leu
 1               5                  10                  15 ctt ata ttt ctg gtt gga ata tgg gct gca tgg aaa acc aaa aac agc      96
Leu Ile Phe Leu Val Gly Ile Trp Ala Ala Trp Lys Thr Lys Asn Ser
             20                  25                  30 ggc aac cca gaa gag cgc agt gaa gcc atc ata gtc ggg ggc cgt gac     144
Gly Asn Pro Glu Glu Arg Ser Glu Ala Ile Ile Val Gly Gly Arg Asp
         35                  40                  45 att ggt ttg ttg gtt ggt ggt ttt acc atg aca gcc acc tgg gtt gga     192
Ile Gly Leu Leu Val Gly Gly Phe Thr Met Thr Ala Thr Trp Val Gly
 50                  55                  60 gga ggc tac atc aat ggg aca gca gaa gca gtg tat ggg cca ggt tgt     240
Gly Gly Tyr Ile Asn Gly Thr Ala Glu Ala Val Tyr Gly Pro Gly Cys
 65                  70                  75                  80 ggt cta gct tgg gct cat gca ccc att gga tat tct ctg agt cta att     288
Gly Leu Ala Trp Ala His Ala Pro Ile Gly Tyr Ser Leu Ser Leu Ile
                 85                  90                  95 tta ggt ggt ctg ttt ttt gcg aaa cct atg cgt tcc aag gga tat gtg     336
Leu Gly Gly Leu Phe Phe Ala Lys Pro Met Arg Ser Lys Gly Tyr Val
            100                 105                 110 act atg tta gac cca ttc aaa cag atc tat gga aag cgc atg ggt ggg     384
Thr Met Leu Asp Pro Phe Lys Gln Ile Tyr Gly Lys Arg Met Gly Gly
        115                 120                 125 ctg ctc ttc atc cct gca ctg atg gga gag atg ttc tgg gct gca gca     432
Leu Leu Phe Ile Pro Ala Leu Met Gly Glu Met Phe Trp Ala Ala Ala
    130                 135                 140 att ttc tct gca tta ggg gcc acc atc agc gtg atc att gat gtg gat     480
Ile Phe Ser Ala Leu Gly Ala Thr Ile Ser Val Ile Ile Asp Val Asp
145                 150                 155                 160 gtg aac ata tcg gtc att gtc tct gca ctc att gcc att ctt tat acc     528
Val Asn Ile Ser Val Ile Val Ser Ala Leu Ile Ala Ile Leu Tyr Thr
                165                 170                 175 cta gtg ggt ggg ctc tac tct gtg gca tat act gat gtt gtc cag cta     576
Leu Val Gly Gly Leu Tyr Ser Val Ala Tyr Thr Asp Val Val Gln Leu
            180                 185                 190 ttc tgc att ttt ata gga ctg tgg atc agt gtc cct ttt gcc ctg tca     624
Phe Cys Ile Phe Ile Gly Leu Trp Ile Ser Val Pro Phe Ala Leu Ser
        195                 200                 205 cat cct gca gtc acc gac atc gga ttc aca gct gtg cat gct aaa tac     672
His Pro Ala Val Thr Asp Ile Gly Phe Thr Ala Val His Ala Lys Tyr
    210                 215                 220 cag agt ccc tgg ctg gga acc att gaa tca gtt gaa gtc tac acc tgg     720
Gln Ser Pro Trp Leu Gly Thr Ile Glu Ser Val Glu Val Tyr Thr Trp
225                 230                 235                 240 ctt gat aat ttt ctg tta ttg atg ctg ggt gga atc cca tgg caa gcc     768
Leu Asp Asn Phe Leu Leu Leu Met Leu Gly Gly Ile Pro Trp Gln Ala
                245                 250                 255 tac ttc cag agg gtc ctc tct tca tcc gcc acc tat gct cag gta         816
Tyr Phe Gln Arg Val Leu Ser Ser Ser Ala Thr Tyr Ala Gln Val
            260                 265                 270 ctg tcc ttc ctg gca gct ttt ggg tgc ctg gtg atg gct cta ccc gcc     864
Leu Ser Phe Leu Ala Ala Phe Gly Cys Leu Val Met Ala Leu Pro Ala
        275                 280                 285 ata tgc ata gga gct att gga gct tcc aca gac tgg aac cag act gcc     912
Ile Cys Ile Gly Ala Ile Gly Ala Ser Thr Asp Trp Asn Gln Thr Ala
    290                 295                 300 tac ggg tat cca gat ccc aag act aag gag gaa gca gac atg att ctc     960
```

```
Tyr Gly Tyr Pro Asp Pro Lys Thr Lys Glu Ala Asp Met Ile Leu
305                 310                 315                 320 ccg atc gtt ctg cag tac ctc tgc cct gtg tac atc tcc ttc ttt ggg      1008
Pro Ile Val Leu Gln Tyr Leu Cys Pro Val Tyr Ile Ser Phe Phe Gly
                325                 330                 335 ctt ggt gct gtt tca gct gct gtc atg tcc tca gct gac tcg tcc atc      1056
Leu Gly Ala Val Ser Ala Ala Val Met Ser Ser Ala Asp Ser Ser Ile
                340                 345                 350 ctg tcg gcg agt tct atg ttt gct cgg aat atc tac cag ctt tcc ttc      1104
Leu Ser Ala Ser Ser Met Phe Ala Arg Asn Ile Tyr Gln Leu Ser Phe
            355                 360                 365 aga caa aat gca tca gac aag gaa att gtg tgg gtc atg agg atc act      1152
Arg Gln Asn Ala Ser Asp Lys Glu Ile Val Trp Val Met Arg Ile Thr
370                 375                 380 gtg ctt gtg ttc gga gca tct gca aca gcc atg gct ttg ctg acg aag      1200
Val Leu Val Phe Gly Ala Ser Ala Thr Ala Met Ala Leu Leu Thr Lys
385                 390                 395                 400 act gtg tat ggg ctc tgg tac ctg agc tct gac ctt gtc tac atc atc      1248
Thr Val Tyr Gly Leu Trp Tyr Leu Ser Ser Asp Leu Val Tyr Ile Ile
                405                 410                 415 atc ttc cca cag ctg ctc tgt gta ctc ttc atc aaa gga acc aac act      1296
Ile Phe Pro Gln Leu Leu Cys Val Leu Phe Ile Lys Gly Thr Asn Thr
                420                 425                 430 tat ggg gca gtt gct ggt tat att ttt gga cta ttc ctg aga att act      1344
Tyr Gly Ala Val Ala Gly Tyr Ile Phe Gly Leu Phe Leu Arg Ile Thr
            435                 440                 445 gga gga gag cca tat cta tac ttg cag ccc tta atc ttc tac cct ggt      1392
Gly Gly Glu Pro Tyr Leu Tyr Leu Gln Pro Leu Ile Phe Tyr Pro Gly
450                 455                 460 tat tac tct gac aag aat ggt ata tac aat cag agg ttc cca ttt aaa      1440
Tyr Tyr Ser Asp Lys Asn Gly Ile Tyr Asn Gln Arg Phe Pro Phe Lys
465                 470                 475                 480 act ctc tcc atg gtt acc tca ttc ttt acc aac att tgt gtt tct tat      1488
Thr Leu Ser Met Val Thr Ser Phe Phe Thr Asn Ile Cys Val Ser Tyr
                485                 490                 495 cta gcc aag tat cta ttt gaa agt gga acc ttg cct cca aaa tta gat      1536
Leu Ala Lys Tyr Leu Phe Glu Ser Gly Thr Leu Pro Pro Lys Leu Asp
                500                 505                 510 gta ttt gat gct gtt gtc gca agg cac agt gaa gag aac atg gac aag      1584
Val Phe Asp Ala Val Val Ala Arg His Ser Glu Glu Asn Met Asp Lys
            515                 520                 525 acc att cta gtc aga aat gaa aat atc aaa tta aat gaa ctt gca cct      1632
Thr Ile Leu Val Arg Asn Glu Asn Ile Lys Leu Asn Glu Leu Ala Pro
530                 535                 540 gtg aaa cct cgg cag agc cta acc ctc agt tca act ttc acc aat aag      1680
Val Lys Pro Arg Gln Ser Leu Thr Leu Ser Ser Thr Phe Thr Asn Lys
545                 550                 555                 560 gag gcc ctc ctt gat gtt gat tcc agt ccg gag ggg tct ggg act gaa      1728
Glu Ala Leu Leu Asp Val Asp Ser Ser Pro Glu Gly Ser Gly Thr Glu
                565                 570                 575 gat aat tta caa tga                                                   1743
Asp Asn Leu Gln
            580

<210> SEQ ID NO 21
<211> LENGTH: 580
<212> TYPE: PRT
<213> ORGANISM: Mus musculus

<400> SEQUENCE: 21
```

-continued

```
Met Pro Phe His Val Glu Gly Leu Val Ala Ile Ile Leu Phe Tyr Leu
 1               5                  10                  15

Leu Ile Phe Leu Val Gly Ile Trp Ala Trp Lys Thr Lys Asn Ser
             20                  25                  30

Gly Asn Pro Glu Glu Arg Ser Glu Ala Ile Ile Val Gly Gly Arg Asp
             35                  40                  45

Ile Gly Leu Leu Val Gly Gly Phe Thr Met Thr Ala Thr Trp Val Gly
     50                  55                  60

Gly Gly Tyr Ile Asn Gly Thr Ala Glu Ala Val Tyr Gly Pro Gly Cys
 65                  70                  75                  80

Gly Leu Ala Trp Ala His Ala Pro Ile Gly Tyr Ser Leu Ser Leu Ile
                 85                  90                  95

Leu Gly Gly Leu Phe Phe Ala Lys Pro Met Arg Ser Lys Gly Tyr Val
             100                 105                 110

Thr Met Leu Asp Pro Phe Lys Gln Ile Tyr Gly Lys Arg Met Gly Gly
             115                 120                 125

Leu Leu Phe Ile Pro Ala Leu Met Gly Glu Met Phe Trp Ala Ala Ala
     130                 135                 140

Ile Phe Ser Ala Leu Gly Ala Thr Ile Ser Val Ile Ile Asp Val Asp
145                 150                 155                 160

Val Asn Ile Ser Val Ile Val Ser Ala Leu Ile Ala Ile Leu Tyr Thr
                 165                 170                 175

Leu Val Gly Gly Leu Tyr Ser Val Ala Tyr Thr Asp Val Val Gln Leu
             180                 185                 190

Phe Cys Ile Phe Ile Gly Leu Trp Ile Ser Val Pro Phe Ala Leu Ser
     195                 200                 205

His Pro Ala Val Thr Asp Ile Gly Phe Thr Ala Val His Ala Lys Tyr
     210                 215                 220

Gln Ser Pro Trp Leu Gly Thr Ile Glu Ser Val Glu Val Tyr Thr Trp
225                 230                 235                 240

Leu Asp Asn Phe Leu Leu Leu Met Leu Gly Gly Ile Pro Trp Gln Ala
             245                 250                 255

Tyr Phe Gln Arg Val Leu Ser Ser Ser Ala Thr Tyr Ala Gln Val
             260                 265                 270

Leu Ser Phe Leu Ala Ala Phe Gly Cys Leu Val Met Ala Leu Pro Ala
     275                 280                 285

Ile Cys Ile Gly Ala Ile Gly Ala Ser Thr Asp Trp Asn Gln Thr Ala
     290                 295                 300

Tyr Gly Tyr Pro Asp Pro Lys Thr Lys Glu Glu Ala Asp Met Ile Leu
305                 310                 315                 320

Pro Ile Val Leu Gln Tyr Leu Cys Pro Val Tyr Ile Ser Phe Phe Gly
             325                 330                 335

Leu Gly Ala Val Ser Ala Ala Val Met Ser Ser Ala Asp Ser Ser Ile
             340                 345                 350

Leu Ser Ala Ser Ser Met Phe Ala Arg Asn Ile Tyr Gln Leu Ser Phe
     355                 360                 365

Arg Gln Asn Ala Ser Asp Lys Glu Ile Val Trp Val Met Arg Ile Thr
     370                 375                 380

Val Leu Val Phe Gly Ala Ser Ala Thr Ala Met Ala Leu Leu Thr Lys
385                 390                 395                 400

Thr Val Tyr Gly Leu Trp Tyr Leu Ser Ser Asp Leu Val Tyr Ile Ile
                 405                 410                 415

Ile Phe Pro Gln Leu Leu Cys Val Leu Phe Ile Lys Gly Thr Asn Thr
```

-continued

```
                420             425             430
Tyr Gly Ala Val Ala Gly Tyr Ile Phe Gly Leu Phe Leu Arg Ile Thr
            435                 440                 445
Gly Gly Glu Pro Tyr Leu Tyr Leu Gln Pro Leu Ile Phe Tyr Pro Gly
        450                 455                 460
Tyr Tyr Ser Asp Lys Asn Gly Ile Tyr Asn Gln Arg Phe Pro Phe Lys
465                 470                 475                 480
Thr Leu Ser Met Val Thr Ser Phe Phe Thr Asn Ile Cys Val Ser Tyr
                485                 490                 495
Leu Ala Lys Tyr Leu Phe Glu Ser Gly Thr Leu Pro Pro Lys Leu Asp
            500                 505                 510
Val Phe Asp Ala Val Ala Arg His Ser Glu Glu Asn Met Asp Lys
        515                 520                 525
Thr Ile Leu Val Arg Asn Glu Asn Ile Lys Leu Asn Glu Leu Ala Pro
    530                 535                 540
Val Lys Pro Arg Gln Ser Leu Thr Leu Ser Ser Thr Phe Thr Asn Lys
545                 550                 555                 560
Glu Ala Leu Leu Asp Val Asp Ser Ser Pro Glu Gly Ser Gly Thr Glu
                565                 570                 575
Asp Asn Leu Gln
            580
```

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

```
Val Asp Ser Ser Pro Glu Gly Ser Gly Thr Glu Asp Asn Leu Gln
  1               5                  10                  15
```

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
ctggatccaa aatggccttt ccatgtagga agg                                   33

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
gactcgaggt cacttgtaaa gttatcttca gtccc                                 35

<210> SEQ ID NO 25
<211> LENGTH: 580
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 25

| | | | | | | | | | | | | | | |
|---|---|---|---|---|---|---|---|---|---|---|---|---|---|---|
| Met | Ser | Phe | His | Val | Glu | Gly | Leu | Val | Ala | Ile | Ile | Leu | Phe | Tyr | Leu |
| 1 | | | | 5 | | | | | 10 | | | | | 15 | |

| Leu | Ile | Phe | Leu | Val | Gly | Ile | Trp | Ala | Ala | Trp | Lys | Thr | Lys | Asn | Ser |
| 20 | | | | | 25 | | | | | 30 | | | | | |

| Gly | Asn | Pro | Glu | Glu | Arg | Ser | Glu | Ala | Ile | Ile | Val | Gly | Gly | Arg | Asp |
| | | 35 | | | | | 40 | | | | | 45 | | | |

| Ile | Gly | Leu | Leu | Val | Gly | Gly | Phe | Thr | Met | Thr | Ala | Thr | Trp | Val | Gly |
| | 50 | | | | | 55 | | | | | 60 | | | | |

| Gly | Gly | Tyr | Ile | Asn | Gly | Thr | Ala | Glu | Ala | Val | Tyr | Gly | Pro | Gly | Cys |
| 65 | | | | | 70 | | | | | 75 | | | | | 80 |

| Gly | Leu | Ala | Trp | Ala | His | Ala | Pro | Ile | Gly | Tyr | Ser | Leu | Ser | Leu | Ile |
| | | | | 85 | | | | | 90 | | | | | 95 | |

| Leu | Gly | Gly | Leu | Phe | Phe | Ala | Lys | Pro | Met | Arg | Ser | Lys | Gly | Tyr | Val |
| | | | 100 | | | | | 105 | | | | | 110 | | |

| Thr | Met | Leu | Asp | Pro | Phe | Lys | Gln | Ile | Tyr | Gly | Lys | Arg | Met | Gly | Gly |
| | | 115 | | | | | 120 | | | | | 125 | | | |

| Leu | Leu | Phe | Ile | Pro | Ala | Leu | Met | Gly | Glu | Met | Phe | Trp | Ala | Ala | Ala |
| | 130 | | | | | 135 | | | | | 140 | | | | |

| Ile | Phe | Ser | Ala | Leu | Gly | Ala | Thr | Ile | Ser | Val | Ile | Ile | Asp | Val | Asp |
| 145 | | | | | 150 | | | | | 155 | | | | | 160 |

| Val | Asn | Ile | Ser | Val | Ile | Val | Ser | Ala | Leu | Ile | Ala | Ile | Leu | Tyr | Thr |
| | | | | 165 | | | | | 170 | | | | | 175 | |

| Leu | Val | Gly | Gly | Leu | Tyr | Ser | Val | Ala | Tyr | Thr | Asp | Val | Val | Gln | Leu |
| | | | 180 | | | | | 185 | | | | | 190 | | |

| Phe | Cys | Ile | Phe | Ile | Gly | Leu | Trp | Ile | Ser | Val | Pro | Phe | Ala | Leu | Ser |
| | | 195 | | | | | 200 | | | | | 205 | | | |

| His | Pro | Ala | Val | Thr | Asp | Ile | Gly | Phe | Thr | Ala | Val | His | Ala | Lys | Tyr |
| | 210 | | | | | 215 | | | | | 220 | | | | |

| Gln | Ser | Pro | Trp | Leu | Gly | Thr | Ile | Glu | Ser | Val | Glu | Val | Tyr | Thr | Trp |
| 225 | | | | | 230 | | | | | 235 | | | | | 240 |

| Leu | Asp | Asn | Phe | Leu | Leu | Leu | Met | Leu | Gly | Gly | Ile | Pro | Trp | Gln | Ala |
| | | | | 245 | | | | | 250 | | | | | 255 | |

| Tyr | Phe | Gln | Arg | Val | Leu | Ser | Ser | Ser | Ala | Thr | Tyr | Ala | Gln | Val |
| | | | 260 | | | | | 265 | | | | | 270 | | |

| Leu | Ser | Phe | Leu | Ala | Ala | Phe | Gly | Cys | Leu | Val | Met | Ala | Leu | Pro | Ala |
| | | 275 | | | | | 280 | | | | | 285 | | | |

| Ile | Cys | Ile | Gly | Ala | Ile | Gly | Ala | Ser | Thr | Asp | Trp | Asn | Gln | Thr | Ala |
| | 290 | | | | | 295 | | | | | 300 | | | | |

| Tyr | Gly | Tyr | Pro | Asp | Pro | Lys | Thr | Lys | Glu | Glu | Ala | Asp | Met | Ile | Leu |
| 305 | | | | | 310 | | | | | 315 | | | | | 320 |

| Pro | Ile | Val | Leu | Gln | Tyr | Leu | Cys | Pro | Val | Tyr | Ile | Ser | Phe | Phe | Gly |
| | | | | 325 | | | | | 330 | | | | | 335 | |

| Leu | Gly | Ala | Val | Ser | Ala | Ala | Val | Met | Ser | Ser | Ala | Asp | Ser | Ser | Ile |
| | | | 340 | | | | | 345 | | | | | 350 | | |

| Leu | Ser | Ala | Ser | Ser | Met | Phe | Ala | Arg | Asn | Ile | Tyr | Gln | Leu | Ser | Phe |
| | | 355 | | | | | 360 | | | | | 365 | | | |

| Arg | Gln | Asn | Ala | Ser | Asp | Lys | Glu | Ile | Val | Trp | Val | Met | Arg | Ile | Thr |
| | 370 | | | | | 375 | | | | | 380 | | | | |

| Val | Leu | Val | Phe | Gly | Ala | Ser | Ala | Thr | Ala | Met | Ala | Leu | Leu | Thr | Lys |
| 385 | | | | | 390 | | | | | 395 | | | | | 400 |

```
Thr Val Tyr Gly Leu Trp Tyr Leu Ser Ser Asp Leu Val Tyr Ile Ile
                405                 410                 415

Ile Phe Pro Gln Leu Leu Cys Val Leu Phe Ile Lys Gly Thr Asn Thr
            420                 425                 430

Tyr Gly Ala Val Ala Gly Tyr Ile Phe Gly Leu Phe Leu Arg Ile Thr
            435                 440                 445

Gly Gly Glu Pro Tyr Leu Tyr Leu Gln Pro Leu Ile Phe Tyr Pro Gly
450                 455                 460

Tyr Tyr Ser Asp Lys Asn Gly Ile Tyr Asn Gln Arg Phe Pro Phe Lys
465                 470                 475                 480

Thr Leu Ser Met Val Thr Ser Phe Phe Thr Asn Ile Cys Val Ser Tyr
                485                 490                 495

Leu Ala Lys Tyr Leu Phe Glu Ser Gly Thr Leu Pro Pro Lys Leu Asp
                500                 505                 510

Val Phe Asp Ala Val Ala Arg His Ser Glu Glu Asn Met Asp Lys
                515                 520                 525

Thr Ile Leu Val Arg Asn Glu Asn Ile Lys Leu Asn Glu Leu Ala Pro
            530                 535                 540

Val Lys Pro Arg Gln Ser Leu Thr Leu Ser Ser Thr Phe Thr Asn Lys
545                 550                 555                 560

Glu Ala Leu Leu Asp Val Asp Ser Ser Pro Glu Gly Ser Gly Thr Glu
                565                 570                 575

Asp Asn Leu Gln
            580

<210> SEQ ID NO 26
<211> LENGTH: 580
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 26

Met Ala Phe His Val Glu Gly Leu Ile Ala Ile Ile Val Phe Tyr Leu
 1               5                  10                  15

Leu Ile Leu Leu Val Gly Ile Trp Ala Ala Trp Arg Thr Lys Asn Ser
                20                  25                  30

Gly Ser Ala Glu Glu Arg Ser Glu Ala Ile Ile Val Gly Gly Arg Asp
            35                  40                  45

Ile Gly Leu Leu Val Gly Gly Phe Thr Met Thr Ala Thr Trp Val Gly
        50                  55                  60

Gly Gly Tyr Ile Asn Gly Thr Ala Glu Ala Val Tyr Val Pro Gly Tyr
65                  70                  75                  80

Gly Leu Ala Trp Ala Gln Ala Pro Ile Gly Tyr Ser Leu Ser Leu Ile
                85                  90                  95

Leu Gly Gly Leu Phe Phe Ala Lys Pro Met Arg Ser Lys Gly Tyr Val
            100                 105                 110

Thr Met Leu Asp Pro Phe Gln Gln Ile Tyr Gly Lys Arg Met Gly Gly
        115                 120                 125

Leu Leu Phe Ile Pro Ala Leu Met Gly Glu Met Phe Trp Ala Ala Ala
    130                 135                 140

Ile Phe Ser Ala Leu Gly Ala Thr Ile Ser Val Ile Ile Asp Val Asp
145                 150                 155                 160

Met His Ile Ser Val Ile Ile Ser Ala Leu Ile Ala Thr Leu Tyr Thr
                165                 170                 175
```

```
Leu Val Gly Gly Leu Tyr Ser Val Ala Tyr Thr Asp Val Val Gln Leu
            180                 185                 190

Phe Cys Ile Phe Val Gly Leu Trp Ile Ser Val Pro Phe Ala Leu Ser
            195                 200                 205

His Pro Ala Val Ala Asp Ile Gly Phe Thr Ala Val His Ala Lys Tyr
            210                 215                 220

Gln Lys Pro Trp Leu Gly Thr Val Asp Ser Ser Glu Val Tyr Ser Trp
225                 230                 235                 240

Leu Asp Ser Phe Leu Leu Leu Met Leu Gly Gly Ile Pro Trp Gln Ala
                245                 250                 255

Tyr Phe Gln Arg Val Leu Ser Ser Ser Ala Thr Tyr Ala Gln Val
                260                 265                 270

Leu Ser Phe Leu Ala Ala Phe Gly Cys Leu Val Met Ala Ile Pro Ala
            275                 280                 285

Ile Leu Ile Gly Ala Ile Gly Ala Ser Thr Asp Trp Asn Gln Thr Ala
            290                 295                 300

Tyr Gly Leu Pro Asp Pro Lys Thr Thr Glu Glu Ala Asp Met Ile Leu
305                 310                 315                 320

Pro Ile Val Leu Gln Tyr Leu Cys Pro Val Tyr Ile Ser Phe Phe Gly
                325                 330                 335

Leu Gly Ala Val Ser Ala Ala Val Met Ser Ser Ala Asp Ser Ser Ile
            340                 345                 350

Leu Ser Ala Ser Ser Met Phe Ala Arg Asn Ile Tyr Gln Leu Ser Phe
            355                 360                 365

Arg Gln Asn Ala Ser Asp Lys Glu Ile Val Trp Val Met Arg Ile Thr
            370                 375                 380

Val Phe Val Phe Gly Ala Ser Ala Thr Ala Met Ala Leu Leu Thr Lys
385                 390                 395                 400

Thr Val Tyr Gly Leu Trp Tyr Leu Ser Ser Asp Leu Val Tyr Ile Val
                405                 410                 415

Ile Phe Pro Gln Leu Leu Cys Val Leu Phe Val Lys Gly Thr Asn Thr
                420                 425                 430

Tyr Gly Ala Val Ala Gly Tyr Val Ser Gly Leu Phe Leu Arg Ile Thr
            435                 440                 445

Gly Gly Glu Pro Tyr Leu Tyr Leu Gln Pro Leu Ile Phe Tyr Pro Gly
            450                 455                 460

Tyr Tyr Pro Asp Asp Asn Gly Ile Tyr Asn Gln Lys Phe Pro Phe Lys
465                 470                 475                 480

Thr Leu Ala Met Val Thr Ser Phe Leu Thr Asn Ile Cys Ile Ser Tyr
                485                 490                 495

Leu Ala Lys Tyr Leu Phe Glu Ser Gly Thr Leu Pro Pro Lys Leu Asp
            500                 505                 510

Val Phe Asp Ala Val Val Ala Arg His Ser Glu Glu Asn Met Asp Lys
            515                 520                 525

Thr Ile Leu Val Lys Asn Glu Asn Ile Lys Ile Asp Glu Leu Ala Leu
530                 535                 540

Val Lys Pro Arg Gln Ser Met Thr Leu Ser Ser Thr Phe Thr Asn Lys
545                 550                 555                 560

Glu Ala Phe Leu Asp Val Asp Ser Ser Pro Glu Gly Ser Gly Thr Glu
                565                 570                 575

Asp Asn Leu Gln
            580
```

```
<210> SEQ ID NO 27
<211> LENGTH: 580
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 27

Met Pro Phe His Val Glu Gly Leu Val Ala Ile Ile Leu Phe Tyr Leu
  1               5                  10                  15

Leu Ile Phe Leu Val Gly Ile Trp Ala Ala Trp Lys Thr Lys Asn Ser
             20                  25                  30

Gly Asn Ala Glu Glu Arg Ser Glu Ala Ile Ile Val Gly Gly Arg Asp
         35                  40                  45

Ile Gly Leu Leu Val Gly Gly Phe Thr Met Thr Ala Thr Trp Val Gly
     50                  55                  60

Gly Gly Tyr Ile Asn Gly Thr Ala Glu Ala Val Tyr Gly Pro Gly Cys
 65                  70                  75                  80

Gly Leu Ala Trp Ala Gln Ala Pro Ile Gly Tyr Ser Leu Ser Leu Ile
                 85                  90                  95

Leu Gly Gly Leu Phe Phe Ala Lys Pro Met Arg Ser Lys Gly Tyr Val
            100                 105                 110

Thr Met Leu Asp Pro Phe Gln Gln Ile Tyr Gly Lys Arg Met Gly Gly
        115                 120                 125

Leu Leu Phe Ile Pro Ala Leu Met Gly Glu Met Phe Trp Ala Ala Ala
    130                 135                 140

Ile Phe Ser Ala Leu Gly Ala Thr Ile Ser Val Ile Ile Asp Val Asp
145                 150                 155                 160

Val Asn Ile Ser Val Ile Val Ser Ala Leu Ile Ala Ile Leu Tyr Thr
                165                 170                 175

Leu Val Gly Gly Leu Tyr Ser Val Ala Tyr Thr Asp Val Val Gln Leu
            180                 185                 190

Phe Cys Ile Phe Ile Gly Leu Trp Ile Ser Val Pro Phe Ala Leu Ser
        195                 200                 205

His Pro Ala Val Thr Asp Ile Gly Phe Thr Ala Val His Ala Lys Tyr
    210                 215                 220

Gln Ser Pro Trp Leu Gly Thr Ile Glu Ser Val Glu Val Tyr Thr Trp
225                 230                 235                 240

Leu Asp Asn Phe Leu Leu Leu Met Leu Gly Gly Ile Pro Trp Gln Ala
                245                 250                 255

Tyr Phe Gln Arg Val Leu Ser Ser Ser Ala Thr Tyr Ala Gln Val
            260                 265                 270

Leu Ser Phe Leu Ala Ala Phe Gly Cys Leu Val Met Ala Leu Pro Ala
        275                 280                 285

Ile Cys Ile Gly Ala Ile Gly Ala Ser Thr Asp Trp Asn Gln Thr Ala
    290                 295                 300

Tyr Gly Phe Pro Asp Pro Lys Thr Lys Glu Glu Ala Asp Met Ile Leu
305                 310                 315                 320

Pro Ile Val Leu Gln Tyr Leu Cys Pro Val Tyr Ile Ser Phe Phe Gly
                325                 330                 335

Leu Gly Ala Val Ser Ala Ala Val Met Ser Ser Ala Asp Ser Ser Ile
            340                 345                 350

Leu Ser Ala Ser Ser Met Phe Ala Arg Asn Ile Tyr Gln Leu Ser Phe
        355                 360                 365
```

-continued

```
Arg Gln Asn Ala Ser Asp Lys Glu Ile Val Trp Val Met Arg Ile Thr
        370                 375                 380

Phe Val Phe Gly Ala Ser Ser Ala Thr Ala Met Ala Leu Leu Thr Lys
385                 390                 395                 400

Thr Val Tyr Gly Leu Trp Tyr Leu Ser Ser Asp Leu Val Tyr Ile Ile
                405                 410                 415

Ile Phe Pro Gln Leu Leu Cys Val Leu Phe Ile Lys Gly Thr Asn Thr
                420                 425                 430

Tyr Gly Ala Val Ala Gly Tyr Ile Phe Gly Leu Phe Leu Arg Ile Thr
            435                 440                 445

Gly Gly Glu Pro Tyr Leu Tyr Leu Gln Pro Leu Ile Phe Tyr Pro Gly
        450                 455                 460

Tyr Tyr Pro Asp Lys Asn Gly Ile Tyr Asn Gln Arg Phe Pro Phe Lys
465                 470                 475                 480

Thr Leu Ser Met Val Thr Ser Phe Phe Thr Asn Ile Cys Val Ser Tyr
                485                 490                 495

Leu Ala Lys Tyr Leu Phe Glu Ser Gly Thr Leu Pro Pro Lys Leu Asp
            500                 505                 510

Ile Phe Asp Ala Val Val Ser Arg His Ser Glu Glu Asn Met Asp Lys
        515                 520                 525

Thr Ile Leu Val Arg Asn Glu Asn Ile Lys Leu Asn Glu Leu Ala Pro
    530                 535                 540

Val Lys Pro Arg Gln Ser Leu Thr Leu Ser Ser Thr Phe Thr Asn Lys
545                 550                 555                 560

Glu Ala Leu Leu Asp Val Asp Ser Ser Pro Glu Gly Ser Gly Thr Glu
                565                 570                 575

Asp Asn Leu Gln
            580

<210> SEQ ID NO 28
<211> LENGTH: 576
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 28

Met Ala Asp Leu Leu Gly Ile Val Ala Ile Val Phe Phe Tyr Val Leu
  1               5                  10                  15

Ile Leu Val Val Gly Ile Trp Ala Gly Arg Lys Ser Lys Ser Ser Lys
                20                  25                  30

Glu Leu Glu Ser Glu Ala Gly Ala Ala Thr Glu Glu Val Met Leu Ala
            35                  40                  45

Gly Arg Asn Ile Gly Thr Leu Val Gly Ile Phe Thr Met Thr Ala Thr
        50                  55                  60

Trp Val Gly Gly Gly Tyr Ile Asn Gly Thr Ala Glu Ala Leu Tyr Asn
65                  70                  75                  80

Gly Gly Leu Leu Gly Cys Gln Ala Pro Val Gly Tyr Ala Ile Ser Leu
                85                  90                  95

Val Met Gly Gly Leu Phe Ala Lys Lys Met Arg Glu Glu Gly Tyr
                100                 105                 110  Tyr

Ile Thr Met Leu Asp Pro Phe Gln His Lys Tyr Gly Gln Arg Ile Gly
            115                 120                 125

Gly Leu Met Tyr Val Pro Ala Leu Leu Gly Glu Thr Phe Trp Thr Ala
```

```
            130                 135                 140
Ala Ile Leu Ser Ala Leu Gly Ala Thr Leu Ser Val Ile Leu Gly Ile
145                 150                 155                 160

Asp Met Asn Ala Ser Val Thr Leu Ser Ala Cys Ile Ala Val Phe Tyr
                165                 170                 175

Thr Phe Thr Gly Gly Tyr Tyr Ala Val Ala Tyr Thr Asp Val Val Gln
                180                 185                 190

Leu Phe Cys Ile Phe Val Gly Leu Trp Val Cys Val Pro Ala Ala Met
            195                 200                 205

Val His Asp Gly Ala Lys Asp Ile Ser Arg Asn Ala Gly Asp Trp Ile
        210                 215                 220

Gly Glu Ile Gly Gly Phe Lys Glu Thr Ser Leu Trp Ile Asp Cys Met
225                 230                 235                 240

Leu Leu Leu Val Phe Gly Gly Ile Pro Trp Gln Val Tyr Phe Gln Arg
                245                 250                 255

Val Leu Ser Ser Lys Thr Ala His Gly Ala Gln Thr Leu Ser Phe Val
                260                 265                 270

Ala Gly Val Gly Cys Ile Leu Met Ala Ile Pro Pro Ala Leu Ile Gly
            275                 280                 285

Ala Ile Ala Arg Asn Thr Asp Trp Arg Met Thr Asp Tyr Ser Pro Trp
290                 295                 300

Asn Asn Gly Thr Lys Val Glu Ser Ile Pro Pro Asp Lys Arg Asn Met
305                 310                 315                 320

Val Val Pro Leu Val Phe Gln Tyr Leu Thr Pro Arg Trp Val Ala Phe
                325                 330                 335

Ile Gly Leu Gly Ala Val Ser Ala Ala Val Met Ser Ser Ala Asp Ser
                340                 345                 350

Ser Val Leu Ser Ala Ala Ser Met Phe Ala His Asn Ile Trp Lys Leu
                355                 360                 365

Thr Ile Arg Pro His Ala Ser Glu Lys Glu Val Ile Ile Val Met Arg
            370                 375                 380

Ile Ala Ile Ile Cys Val Gly Ile Met Ala Thr Ile Met Ala Leu Thr
385                 390                 395                 400

Ile Gln Ser Ile Tyr Gly Leu Trp Tyr Leu Cys Ala Asp Leu Val Tyr
                405                 410                 415

Val Ile Leu Phe Pro Gln Leu Leu Cys Val Val Tyr Met Pro Arg Ser
                420                 425                 430

Asn Thr Tyr Gly Ser Leu Ala Gly Tyr Ala Val Gly Leu Val Leu Arg
            435                 440                 445

Leu Ile Gly Gly Glu Pro Leu Val Ser Leu Pro Ala Phe Phe His Tyr
450                 455                 460

Pro Met Tyr Thr Asp Gly Val Gln Tyr Phe Pro Phe Arg Thr Thr Ala
465                 470                 475                 480

Met Leu Ser Ser Met Ala Thr Ile Tyr Ile Val Ser Ile Gln Ser Glu
                485                 490                 495

Lys Leu Phe Lys Ser Gly Arg Leu Ser Pro Glu Trp Asp Val Met Gly
            500                 505                 510

Cys Val Val Asn Ile Pro Ile Asp His Val Pro Leu Pro Ser Asp Val
            515                 520                 525

Ser Phe Ala Val Ser Ser Glu Thr Leu Asn Met Lys Ala Pro Asn Gly
        530                 535                 540

Thr Pro Ala Pro Val His Pro Asn Gln Gln Pro Ser Asp Glu Asn Thr
545                 550                 555                 560
```

```
Leu Leu His Pro Tyr Ser Asp Gln Ser Tyr Tyr Ser Thr Asn Ser Asn
            565                 570                 575

<210> SEQ ID NO 29
<211> LENGTH: 579
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 29

Met Ala Val Asn Ile Leu Gly Val Val Ser Ile Gly Ile Phe Tyr Val
 1               5                  10                  15

Ile Ile Leu Ile Val Gly Ile Trp Ala Ser Arg Lys Lys Thr Ser
             20                  25                  30

Ser Gly Gln Ser Glu Thr Glu Glu Ile Met Leu Ala Gly Arg Asn Ile
             35                  40                  45

Gly Phe Leu Val Gly Val Leu Thr Met Thr Ala Thr Trp Val Gly Gly
         50                  55                  60

Gly Tyr Ile Asn Gly Thr Ala Glu Ala Met Tyr Asn Asn Gly Leu Val
 65                  70                  75                  80

Trp Cys Gln Ala Pro Phe Gly Tyr Ala Leu Ser Leu Phe Ile Gly Gly
                 85                  90                  95

Ile Val Phe Ala Lys Lys Met Arg Ser Gln Gly Tyr Val Thr Met Leu
            100                 105                 110

Asp Pro Leu Gln Glu Asn Phe Gly Ser Lys Met Gly Gly Leu Leu Phe
            115                 120                 125

Leu Pro Ala Leu Cys Gly Glu Ile Phe Trp Ser Ala Ala Ile Leu Ala
        130                 135                 140

Ala Leu Gly Ala Thr Ile Ser Val Ile Thr Glu Leu Glu Ser Ser Thr
145                 150                 155                 160

Ser Ile Ile Val Ser Ser Ile Ala Val Phe Tyr Thr Phe Phe Gly
                165                 170                 175

Gly Phe Tyr Ser Val Ala Tyr Thr Asp Val Ile Gln Leu Phe Cys Ile
            180                 185                 190

Phe Phe Gly Leu Trp Leu Cys Ile Pro Phe Ser Phe Ser His Glu Ala
        195                 200                 205

Val Gly Ser Leu Ser Ser Ile Asp Phe Leu Gly Ser Val Lys Leu Ser
    210                 215                 220

Asp Ala Gly Ile Asn Val Asp Ile Trp Leu Leu Leu Ile Phe Gly Gly
225                 230                 235                 240

Ile Pro Trp Gln Val Tyr Phe Gln Arg Val Leu Ser Ala Lys Asn Val
                245                 250                 255

Ser Asn Ala Gln Val Leu Ser Tyr Val Ala Ala Val Gly Cys Val Val
            260                 265                 270

Met Ala Ile Pro Ala Ile Leu Ile Gly Val Ile Ala Lys Ala Thr Ala
        275                 280                 285

Trp Asn Glu Thr Ala Leu Gly Met Pro Leu Thr Pro Asn Asp Thr Ser
    290                 295                 300

Leu Val Leu Pro Leu Val Leu His Tyr Leu Thr Pro Thr Ala Val Ser
305                 310                 315                 320

Phe Phe Gly Leu Gly Ala Val Ser Ala Ala Val Met Ser Ser Ser Asp
                325                 330                 335

Ser Ser Ile Leu Ser Ala Ser Ser Leu Phe Ser Arg Asn Val Tyr Lys
```

-continued

```
                    340             345             350
Leu Ile Phe Arg Gln Lys Ala Ser Glu Arg Phe Val Val Trp Val Ile
        355             360             365
Arg Ile Ser Ile Leu Val Val Gly Ile Leu Ala Thr Ala Met Ala Leu
        370             375             380
Thr Val Lys Ser Val Tyr Gly Leu Trp Tyr Leu Ser Ser Asp Leu Ile
385             390             395             400
Tyr Val Ile Leu Phe Pro Gln Leu Leu Cys Val Val His Leu Lys Lys
                405             410             415
Tyr Cys Asn Thr Tyr Gly Ser Leu Ser Ala Tyr Ile Val Gly Phe Leu
                420             425             430
Leu Arg Ala Leu Gly Gly Glu Ser Ile Leu Gly Leu Glu Pro Val Ile
        435             440             445
His Tyr Pro Phe Phe Ser Glu Thr Ser Gly Gln Arg Phe Pro Glu Arg
        450             455             460
Thr Leu Ser Met Leu Ala Ser Leu Ile Thr Leu Ala Ile Ser Gly
465             470             475             480
Ile Thr Lys Trp Ile Phe Glu Met Asn His Leu Pro Ala Lys Leu Asp
                485             490             495
Ile Phe Arg Cys Val Thr Asn Ile Gln Glu Asn Ile Ile Lys Ile Gln
                500             505             510
Lys Leu Gln Gly Gly Ala Met Pro Val Leu Asp Ser Ile Lys Lys Glu
        515             520             525
Ile Tyr Gln Lys Asp Met Asn Asn Ser Phe Asn Thr Val Val Asn Ser
        530             535             540
Gly Asn Ala Glu Leu Leu Thr Asp Ser Thr Tyr Ser Gly Lys Ile Lys
545             550             555             560
Lys Asn Asn Ser Ser Thr Gln Glu Arg Lys Tyr Gly Ser Val Asn Asp
                565             570             575
Thr Val Phe
```

POLYNUCLEOTIDE ENCODING A MOUSE CHOLINE TRANSPORTER

This application is a divisional to U.S. patent application Ser. No. 09/911,077 filed on Jul. 23, 2001 now abandoned, the entire contents of each which are incorporated herein by reference. Additionally, all patents, published patent applications, and other references cited throughout this specification are hereby incorporated by reference in their entireties.

The invention disclosed herein was made with the support of the U.S. Government under The National Institutes of Health Grant RO1 MH58921 and National Institute of Health Training Grant HL 07323. Accordingly, the U.S. Government may have certain rights in this invention.

BACKGROUND OF THE INVENTION

I. Field of the Invention

The present invention relates generally to the fields of pharmacology. More particularly, it provides cDNA encoding novel high affinity choline transporters, methods for their use in screening and therapy.

II. Description of Related Art

The molecular mechanisms involved in neurotransmission in the central nervous system is a multi-step process involving the release of neurotransmitter from the presynaptic terminal, diffusion across the synaptic cleft, and binding to receptors resulting in an alteration in the electrical properties of the postsynaptic neuron. For most neurotransmitters, transmission is terminated by the rapid uptake of neurotransmitter by specific, high-affinity transporters located in the presynaptic terminal and/or surrounding glial cells (Kanner et al. 1987). Since inhibition of uptake by pharmacologic agents increases the levels of neurotransmitter in the synapse, and enhances synaptic transmission, neurotransmitter transporters provide important targets for therapeutic intervention. (U.S. Pat. No. 5,658,786).

In the central and peripheral nervous system, cholinergic neurons regulate a variety of autonomic, cognitive and motor functions (Fibiger, 1991). Dysfunction of cholinergic signaling has been implicated in Alzheimer's disease (Coyle et al., 1983), Parkinson's disease Calabresi et al., 2000), schizophrenia (Tandon, 1999), Huntington's disease (Lange et al., 1992) and dysautonomia (Baron et al., 1996).

Okuda et al. (2000) have identified and characterized a high-affinity choline transporter in the rat. However, using human gene products in drug development offers significant advantages over those of other species, which may not exhibit the same pharmacological profiles as human genes. Reagents developed to interfere or modulate the rat transporter may not be as clinically relevant as reagents developed using a human system. Also, since no cell lines exist which express the human choline transporter, lack of cross-reactivity must be validated using less ideal tissue, for example, postmortem brain tissue. Okuda et al. (2000) provides no sequence relationship between rat and human choline transporters. Also, the Okuda's proposed topology for rat choline transporters is distinct from the topology as described herein. Okuda et al. proposes 12 transmembrane domains for rat and *C. elegans* choline transporters. However, human (Apparsundaram et al. 2000) and mouse (Apparsundaram et al., *Biochem. Soc. Trans.* 29:711-6, 2001) choline transporters were not described, and these transporters have a distinct protein topology (13 transmembrane domains) based on the sequence relationship of cDNAs to related $Na^+$/glucose family of transporters.

To facilitate a human-target based approach to drug design, a human ortholog of CHT has been cloned. A mouse ortholog of CHT also has been cloned. These genes will be beneficial in drug screening and animal modeling of cholinergic function.

SUMMARY OF THE INVENTION

The present invention contemplates an isolated polynucleotide, an isolated polypeptide, a recombinant host cell, a recombinant vector, a purified protein, an antibody, a nucleic acid detection kit, a method for screening cholinergic therapeutics, a method of treating a patient, a method of gene therapy and transgenic CHT mice.

An isolated polynucleotide encoding a polypeptide comprising the amino sequence essentially as set forth in SEQ ID NO: 2 and of SEQ ID NO: 4 are claimed. Another aspect of the current invention comprises the polynucleotide of the nucleic acid sequence essentially as set forth in SEQ ID NO: 1 and SEQ ID NO: 3. The polynucleotide may be operatively linked to a promoter such as a tissue-specific promoter. It is an aspect of the invention that the polynucleotide is a cDNA segment. The polynucleotide may be comprised in a vector such as one selected from the group consisting of a retroviral vector, an adenoviral vector, and adeno-associated viral vector, a lentivirus vector, a vaccinia viral vector, and a herpesviral vector. The polynucleotide may also comprise a pharmaceutically acceptable formulation.

Another aspect of the current invention comprises a recombinant host cell comprising a DNA segment encoding an isolated human choline transporter. The DNA segment encoding a polypeptide may have the amino acid sequence essentially as set forth in SEQ ID NO:2. It is preferred that the host cell is a human cell.

Yet another aspect of the current invention comprise a recombinant vector comprising a DNA segment encoding a human choline transporter polypeptide under the control of a promoter. The recombinant vector preferably enhances cholinergic signaling.

Another aspect of the current invention comprises a purified and isolated polynucleotide wherein the polynucleotide comprises a sequence identical or complementary to between 14 and 100 contiguous nucleotides of SEQ ID NO:1. The polynucleotide may comprises at least 14, 20, 30, 40, 50, 60, 70, 80, 90, 100 contiguous nucleotides of SEQ ID NO:1. The polynucleotide may also comprises 150, 200, 300, 400, 500, 600, 700, 800, 900, 1000, 1100, 1200, 1300, 1400, 1500, 1600, 1700 or more contiguous nucleotides of SEQ ID NO:1. The polynucleotide may be complementary to at least 14, 20, 30, 40, 50, 60, 70, 80, 90, 100 contiguous nucleotides of SEQ ID NO:1. The polynucleotide may also be complementary to at least 150, 200, 300, 400, 500, 600, 700, 800, 900, 1000, 1100, 1200, 1300, 1400, 1500, 1600, 1700 or more contiguous nucleotides of SEQ ID NO:1. Also contemplated is a purified peptide comprising at least 10 contiguous amino acids of SEQ ID NO:2. The peptide may comprises at least 20, 30, 40, 50, 60, 70, 80, 90, 100, 200, 300, 400, 500 or up to 580 contiguous nucleotides of SEQ ID NO: 2.

It is an aspect of the current invention that the peptide is sensitive to hemicholinium-3. The peptide may be mutated relative to the wild-type hCHT protein, and may modulate high-affinity choline uptake. The peptide may bind to an antibody specific to the polypeptide comprising at least 10 contiguous amino acids of SEQ ID NO:2 encoded by human cDNA.

Another aspect of the invention comprises a method of using a DNA segment that encodes an isolated human choline transporter protein, comprising the steps of (a) preparing a recombinant vector in which a human choline transporter encoding said DNA segment is positioned under the control of a promoter; (b) introducing said recombinant vector into a host cell; (c) culturing said host cell under conditions effective to allow expression of the encoded protein or peptide; and (d) collecting said expressed protein or peptide.

Yet another aspect of the invention comprises an isolated polynucleotide encoding a polypeptide comprising the amino sequence essentially set fourth in SEQ ID NO: 4. The polynucleotide may comprise the nucleic acid sequence essentially as set forth in SEQ ID NO:3 and optionally may be operatively linked to a promoter. The polynucleotide may be a cDNA segment and may be comprised in a vector.

Another aspect of the invention comprises a recombinant host cell comprising a DNA segment encoding an isolated choline transporter having the amino acid sequence essentially as set forth in SEQ ID NO:4. The recombinant vector may comprise a DNA segment encoding a mouse choline transporter polypeptide under the control of a promoter.

Yet another aspect of the invention comprises a purified and isolated polynucleotide wherein the polynucleotide comprises a sequence identical or complementary to between 10 and 100 contiguous nucleotides of SEQ ID NO:3.

In still yet another embodiment, there is provided a purified peptide comprising at least 10 contiguous amino acids of SEQ ID NO:4. The peptide may bind to an antibody specific to the polypeptide comprising at least 10 contiguous amino acids of SEQ ID NO:4 encoded by mouse cDNA.

Another aspect of the invention comprises an antibody that immunologically binds to a protein or peptide encoded by a contiguous sequence from the nucleic acid sequence essentially as set forth in SEQ ID NO:1.

Anther aspect comprises an antibody that immunologically binds to a CHT protein or peptide that includes a contiguous amino acid sequence from SEQ ID NO:2. The antibody is a polyclonal or a monoclonal antibody and may be operatively attached to a therapeutic agent or a detectable label such as a fluorescent label, a chemiluminescent label, a electroluminescent label, a radiolabel and an enzyme. It is an aspect of the invention that the label be a green fluorescent protein or a β-galactosidase. The antibody may be adapted to detect losses in cholinergic neurons.

In still yet another embodiment, there is provided a method of screening for cholinergic therapeutics comprising: (a) obtaining a candidate substance; (b) obtaining a recombinant cell comprising a polynucleotide encoding a choline transporter (CHT) polypeptide and a promoter heterologous to the polypeptide coding region, wherein said promoter directs expression of said CHT polypeptide; (c) combining candidate substance with said cell; and (d) determining whether said candidate substance modulates high-affinity choline uptake. The CHT is preferably a human choline transporter (hCHT) or a mouse choline transporter (mCHT), and the cell is preferably a human cell, a mouse cell or an invertebrate cell. The candidate substance may be combined with the cell in vitro or in vivo. The candidate substance may be an acetylcholine receptor therapeutic, an antibody such as the 15 C terminus amino acids of SEQ ID NO: 2 (SEQ ID NO: 25), a gene probe; it may be selected from a small molecule library or may have a low affinity against hCHT.

It is provided that the method of determining may comprise detecting a label such as hemicholinium-3 operatively attached to said polypeptide, Western Blot analysis, using a choline transport assay such as a [$^3$H] choline transport assay using COS-7 cells, using in situ hybridization, PCR, gene chip analysis or a negative screen. The candidate substance may be screened specificity for acetylcholine receptor-directed agents such as nicotinic or muscarinic acetylcholine receptor-directed agents.

It is also an aspect of the current invention that mutations to the hCHT gene are mapped, that cholinergic gene expression is quantitatively evaluated, that the candidate substance is used to probe human cholinergic neurons and that the candidate substance is used to identify cholinergic neurons in a postmortem brain.

Yet another embodiment of the current invention comprises a method of treating a patient comprising: (a) obtaining a candidate substance; (b) obtaining a recombinant cell comprising a polynucleotide encoding a choline transporter (CHT) polypeptide and a promoter heterologous to the polypeptide coding region, wherein said promoter directs expression of said CHT polypeptide; (c) combining candidate substance with said cell; (d) determining whether said candidate substance modulates high-affinity choline uptake; and (e) delivering said candidate substance in a therapeutic formulation to a patient. An antibody may be used to aid in transport of the candidate substance, such as to the brain of a patient being treated. The antibody may be SEQ ID NO: 25 It is envisioned that a probe is attached to the antibody. This method may be used for treating a neuromuscular, autonomic or central nervous system disorder, including Parkinson's disease, Huntington's disease, Alzheimer's, schizophrenia, dysautonomia or myasthenia gravis. In situ hybridization, PCR or gene chip analysis. A negative screen may also be used. Combining the candidate substance and the cell may occur in vitro or in vivo.

Yet another aspect of the current invention comprises a nucleic acid detection kit comprising, in suitable container means, an isolated human choline transporter nucleic acid segment and a detection reagent. The detection reagent is preferably a detectable label that is linked to said nucleic acid segment such as hemicholinium-3. The detection kit may also comprise a gene chip or an antibody.

Another aspect of the current invention comprises a transgenic mouse, wherein the mouse lacks at least one functional mouse choline transporter (mCHT) allele. The mouse may lack two functional mCHT alleles or the gene essentially as set forth in SEQ ID NO: 3.

Yet another aspect of the current invention comprises a transgenic mouse, wherein the genome of said mouse comprises a choline transporter (CHT) encoding a DNA segment under the control of a heterologous promoter. It is preferred that the mouse expresses more CHT polypeptides when compared to a non-transgenic littermate.

Another aspect of the current invention comprises a transgenic mouse, wherein at least one mouse choline transporter (mCHT) allele is operably attacted to a detectable label. The label may be selected from the group consisting of a fluorescent label (i.e. a a green fluorescent protein, a red fluourescent protein, or a blue fluorescent protein), a chemiluminescent label, a electroluminescent label, a radiolabel and an enzyme (i.e. β-galactosidase).

Another aspect of the current invention is a method comprising the step of delivering a polynucleotide encoding a choline transporter (CHT) polypeptide to a cell. The CHT polypeptide may comprise the amino sequence essentially as set forth in SEQ ID NO: 2. This method preferably causes an increase in cholinergic function in said cell. Preferably, the cell is in a patient having Parkinson's disease, Huntington's disease, Alzheimer's, schizophrenia, dysautonomia or myasthenia gravis.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2—Alignment of amino acid sequence of high-affinity choline transporters. Alignment of mCHT with species orthologs was performed using version 1.6.3 of Lasergene software. Abbreviations are as follows: mCHT, murine (SEQ ID NO:4); hCHT, human (SEQ ID NO:2); rCHT, rat (SEQ ID NO:6; CHO-1, Caenorhabtiditis elegans (SEQ ID NO:8); ChCoT, Limulus polyphemus (SEQ ID NO:29). Residues matching mCHT sequences are blackened. Residues spanning putative TMDs inferred from hydropathy analysis are represented by line drawn above the sequences.

FIG. 4—Predicted hCHT amino acid sequence (SEQ ID NO:2). Amino acid sequence of the derived from hCHT. The location of 13 TMDs are shown with solid lines above the corresponding amino acid residues. Asterisks indicate potential extracellular N-glycosylation sites.

(FIG. 11C) [$^3$H]HC-3 binding as a function of HC-3 concentration. (FIG. 11D) Inhibition of [$^3$H]HC-3 binding as a function o inhibitor concentration.

FIGS. 16—3D focal reconstruction of ChT-ir at the neuromuscular junction of the diaphragm. Choline transporter antibodies stain cholinergic synapses on muscle cell FIG. 17—Image of ChT-ir at the neuromuscular junction of the bladder. Choline transporter antibodies stain parasympathetic neuronal terminals on smooth muscle in the bladder.

DESCRIPTION OF ILLUSTRATIVE EMBODIMENTS

I. The Present Invention

The present invention overcomes deficiencies in the art by providing human and mouse high-affinity choline transporters (CHT).

II. Choline

Choline, a natural amine, ($C_5H_{15}NO_2$) is often classed in the vitamin B complex and is a constituent of many other biologically important molecules. Choline is a precursor of a variety of lipids including the neurotransmitter acetylcholine, membrane lipids such as phosphatidylcholine and sphingomyelin, and signaling lipids such as platelet-activating factor and sphingosylphosphorylcholine. Choline is unable to permeate cell membranes and therefore uses a carrier-mediated transport system to cross the membrane barrier. In the central and peripheral nervous system, choline and cholinergic neurons are used to regulate a variety of autonomic, cognitive and motor functions (Fibiger, 1991).

a. Choline Uptake

There are multiple low-affinity choline transport pathways which provide choline for metabolic needs and membrane phospholipid synthesis. Cholinergic neurons also have a distinct high-affinity choline uptake (HACU) process that provides choline for the synthesis of acetylcholine (ACh) (Yamamura et al., 1972; Blusztajn, 1998). Selective blockade of HACU by hemicholinium-3 (HC-3) can reduce ACh synthesis and release in vitro and impair cholinergic function in vivo (Murrin et al., 1977; Guyenet et al., 1973). The activity of HACU is also highly regulated by neuronal activity, neurotransmitters and second messengers (Atweh et al., 1975; Simon et al., 1975; Cancela et al., 1995; Vogelsberg, et al., 1997; Breer et al., 1990;Yamada. et al., 1991) and therefore serves as a potential mechanism for the modulation of cholinergic function.

HACU has been defined in the rat and human brain as a $Na^+/Cl^-$ dependent process with a Km of ~1 μM for choline (Yamamura et al., 1972; Rylett et al., 1983). Initial attempts to identify HACU at a molecular level led to the isolation and partial purification of membrane proteins of 35 to 90 kDa from Torpedo electromotor nerve terminals, as well as from insect and rat neural tissues (Rylett 1988; Knipper et al., 1989; Knipper et al., 1991; Rylett et al., 1996). Mayser et al. (1992) reported the initial cloning of a choline transporter within this gene family; however, this molecule has since been redesignated as a creatine transporter based on substrate preference and regional distribution (Guimba. et al., 1993; Schloss et al., 1994). More recently, O'Reagan et al. (2000) utilized complementation of choline defiencies in yeast to identify a novel choline transporter, CTL1. However, the distribution, ion-dependence and pharmacology of this transporter differ from that expected for presynaptic HACU.

Figure 1:
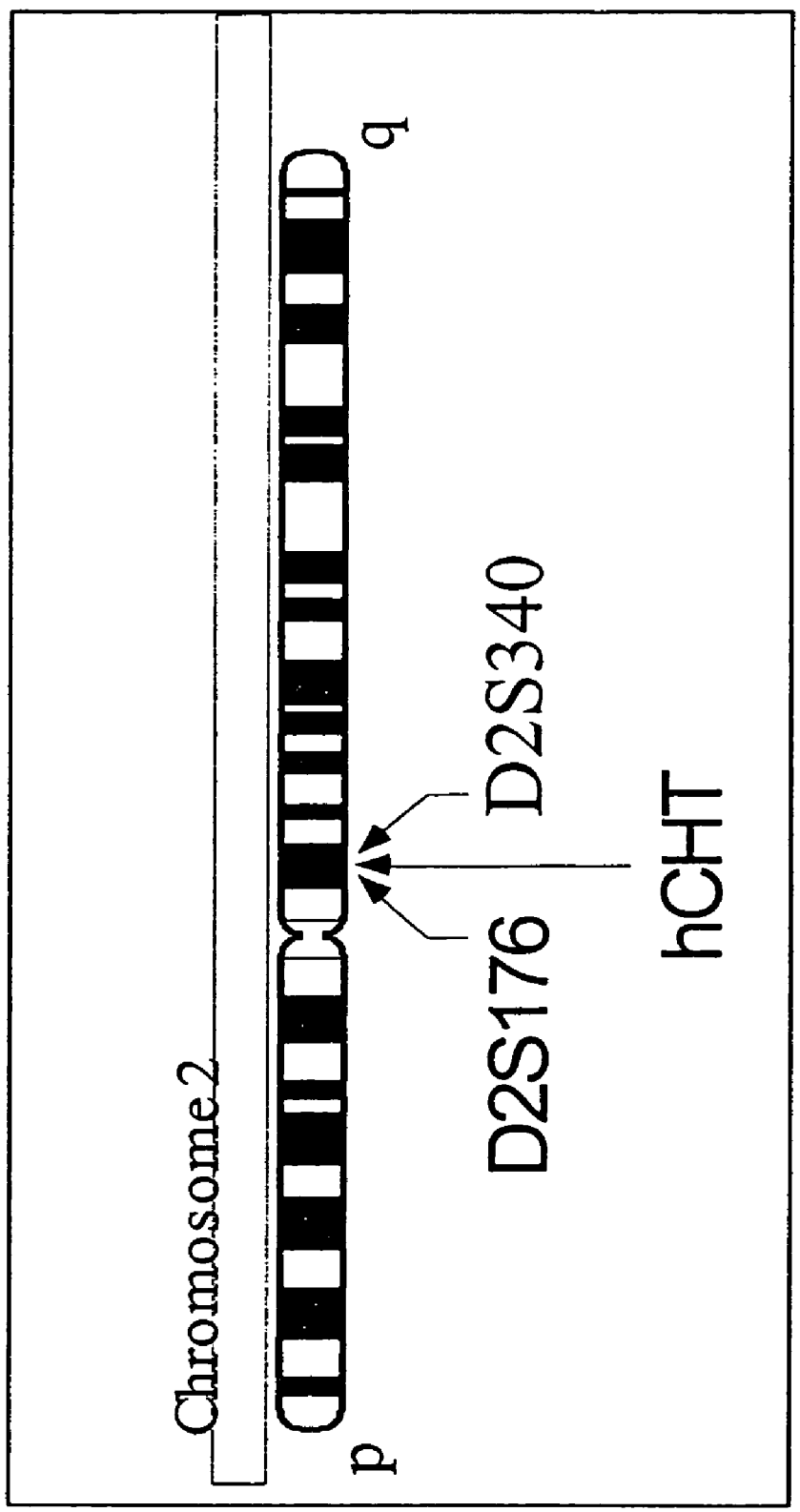
FIG. 1—Schematic representation of the localization of the human choline transporter to chromosome 2. Radiation hybrid mapping localizes hCHT to human chromosome 2q12. This is the first step in the assessment of hCHT as a risk factor in disorders involving altered cholinergic function.
Figure 2:
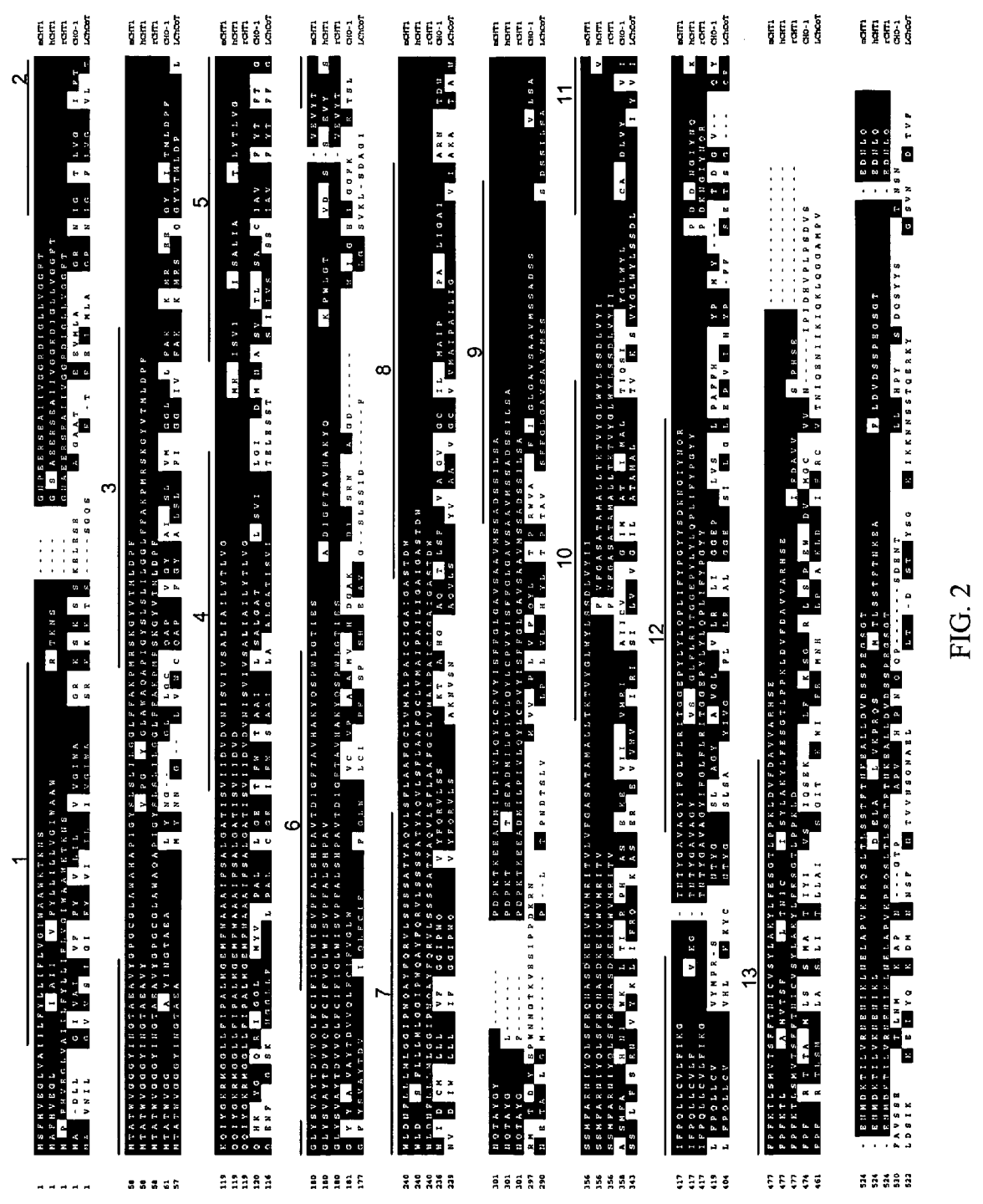
Figure 3:
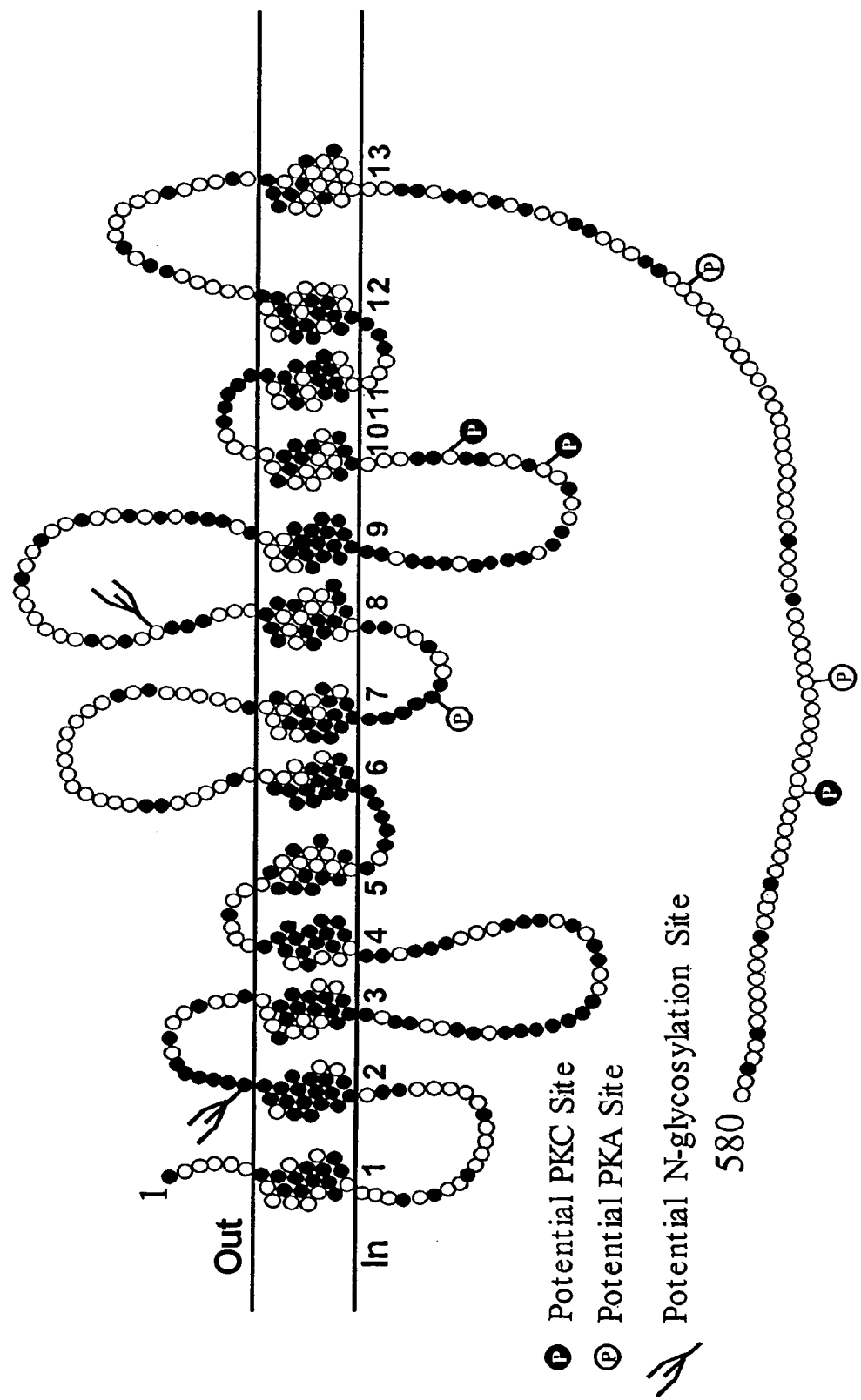
FIG. 3—Predicted secondary structure of hCHT. The N-terminal is located on the external side of the membrane. 13 transmembrane domains are proposed with an extracellular NH2 terminus and a cytoplasmic COOH terminus. Black circles represent amino acids conserved with rat, mouse, and C. elegans choline transporters. The C-terminal is located on the internal side of the membrane (Apparsundaram et al., 2000).

A major breakthrough in elucidating the molecular basis of HACU was achieved by Okuda and co-workers (Okuda et al., 2000) who identified a choline transporter (CHO-1) expressed in the cholinergic neurons of the nematode C. elegans. These investigators also identified a rat homologue (rCHT1) and found the expression pattern and functional characteristics of rCHT1 to be consistent with the HACU in the rat brain (Okuda et al., 2000). Using the sequence information of rCHT1 and the information provided by Human Genome Project, a human ortholog hCHT was cloned and hybridizing mRNAs were identified in the human brain. Similarly, mouse CHT was cloned. Transport and antagonist binding studies in COS-7 cells reveal a substrate specificity, ion-dependence and pharmacology consistent with HACU. Finally, an initial gene structure for hCHT and a map of its chromosomal location to chromosome 2q12 is provided (FIG. 1). The alignment of amino acid sequence of rat, human and mouse high-affinity choline transporters is given along with CHO-1 and LChCoT sequences (FIG. 2). The predicted secondary structure of the hCHT protein is shown in FIG. 3 with the antipeptide monoclonal CHT antibody and antipeptide polyclonal CHT antibody regions marked.

b. Choline Transporters

The high-affinity choline transporter is responsible for choline transport into cholinergic nerve terminals to provide for acetylcholine biosynthesis. Acetylcholine, a major neurotransmitter in the brain and periphery nervous system, is involved in signaling motor and cognitive function. Altered cholinergic signaling is evident in neuromuscular disorders as well as disruptions of higher cognitive function occurring in Alzheimer's and other disease.

Previous cDNAs encoding choline transporters (Okuda et al., 2000) are not of human origin and reagents developed to interfere or modulate the transporter are not as clinically relevant. Also, since no cell lines exist which express the human choline transporter, lack of crossreactivity must be validated using, for example, postmortem brain tissue. The choline transporters of the current invention (et al SEQ ID NO: 2, SEQ ID NO: 4) are more clinically relevant than what is provided by the art.

Routine membrane preparations enriched in the human or mouse choline transporter which are expressed from stable cell lines can be used for testing for cross-reactivity or for direct product development of choline transporter modulators.

In cholinergic neurons, choline transported via a high-affinity choline transporter located on the neuronal membrane is rate limiting in acetylcholine biosynthesis and therefore a potential target for modulating cholinergic function. In non-adrenergic neurons, active re-uptake of norepinephrine (NE) into presynaptic sites via a NE transporter located on the neuronal membrane is the primary mechanism responsible for the termination of effects of NE. Importantly, this NE transporter is a target for antidepressants and psychostimulants like cocaine and amphetamine.

Cholinergic receptors are proteins embedded in the cell membrane that respond to the neurotransmitter acetylcholine. There are two families of cholinergic receptors, the nicotinic and muscarinic receptor families. The response of most autonomic effector cells in peripheral visceral organs is muscarinic, and the response in parasympathetic ganglia, the sympathetic ganglia, and in skeletal muscle, is nicotinic.

Muscarinic receptors are known to mediate a variety of physiological responses in the central and peripheral nervous systems. The first subtype of muscarinic receptors, $M_1$ muscarinic receptors are involved in learning and memory function in the brain and are known to regulate gastric acid secretion in the stomach. $M_2$ receptors are known to regulate acetylcholine release in the central nervous system and control cardiac muscle contraction. $M_3$ receptors are known to mediate smooth muscle contractions and promotes secretion from exocrine glands. $M_2$ receptors are believed to be involved in the perception of pain. $M_5$ receptors are believed to regulate dopaminergic activity in the brain (U.S. Pat. No. 6,096,767). The use of several substituted tetrahydropyrimidine and tetrahydropyridine compositions that bind to and activate muscarinic receptors is disclosed (U.S. Pat. Nos. 5,726,179, 5,618,818, 5,403,845, and 5,175,166). These compounds exhibit agonist activity useful in the treatment of neurological disorders such as Alzheimer's.

Nicotinic receptors are ligand-gated ion channels, and their activation always causes a rapid increase in cellular permeability to $Na^+$ and $K^+$, depolarization, and excitation (U.S. Pat. No. 6,177,451). They are glycoproteins composed of five subunits with the stoichiometry $\alpha\alpha\beta\kappa\delta$ which are each encoded by a separate gene. The $\alpha\alpha\beta\kappa\delta$ complex is a functional receptor containing both ligand binding sites and a ligand-gated transmembrane channel. (For a review, see Karlin, et al., 1986 and McCarthy, et al., 1986.) There are two subtypes of nicotinic receptors, the neuromuscular nicotinics, termed NM, and the neuronal or ganglionic nicotinics, termed NN.

U.S. Pat. No. 6,177,451 discloses epibatidine and synthetic derivatives that are nicotine receptor agonists. Epibatidine is one of three natural alkaloid nicotinic receptor agonist, the other two natural alkaloids include nicotine and lobeline. See, Taylor, in Goodman and Gilman's The Pharmacological Basis of Therapeutics, 18th Ed., Gilman et al, eds., Pergamon Press, pp. 166-186 (1990). U.S. Pat. No. 6,136,550 discloses a family of neuronal nicotinic acetylcholine receptors comprised of neuronal agonist and non-agonist binding subunits, and DNA sequences encoding the receptors.

cDNAs which encode a choline transporter were isolated from rat spinal chord and brainstem by Mayser et al. (1992). The predicted protein has considerable amino acid homology and shares several structural features including twelve putative transmembrane regions with other neurotransmitter transporters. CHOT1 mRNA was found in the brain, cerebellum, spinal cord and, to a lesser extent, in the heart.

cDNAs which were believed to encode a choline transporter were isolated from rat spinal chord and brainstem by Mayser et al (1992). The predicted protein which is now recognized as a creatine transporter (Saltarelli et at, 1996) has considerable amino acid homology and shares several structural features including twelve putative transmembrane regions with other neurotransmitter transporters. CHOT1 mRNA was found in the brain, cerebellum, spinal cord and, to a lesser extent, in the heart.

III. Diseases or Disorders Affected by Cholinergic Signaling

In the central and peripheral nervous systems, cholinergic neurons regulate a variety of autonomic, cognitive and motor functions (Fibiger, 1991). Agents that modulate the choline transporter can be used to influence cholinergic signaling therapeutically for neuromuscular, autonomic or central nervous system (CNS) disorders. Also, animal models for choline transporter function can be used to better understand and treat disorders that effect the central and peripheral nervous system. Since altered cholinergic function is a feature of various diseases, the discovery of substances that modulate cholinergic transport is invaluable in the development and use of treatments for these diseases. Dysfunction of cholinergic signaling has been implicated in, for example, Alzheimer's disease (Coyle et al, 1983), Parkinson's disease (Calabresi et al, 2000), schizophrenia (Tandon, 1999) Huntington's disease (Lange et al, 1992) dysautonomia (Baron et al, 1996) and myasthenia.

Acetylcholine is significant in the pharmacotherapy of Parkinson's Disease. A simplistic, but useful, neurochemical model of the function of the basal ganglia suggests that the neostriatum (caudate nucleus and putamen) normally contains balanced inhibitory dopaminergic and excitatory cholinergic components (Duvoisin, 1967). Although cholinergic neurons are not damaged in Parkinson's disease, the decrease in dopaminergic activity results a relative excess of cholinergic influence. Consequently, a strategy for the treatment of Parkinson's Disease is to block cholinergic activity in an attempt to restore the balance of dopaminergic and cholinergic tone in the striatum (U.S. Pat. No. 6,177,451). Candidate substances of the present invention can be used to block cholinergic activity. Also, the combination of dopaminergic agonists and cholinergic antagonists are contemplated.

The degeneration of cholinergic neurons causes a loss of high-affinity choline uptake activity in Alzheimer's disease (Bierer et al., 1995). This major dementing disorder of the elderly is associated with cholinergic neuronal loss and decreased activity of choline acetyltransferase. Therefore, it is an aspect of this invention that modulators of choline transporter function be used to treat Alzheimer's disease.

Myasthenia gravis (MG) is the most common primary disorder of neuromuscular transmission. The usual cause is an acquired immunological abnormality, but some cases result from genetic abnormalities at the neuromuscular junction. The abnormalities in myasthenia gravis arises from a loss of cholinergic signaling at the neuromuscular junction. Mutations in the choline acetyltransferase gene have been found in myasthenic syndromes and these syndromes are likely places therefore where human choline transporter mutations are found.

As acetylcholine is the principal neurotransmitter at all preganglionic sympathetic and parasympathetic synapses and also at all postganglionic parasynpathetic synapses, defecits in the choline transporter may be present with autonomic phenotypes and the manipulation of these transporters pharmacology could be helpful in many autonomic diseases (e.g. heart, bladder, stomach).

IV. Proteinaceous Compositions

In certain embodiments, the present invention concerns novel compositions or methods comprising at least one proteinaceous molecule. The proteinaceous molecule may be a CHT or more preferably an hCHT or mCHT inhibitor, or a delivery agent. The proteinaceous molecule may also be a mutated hCHT or mCHT. The proteinaceous molecule may also be used, for example, as an hCHT or hCHT inhibitor, in a pharmaceutical composition for the delivery of a therapeutic agent or as part of a screening assay in the determination of hCHT or mCHT inhibition. As used herein, a "proteinaceous molecule," "proteinaceous composition," "proteinaceous compound," "proteinaceous chain" or "proteinaceous material" generally refers to, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 560, about 580, about 590, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 1 below.

TABLE 1

| Modified and Unusual Amino Acids | |
|---|---|
| Abbr. | Amino Acid |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |

TABLE 1-continued

| Modified and Unusual Amino Acids | |
|---|---|
| Abbr. | Amino Acid |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In certain embodiments the proteinaceous composition comprises at least one protein, polypeptide or peptide, such as a hCHT or mCHT. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (www.ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments, a proteinaceous compound may be purified. Generally, "purified" will refer to a specific or desired protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody. An hCHT or mCHT may comprise all or part of an antibody that specifically recognizes hCHT or mCHT. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988, incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that the high viscosity will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide which is derived or obtained from an organism. Organisms that may be used include, but are not limited to, a bovine, a reptilian, an amphibian, a piscine, a rodent, an avian, a canine, a feline, a fungal, a plant, or a prokaryotic organism, with a selected animal or human subject being preferred. The "autologous protein, polypeptide or peptide" may then be used as a component of a composition intended for application to the selected animal or human subject. In certain aspects, the autologous proteins or peptides are prepared, for example from whole plasma of the selected donor. The plasma is placed in tubes and placed in a freezer at about −80° C. for at least about 12 hours and then centrifuged at about 12,000 times g for about 15 minutes to obtain the precipitate. The precipitate, such as fibrinogen may be stored for up to about one year.

V. Genes and DNA Segments

Important aspects of the present invention concern isolated DNA segments and recombinant vectors encoding CHTs, or more particularly human and mouse CHTs (HCHT and mCHT), as well as the creation and use of recombinant host cells through the application of DNA technology, that express a wild-type, polymorphic or mutant CHTs. Other aspects of the present invention concern isolated DNA segments and recombinant vectors encoding hCHT and mCHT inhibitors. Sequences of SEQ ID NO:1, SEQ ID NO:3 and biologically functional equivalents thereof are used in the current invention. The DNA segments and recombinant vectors encoding CHTs can be used in the invention, for example for creating dominant negatives, for screening of candidate substances and determining the effects of gene disruption on tolerance and dependence.

The present invention concerns DNA segments, isolatable from mammalian cells, such as mouse or human cells, that are free from total genomic DNA and that are capable of expressing a protein, polypeptide or peptide that has hCHT or mCHT activity or is capable of inhibiting CHT, or more particularly HCHT or mCHT. As used herein, the term "DNA segment" refers to a DNA molecule that has been isolated free of total genomic DNA of a particular species. Therefore, a DNA segment encoding CHT refers to a DNA segment that contains wild-type, polymorphic or mutant CHT coding sequences yet is isolated away from, or purified free from, total mammalian genomic DNA. Included within the term "DNA segment," are DNA segments and smaller fragments of such segments, and also recombinant vectors, including, for example, plasmids, cosmids, phage, viruses, and the like.

Similarly, a DNA segment comprising an isolated or purified hCHT or mCHT gene refers to a DNA segment including hCHT or mCHT protein, polypeptide or peptide coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and engineered segments that express, or may be adapted to express, proteins, polypeptides, domains, peptides, fusion proteins and mutants of CHT encoded sequences.

"Isolated substantially away from other coding sequences" means that the gene of interest, in this case the CHT, or more particularly hCHT or mCHT genes, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a CHT protein, polypeptide or peptide that includes within its amino acid sequence a contiguous amino acid sequence in accordance with, or essentially as set forth in SEQ ID NO: 2, corresponding to the hCHT designated "human CHT" and as set forth in SEQ ID NO: 4, corresponding to the mCHT designated "mouse CHT".

The term "a sequence essentially as set forth in SEQ ID NO: 2" means, for example, that the sequence substantially corresponds to a portion of SEQ ID NO: 2 and has relatively few amino acids that are not identical to, or a biologically functional equivalent of, the amino acids of SEQ ID NO: 2. This applies with respect to the other peptide or polypeptide sequences herewith.

The term "biologically functional equivalent" is well understood in the art and is further defined in detail herein. Accordingly, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 990%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO: 2 will be sequences that are "essentially as set forth in SEQ ID NO: 2, provided the biological activity of the protein is maintained. In particular embodiments, the biological activity of a hCHT or mCHT protein, polypeptide or peptide, or a biologically functional equivalent, comprises binding to one or more proteases. In specific embodiments, the biological activity of a hCHT or mCHT protein, polypeptide or peptide, or a biologically functional equivalent, comprises inhibition of the activity of one or more proteases, through binding. A preferred protease activity that may be inhibited by a hCHT or mCHT protein, polypeptide or peptide, or a biologically functional equivalent, is inhibition of the ability or rate of protealytic cleavage catalyzed by the protease.

In certain other embodiments, the invention concerns isolated DNA segments and recombinant vectors that include within their sequence a nucleic acid sequence essentially as set forth in SEQ ID NO:1 or SEQ ID NO:3. The term "essentially as set forth in SEQ ID NO: 1" is used in the same sense as described above and means that the nucleic acid sequence substantially corresponds to a portion of SEQ ID NO:1 and has relatively few codons that are not identical, or functionally equivalent, to the codons of SEQ ID NO: 1. Again, DNA segments that encode proteins, polypeptide or peptides exhibiting hCHT or mCHT activity will be most preferred.

The term "functionally equivalent codon" is used herein to refer to codons that encode the same amino acid, such as the six codons for arginine and serine, and also refers to codons that encode biologically equivalent amino acids. For optimization of expression of hCHT or mCHT in human cells, the codons are shown in Table 2 in preference of use from left to right. Thus, the most preferred codon for alanine is thus "GCC," and the least is "GCG" (see Table 2 below). Codon usage for various organisms and organelles can be found at the website www.kazusa.or.jp/codon/, incorporated herein by reference, allowing one of skill in the art to optimize codon usage for expression in various organisms using the disclosures herein. Thus, it is contemplated that codon usage may be optimized for other animals, as well as other organisms such as a prokaryote (e.g., an eubacteria), an archaea, an eukaryote (e.g., a protist, a plant, a fungus, an animal), a virus and the like, as well as organelles that contain nucleic acids, such as mitochondria or chloroplasts, based on the preferred codon usage as would be known to those of ordinary skill in the art.

TABLE 2

Preferred Human DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |

TABLE 2-continued

Preferred Human DNA Codons

| Amino Acids | | | Codons | |
|---|---|---|---|---|
| Tryptophan | Trp | W | TGG | |
| Tyrosine | Tyr | Y | TAC | TAT |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of nucleotides that are identical to the nucleotides of SEQ ID NO:1 will be sequences that are "essentially as set forth in SEQ ID NO:1." This is also true for nucleotides of SEQ ID NO:3, etc.

a. Nucleic Acid Hybridization

The nucleic acid sequences disclosed herein also have a variety of uses, such as for example, utility as probes or primers in nucleic acid hybridization embodiments. Contiguous sequences from hCHT or mCHT sequences can be used, for example, to form dominant negatives of the hCHT or mCHT, used to screen for inhibitor function.

Naturally, the present invention also encompasses DNA segments that are complementary, or essentially complementary, to the sequence set forth in SEQ ID NO:1 or SEQ ID NO:3. Nucleic acid sequences that are "complementary" are those that are capable of base-pairing according to the standard Watson-Crick complementarily rules. As used herein, the term "complementary sequences" means nucleic acid sequences that are complementary, as may be assessed by the same nucleotide comparison set forth above, or as defined as being capable of hybridizing to the nucleic acid segment of SEQ ID NO:1 or SEQ ID NO:3 under stringent conditions such as those described herein.

As used herein, "hybridization," "hybridizes" or "capable of hybridizing" is understood to mean the forming of a double or triple stranded molecule or a molecule with partial double or triple stranded nature. The term "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. For example, a medium stringency condition could be provided by about 0.1 to 0.25 M NaCl at temperatures of about 37° C. to about 55° C. Under these conditions, hybridization may occur even though the sequences of probe and target strand are not perfectly complementary, but are mismatched at one or more positions. In another example, a low stringency condition could be provided by about 0.15 M to about 0.9 M salt, at temperatures ranging from about 20° C. to about 55° C. Of course, it is within the skill of one in the art to further modify the low or high stringency conditions to suit a particular application. For example, in other embodiments, hybridization may be achieved under conditions of 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

Accordingly, the nucleotide sequences of the disclosure may be used for their ability to selectively form duplex molecules with complementary stretches of genes or RNAs or to provide primers for amplification of DNA or RNA from tissues. Depending on the application envisioned, it is preferred to employ varying conditions of hybridization to achieve varying degrees of selectivity of probe towards target sequence.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a contiguous stretch of nucleotides identical to or complementary to SEQ ID NO:1 or SEQ ID NO:3, such as, for example, about 8, about 10 to about 14, or about 15 to about 20 nucleotides, and that are chromosome sized pieces, up to about 1,000,000, about 750,000, about 500,000, about 250,000, about 100,000, about 50,000, about 20,000, or about 10,000, or about 5,000 base pairs in length, with segments of about 3,000 being preferred in certain cases, as well as DNA segments with total lengths of about 1,000, about 500, about 200, about 100 and about 50 base pairs in length (including all intermediate lengths of these lengths listed above, i.e., any range derivable therein and any integer derivable therein such a range) are also contemplated to be useful.

For example, it will be readily understood that "intermediate lengths," in these contexts, means any length between the quoted ranges, such as 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 130, 140, 150, 160, 170, 180, 190, including all integers through the 200-500; 500-1,000; 1,000-1500, 1600, 1700, 1743, and up to 2,000; 2,000-3,000; 3,000-5,000; 5,000-10,000 ranges, up to and including sequences of about 12,001, 12,002, 13,001, 13,002, 15,000, 20,000 and the like.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

$$n \text{ to } n+y$$

where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

The use of a hybridization probe of between 17 and 100 nucleotides in length, or in some aspect of the invention even up to 1-2 Kb or more in length, allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having complementary sequences over stretches of 20 to 30 nucleotides, or even longer where desired. Such fragments may be readily prepared by, for example, directly synthesizing the fragment by chemical means or by introducing selected sequences into recombinant vectors for recombinant production.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then, subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

b. Nucleic Acid Amplification

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to hCHT or mCHT genes are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label, or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products, and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification method described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double-stranded DNA molecules are heat denatured again. In either case, the single-stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single-stranded DNA, which is then converted to double-stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated herein by reference).

Methods based on ligation of two (or more) oligonucleotides in the presence of nucleic acid having the sequence of the resulting "di-oligonucleotide," thereby amplifying the di-oligonucleotide, may also be used in the amplification step of the present invention.

c. Nucleic Acid Detection

In certain embodiments, it will be advantageous to employ nucleic acid sequences of the present invention such as all or part of SEQ ID NO:1 or SEQ ID NO:3, or an hCHT or mCHT nucleic acid inhibitor in combination with an appropriate means, such as a label, for hybridization assays, RNase protection and Northern hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a detection means visible to the human eye or spectrophotometrically, to identify specific hybridization with complementary nucleic acid-containing samples.

In embodiments wherein nucleic acids are amplified, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols (see Sambrook et al, 1989). Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods for genetic screening to accurately detect mutations in genomic DNA, cDNA or RNA samples may be employed, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR™ (see above) and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of an *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches; provided the enzyme level is sufficiently high.

The RNase protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild-type sequences are hybridized to complementary target regions derived from test samples. The test target generally comprises DNA (either genomic DNA or DNA amplified by cloning in plasmids or by PCR™), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

d. Cloning hCHT or mCHT Genes

The present invention contemplates cloning CHT, or more particularly hCHT or mCHT genes or cDNAs from animal (e.g., mammalian) organisms. A technique often employed by those skilled in the art of protein production today is to obtain a so-called "recombinant" version of the protein, to express it in a recombinant cell and to obtain the protein, polypeptide or peptide from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule.

The first step in such cloning procedures is the screening of an appropriate DNA library, such as, for example, from a mouse, rat, monkey or human. The screening protocol may utilize nucleotide segments or probes that are designed to hybridize to cDNA or genomic sequences of CHTs from protists. Additionally, antibodies designed to bind to the expressed CHT proteins, polypeptides, or peptides may be used as probes to screen an appropriate mammalian DNA expression library. Alternatively, activity assays may be employed. The operation of such screening protocols are well known to those of skill in the art and are described in detail in the scientific literature, for example, in Sambrook et al. (1989), incorporated herein by reference. Moreover, as the present invention encompasses the cloning of genomic segments as well as cDNA molecules, it is contemplated that suitable genomic cloning methods, as known to those in the art, may also be used.

As used herein "designed to hybridize" means a sequence selected for its likely ability to hybridize to a mammalian CHT gene, for example due to the expected high degree of homology between the human CHT gene and the CHT genes from other mammals. Also included are segments or probes altered to enhance their ability to hybridize to or bind to a mammalian CHT gene. Additionally, these regions of homology also include amino acid sequences of 4 or more consecutive amino acids selected and/or altered to increase conservation of the amino acid sequences in comparison to the same or similar region of residues in the same or related genes in one or more species. Such amino acid sequences may derived from amino acid sequences encoded by the CHT gene and particularly from the isolated sequences of SEQ ID NO:2 or SEQ ID NO:4.

General methods for screening a mammalian DNA library are exemplified by, but not limited to, the methods detailed in Example I herein below. Nucleotide probes may derived from nucleotide sequences from the human or mouse CHT sequence, and more particularly from the isolated sequences of SEQ ID NO:1 or SEQ ID NO:3. Such sequences may be used as probes for hybridization or oligonucleotide primers for PCR™. Designing such sequences may involve selection of regions of highly conserved nucleotide sequences between various species for a particular gene or related genes, relative to the general conservation of nucleotides of the gene or related genes in one or more species. Comparison of the amino acid sequences conserved between one or more species for a particular gene may also be used to determine a group of 4 or more consecutive amino acids that are conserved relative to the protein encoded by the gene or related genes. The nucleotide probe or primers may then be designed from the region of the gene that encodes the conserved sequence of amino acids.

One may also prepare fusion proteins, polypeptides and peptides, e.g., where the hCHT or mCHT proteinaceous material coding regions are aligned within the same expression unit with other proteins, polypeptides or peptides having desired functions, such as for purification or immunodetection purposes (e.g., proteinaceous compostions that may be purified by affinity chromatography and enzyme label coding regions, respectively).

Encompassed by the invention are DNA segments encoding relatively small peptides, such as, for example, peptides of from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 40, about 45, to about 50 amino acids in length, and more preferably, of from about 15 to about 30 amino acids in length; as set forth in SEQ ID NO:2 or SEQ ID NO:4 and also larger polypeptides up to and including proteins corresponding to the full-length sequences set forth in SEQ ID NO:2 or SEQ ID NO:4, and any range derivable therein and any integer derivable therein such a range. In addition to the "standard" DNA and RNA nucleotide bases, modified bases are also contemplated for use in particular applications of the present invention. A table of exemplary, but not limiting, modified bases is provided herein below.

TABLE 3

Modified Bases

| Abbr. | Modified base description |
|---|---|
| ac4c | 4-acetylcytidine |
| chm5u | 5-(carboxyhydroxylmethyl)uridine |
| Cm | 2'-O-methylcytidine |
| Cmnm5s2u | 5-carboxymethylaminomethyl-2-thiondine |
| Cmnm5u | 5-carboxymethylaminomethyluridine |
| D | Dihydrouridine |
| Fm | 2'-O-methylpseudouridine |
| gal q | Beta,D-galactosylqueosine |
| Gm | 2'-O-methylguanosine |
| I | Inosine |
| I6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2 methylguanosine |
| m3c | 3-methylcytidine |
| m5c | 5-methylcytidine |
| m6a | N6-methyladenosine |
| m7g | 7-methylguanosine |
| Mam5u | 5-methylaminomethyluridine |
| Mam5s2u | 5-methoxyaminomethyl-2-thiouridine |
| Man q | Beta,D-mannosylqueosine |
| Mcm5s2u | 5-methoxycarbonylmethyl-2-thiouridine |

TABLE 3-continued

Modified Bases

| Abbr. | Modified base description |
|---|---|
| Mcm5u | 5-methoxycarbonylmethyluridine |
| Mo5u | 5-methoxyuridine |
| Ms2i6a | 2-methylthio-N6-isopentenyladenosine |
| Ms2t6a | N-((9-beta-D-ribofuranosyl-2-methylthiopurine-6-yl)carbamoyl)threonine |
| Mt6a | N-((9-beta-D-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine |
| Tm | 2'-O-methyl-5-methyluridine |
| Um | 2'-O-methyluridine |
| Yw | Wybutosine |
| X | 3-(3-amino-3-carboxypropyl)uridine, (acp3)u |

VI. Recombinant Vectors, Host Cells and Expression

Recombinant vectors form an important further aspect of the present invention. The term "expression vector or construct" means any type of genetic construct containing a nucleic acid coding for a gene product in which part or all of the nucleic acid encoding sequence is capable of being transcribed. The transcript may be translated into a proteinaceous molecule, but it need not be, such as in the case of hCHT or mCHT antisense inhibitors. Thus, in certain embodiments, expression includes both transcription of a CHT gene and translation of a RNA into the CHT gene product. In other embodiments, expression only includes transcription of the nucleic acid, for example, to generate antisense constructs. The antisense construct can be, for example a CHT antisense nucleic acid. A recombinant vector can also be used for delivery of the hCHT or mCHT of the current invention.

Particularly useful vectors are contemplated to be those vectors in which the coding portion of the DNA segment, whether encoding a full length protein or smaller polypeptide or peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

The promoter may be in the form of the promoter that is naturally associated with an CHT, or more particularly hCHT or mCHT gene, as may be obtained by isolating the 5' non-coding sequences located upstream of the coding segment or exon, for example, using recombinant cloning and/or PCR™ technology, in connection with the compositions disclosed herein (PCR™ technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an hCHT or mCHT gene in its natural environment. Such promoters may include promoters normally associated with other genes, and/or promoters isolated from any other bacterial, viral, eukaryotic, protist, or mammalian cell, and/or promoters made by the hand of man that are not "naturally occurring," i.e., containing different elements from different promoters, or mutations that increase, decrease, or alter expression.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment, such as is advantageous in the large-scale production of recombinant proteins, polypeptides or peptides.

At least one module in a promoter generally functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase promoter, the spacing between promoter elements can be increased to 50 base pairs apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various other embodiments, the human cytomegalovirus (CMV) immediate early gene promoter, the SV40 early promoter and the Rous sarcoma virus long terminal repeat can be used to obtain high-level expression of the instant nucleic acids. The use of other viral or mammalian cellular or bacterial phage promoters which are well-known in the art to achieve expression are contemplated as well, provided that the levels of expression are sufficient for a given purpose. Tables 4 and 5 below list several elements/promoters which may be employed, in the context of the present invention, to regulate the expression of an hCHT or mCHT gene. This list is not intended to be exhaustive of all the possible elements involved in the promotion of expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB, www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 4

Promoter and Enhancer Elements

| Promoter/Enhancer | References |
|---|---|
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1984; Kiledjian et al., 1988; Porton et al.; 1990 |
| Immunoglobulin Light Chain | Queen and Baltimore, 1983; Picard and Schaffner, 1984 |
| T-Cell Receptor | Luria et al., 1987; Winoto and Baltimore, 1989; Redondo et al.; 1990 |
| HLA DQ a and DQ β | Sullivan and Peterlin, 1987 |
| β-Interferon | Goodbourn et al., 1986; Fujita et al., 1987; Goodbourn and Maniatis, 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase | Jaynes et al., 1988; Horlick and Benfield, 1989; Johnson et al., 1989 |
| Prealbumin (Transthyretin) | Costa et al., 1988 |
| Elastase I | Ornitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | |
| c-HA-ras | Deschamps et al., 1985 |
| Insulin | Edlund et al., 1985 |
| Neural Cell Adhesion Molecule (NCAM) | Hirsh et al., 1990 |

TABLE 4-continued

Promoter and Enhancer Elements

| Promoter/Enhancer | References |
|---|---|
| $\alpha_{1\text{-Antitrypain}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |
| Polyoma | Swartzendruber and Lehman, 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Choi et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 5

Inducible Elements

| Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987; Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | Ela | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

Turning to the expression of the hCHT or mCHT proteinaceous molecules of the present invention, once a suitable clone or clones have been obtained, whether they be cDNA based or genomic, one may proceed to prepare an expression system. The engineering of DNA segment(s) for expression in a prokaryotic or eukaryotic system may be performed by techniques generally known to those of skill in recombinant expression. It is believed that virtually any expression system may be employed in the expression of the proteinaceous molecules of the present invention.

Both cDNA and genomic sequences are suitable for eukaryotic expression, as the host cell will generally process the genomic transcripts to yield functional mRNA for translation into proteinaceous molecules. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

a. Antisense and Ribozymes

In some embodiments of the invention, an antisense nucleic acid can be used as an hCHT or mCHT inhibitor. The term "antisense nucleic acid" is intended to refer to the oligonucleotides complementary to the base sequences of DNA and RNA. Antisense oligonucleotides, when introduced into a target cell, specifically bind to their target nucleic acid and interfere with transcription, RNA processing, transport, translation, and/or stability. Targeting double-stranded (ds) DNA with oligonucleotides leads to triple-helix formation; targeting RNA will lead to double-helix formation. An antisense nucleic acid may be complementary to SEQ ID NO:1 or SEQ ID NO:3, complementary to an CHT encoding sequence or to CHT non-coding sequences.

Targeting double-stranded (ds) DNA with polynucleotides leads to triple-helix formation; targeting. RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries (splice junctions) of a gene. It is contemplated that the most effective antisense constructs may include regions complementary to intron/exon splice junctions. Thus, antisense constructs with complementary regions within 50-200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligo-nucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro or in vivo to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids. Sequences for ribozymes may be included in the DNA template to eliminate undesired 5' end sequences in RNAs generated through T7 RNA polymerase transcription.

Ribozymes are RNA-protein complexes that cleave nucleic acids in a site-specific fashion. Ribozymes have specific catalytic domains that possess endonuclease activity (Kim and Cech, 1987; Gerlack et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Several different ribozyme motifs have been described with RNA cleavage activity (reviewed in Symons, 1992). Examples that would be expected to function equivalently for the up or down regulation of hCHTs and mCHTs include sequences from the Group I self-splicing introns including tobacco ringspot virus (Prody et al., 1986), avocado sunblotch viroid (Palukaitis et al., 1979; Symons, 1981), and Lucerne transient streak virus (Forster and Symons, 1987).

Sequences from these and related viruses are referred to as hammerhead ribozymes based on a predicted folded secondary structure.

Other suitable ribozymes include sequences from RNase P with RNA cleavage activity (Yuan, et al., 1992; Yuan and Altman, 1994), hairpin ribozyme structures (Berzal-Herranz, et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complementary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., 1992; Thompson, et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in hCHT- and mCHT-targeted ribozymes is simply a matter of preparing and testing a given sequence, and is a routinely practiced "screening" method known to those of skill in the art.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

It is proposed that CHT, or more particularly hCHT or mCHT may be co-expressed with other selected proteinaceous molecules, wherein the proteinaceous molecules may be co-expressed in the same cell or hCHT or mCHT gene may be provided to a cell that already has another selected proteinaceous molecule. Co-expression may be achieved by co-transfecting the cell with two distinct recombinant vectors, each bearing a copy of either of the respective DNAs. Alternatively, a single recombinant vector may be constructed to include the coding regions for both of the proteinaceous molecules, which could then be expressed in cells transfected with the single vector. In either event, the term "co-expression" herein refers to the expression of both the hCHT or mCHT gene and the other selected proteinaceous molecules in the same recombinant cell.

As used herein, the terms "engineered" and "recombinant" cells or host cells are intended to refer to a cell into which an exogenous DNA segment or gene, such as a cDNA or gene encoding hCHT or mCHT, has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant hCHT or mCHT protein kinase, whether mutant or wild-type, in accordance with the present invention one would prepare an expression vector that comprises a wild-type, or mutant CHT proteinaceous molecule-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter directs transcription of the DNA and promotes expression of the encoded recombinant protein, polypeptide or peptide. This is the meaning of "recombinant expression" in this context.

Many standard techniques are available to construct expression vectors containing the appropriate nucleic acids and transcriptional/translational control sequences in order to achieve protein, polypeptide or peptide expression in a variety of host-expression systems. Cell types available for expression include, but are not limited to, bacteria, such as *E. coli* and *B. subtilis*, transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W31 10 (F—, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication origin, as well as marking sequences which are capable of providing phenotypic selection in transformed cells. For example, *E. coli* is often transformed using derivatives of pBR322, a plasmid derived from an *E. coli* species pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media, for example, LB. The expression of the recombinant proteinaceous molecule may be induced, e.g., by adding IPTG or any appropriate inducer to the media or by switching incubation to a higher temperature, depending on the regulated promoter used. After culturing the bacteria for a further period, generally of between 2 and 24 hours, the cells are collected by centrifugation and washed to remove residual media.

The bacterial cells are then lysed, for example, by disruption in a cell homogenizer, by sonication or cell press and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant proteinaceous molecule is expressed in the inclusion bodies, as is the case in many instances, these can be washed in any of several solutions to remove some of the contaminating host proteins, then solubilized in solutions containing high concentrations of urea (e.g., 8M) or chaotropic agents such as guanidine hydrochloride in the presence of reducing agents, such as β-mercaptoethanol or DTT (dithiothreitol).

Under some circumstances, it may be advantageous to incubate the proteinaceous molecule for several hours under conditions suitable for the proteinaceous molecule to undergo a refolding process into a conformation which more closely resembles that of the native proteinaceous molecule. Such conditions generally include low proteinaceous molecule concentrations, less than 500 mg/ml, low levels of reducing agent, concentrations of urea less than 2 M and often the presence of reagents such as a mixture of reduced and oxidized glutathione which facilitate the interchange of disulfide bonds within the proteinaceous molecule.

The refolding process can be monitored, for example, by SDS-PAGE, or with antibodies specific for the native molecule (which can be obtained from animals vaccinated with the native molecule or smaller quantities of recombinant proteinaceous molecule). Following refolding, the proteinaceous molecule can then be purified further and separated from the refolding mixture by chromatography on any of several supports including ion exchange resins, gel permeation resins or on a variety of affinity columns.

For expression in *Saccharomyces*, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoter sequences in yeast vectors include the promoters for 3-phosphoglycerate kinase or other glycolytic enzymes, such as enolase, glyceraldehyde-3-phosphate-hCHT, glyceraldehyde-3-phosphate protein, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol hCHT 2, isocytochrome C, acid phosphatase, degradative enzymes associated with nitrogen metabolism, and the aforementioned glyceraldehyde-3-phosphate-hCHT, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more hCHT or mCHT coding sequences.

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of proteinaceous products may be important for the function of the proteinaceous molecule.

Different host cells have characteristic and specific mechanisms for the post-translational processing and modification of proteinaceous molecules. Appropriate cells lines or host systems can be chosen to ensure the correct modification and processing of the foreign proteinaceous molecule expressed.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the hCHT or mCHT gene, provided such control sequences are compatible with the host cell systems.

A number of viral-based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1, E3, or E4) will result in a recombinant virus that is viable and capable of expressing hCHT or mCHT in infected hosts.

Specific initiation signals may also be required for efficient translation of hCHT or mCHT protein, polypeptide or peptide coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements and transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the proteinaceous molecule at a position prior to transcription termination.

For long-term, high-yield production of a recombinant hCHT or mCHT protein, polypeptide or peptide, stable expression is preferred. For example, cell lines that stably express constructs encoding an hCHT or mCHT protein, polypeptide or peptide may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (tk), hypoxanthine-guanine phosphoribosyltransferase (hgprt) and adenine phosphoribosyltransferase (aprt) genes, in tk–, hgprt– or aprt– cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and hygromycin (hygro), that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower proteinaceous molecule production than adherent cells.

Large scale suspension culture of mammalian cells in stirred tanks is a common method for production of recombinant proteinaceous molecules. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the hCHT or mCHT proteins, polypeptides or peptides of the invention may be "overexpressed," i.e., expressed in increased levels relative to its natural expression in cells. Such overexpression may be assessed by a variety of methods, including radio-labeling and/or proteinaceous molecule purification. However, simple and direct methods are preferred, for example, those involving SDS/PAGE and proteinaceous composition staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific proteinaceous molecule in relation to the other proteins produced by the host cell and, e.g., visible on a gel.

VII. Methods of Gene Transfer

In order to mediate the effect of transgene expression in a cell, it will be necessary to transfer the expression constructs (e.g., a therapeutic construct) of the present invention into a cell. Such transfer may employ viral or non-viral methods of gene transfer. This section provides a discussion of methods and compositions of gene or nucleic acid transfer, including transfer of antisense sequences.

The hCHT or mCHT genes are incorporated into a viral vector to mediate gene transfer to a cell. Additional expression constructs encoding other therapeutic agents as described herein may also be transferred via viral transduction using infectious viral particles, for example, by transformation with an adenovirus vector of the present invention. Alternatively, a retrovirus, bovine papilloma virus, an adeno-associated virus (AAV), a lentiviral vector, a vaccinia virus, a polyoma virus, or an infective virus that has been engineered to express a specific binding ligand may be used. Similarly, nonviral methods which include, but are not limited to, direct delivery of DNA such as by injection, electroporation, calcium phosphate precipitation, liposome mediated transfection, and microprojectile bombardment may be employed. Thus, in one example, viral infection of cells is used in order to deliver therapeutically significant genes to a cell. Typically, the virus simply will be exposed to the appropriate host cell under physiologic conditions, permitting uptake of the virus.

a. Adenoviral Vectors

A particular method for delivery of the expression constructs for hCHT or mCHT inhibition involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and/or (b) to ultimately express a tissue and/or cell-specific construct that has been cloned therein.

The expression vector comprises a genetically engineered form of adenovirus. Knowledge of the genetic organization and/or adenovirus, a 36 kb, linear, double-stranded DNA virus, allows substitution of large pieces of adenoviral DNA with foreign sequences up to 7 kb (Grunhaus and/or Horwitz, 1992). In contrast to retrovirus, the adenoviral infection of host cells: does not result in chromosomal integration because adenoviral DNA can replicate in an episomal manner without potential genotoxicity. Also, adenoviruses are structurally stable, and/or no genome rearrangement has been detected after extensive amplification.

Adenovirus is particularly suitable for use as a gene transfer vector because of its mid-sized genome, ease of manipulation, high titer, wide target-cell range and/or high infectivity. Both ends of the viral genome contain 100-200 base pair inverted repeats (ITRs), which are cis elements necessary for viral DNA replication and/or packaging. The early (E) and/or late (L) regions of the genome contain different transcription units that are divided by the onset of viral DNA replication. The E1 region (E1A and/or E1B) encodes proteins responsible for the regulation of transcription of the viral genome and/or a few cellular genes. The expression of the E2 region (E2A and/or E2B) results in the synthesis of the proteins for viral DNA replication. These proteins are involved in DNA replication, late gene expression and/or host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and/or all the mRNA's issued from this promoter possess a 5'-tripartite leader (TPL) sequence which makes them preferred mRNA's for translation.

In a current system, recombinant adenovirus is generated from homologous recombination between shuttle vector and/or provirus vector. Due to the possible recombination between two proviral vectors, wild-type adenovirus may be generated from this process. Therefore, it is critical to isolate a single clone of virus from an individual plaque and/or examine its genomic structure.

Generation and/or propagation of the current adenovirus vectors, which are replication deficient, depend on a unique helper cell line, designated 293, which was transformed from human embryonic kidney cells by Ad5 DNA fragments and/or constitutively expresses E1 proteins (E1A and/or E1B. Graham et al, 1977). Since the E3 region is dispensable from the adenovirus genome (Jones and/or Shenk, 1978), the current adenovirus vectors, with the help of 293 cells, carry foreign DNA in either the E1, the D3 and/or both regions (Graham and/or Prevec, 1991). Recently, adenoviral vectors comprising deletions in the E4 region have been described (U.S. Pat. No. 5,670,488, incorporated herein by reference).

In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and/or E3 regions, the maximum capacity of the current adenovirus vector is under 7.5 kb, and/or about 15% of the total length of the vector. More than 80% of the adenovirus viral genome remains in the vector backbone.

Helper cell lines may be derived from human cells such as embryonic kidney cells, muscle cells, hematopoietic cells and/or other embryonic mesenchymal and/or epithelial cells. Alternatively, the helper cells may be derived from the cells of other mammalian species that are permissive for human adenovirus. Such cells include, e.g., Vero cells and/or other monkey embryonic mesenchymal and/or epithelial cells.

Recently, Racher et al. (1995) disclosed improved methods for culturing 293 cells and/or propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and/or left stationary, with occasional agitation, for 1 to 4 h. The medium is then replaced with 50 ml of fresh medium and/or shaking initiated. For virus production, cells are allowed to grow to about 80% confluence, after which time the medium is replaced (to 25% of the final volume) and/or adenovirus added at an MOI of 0.05. Cultures are left stationary overnight, following which the volume is increased to 100% and/or shaking commenced for another 72 h.

Other than the requirement that the adenovirus vector be replication defective, and/or at least conditionally defective, the nature of the adenovirus vector is not believed to be crucial to the successful practice of the invention. The adenovirus may be of any of the 42 different known serotypes and/or subgroups A-F. Adenovirus type 5 of subgroup C is the preferred starting material in order to obtain the conditional replication-defective adenovirus vector for use in the present invention. This is because Adenovirus type 5 is a adenovirus about which a great deal of biochemical and/or genetic information is known, and/or it has historically been used for most constructions employing adenovirus as a vector.

As stated above, the typical vector according to the present invention is replication defective and/or will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) and/or in the E4 region where a helper cell line and/or helper virus complements the E4 defect.

Adenovirus growth and/or manipulation is known to those of skill in the art, and/or exhibits broad host range in vitro and/or in vivo. This group of viruses can be obtained in high titers, e.g., $10^9$ to $10^{11}$ plaque-forming units per ml, and/or they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and/or therapeutic potential as in vivo gene transfer vectors.

Adenovirus vectors have been used in eukaryotic gene expression (Levrero et al., 1991; Gomez-Foix et al., 1992) and/or vaccine development (Grunhaus et al., 1992; Horwitz, 1992; Graham et al., 1992; Prevec, 1992). Recently, animal studies suggested that recombinant adenovirus could be used for gene therapy (Stratford-Perricaudet, 1991; Perricaudet, 1991a; Stratford-Perricaudet et al., 1991b; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz, 1993 Gerard, 1993) and/or stereotactic inoculation into the brain (Le Gal La Salle et al., 1993). Recombinant adenovirus and/or adeno-associated virus (see below) can both infect and/or transduce non-dividing hyman primary cells.

b. AAV Vectors

Adeno-associated virus (AAV) is an attractive vector system for use in the cell transduction of the present invention as it has a high frequency of integration and/or it can infect nondividing cells, thus making it useful for delivery of genes into mammalian cells, for example, in tissue culture (Muzyczka, 1992) and/or in vivo. AAV has a broad host range for infectivity (Tratschin et al., 1984; Laughlin et al., 1986; Lebkowski et al., 1988; McLaughlin et al., 1988). Details concerning the generation and/or use of rAAV vectors are described in U.S. Pat. No. 5,139,941 and/or U.S. Pat. No. 4,797,368, each incorporated herein by reference.

Studies demonstrating the use of AAV in gene delivery include LaFace et al. (1988); Zhou et al. (1993); Flotte et al. (1993); and/or Walsh et al. (1994). Recombinant AAV vectors have been used successfully for in vitro and/or in vivo transduction of marker genes (Kaplitt et al., 1994; Lebkowski et al., 1988; Samulski et al., 1989; Yoder et al., 1994; Zhou et al., 1994; Hermonat, 1984; Muzyczka, 1984; Tratschin et al., 1985; McLaughlin et al., 1988) and/or genes involved in human diseases (Flotte et al., 1992; Luo et al., 1994; Ohi et al., 1990; Walsh et al., 1994; Wei et al., 1994).

AAV is a dependent parvovirus in that it requires coinfection with another virus (either adenovirus and/or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991) rAAV, however, is not restricted to chromosome 19 for integration unless the AAV Rep protein is also expressed (Shelling, 1994; Smith, 1994). When a cell carrying an AAV provirus is superinfected with a helper virus, the AAV genome is "rescued" from the chromosome and/or from a recombinant plasmid, and/or a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and/or an expression plasmid containing the wild type AAV coding sequences without the terminal repeats, for example pIM45 (McCarty et al., 1991; incorporated herein by reference). The cells are also infected and/or transfected with adenovirus and/or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions and/or cell lines containing the AAV coding regions and/or some and/or all of the adenovirus helper genes could be used (Yang et al., 1994; Clark et al., 1995). Cell lines carrying the rAAV DNA as an integrated provirus can also be used (Flotte et al., 1995).

c. Retroviral Vectors

Retroviruses have promise as gene delivery vectors due to their ability to integrate their genes into the host genome, transferring a large amount of foreign genetic material, infecting a broad spectrum of species and/or cell types and/or of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and/or directs synthesis of viral proteins. The integration results in the retention of the viral gene sequences in the recipient cell and/or its descendants. The retroviral genome contains three genes, gag, pol, and/or env that code for capsid proteins, polymerase enzyme, and/or envelope components, respectively. A sequence found upstream from the gag gene contains a signal for packaging of the genome into virions. Two long terminal repeat (LTR) sequences are present at the 5' and/or 3' ends of the viral genome. These contain strong promoter and/or enhancer sequences and/or are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and/or env genes but without the LTR and/or packaging components is constructed (Mann et al., 1983). When a recombinant plasmid containing a cDNA, together with the retroviral LTR and/or packaging sequences is introduced into this cell line (by calcium phosphate precipitation for example), the packaging sequence allows the RNA transcript of the recombinant plasmid to be packaged into viral particles, which are then secreted into the culture media (Nicolas and/or Rubenstein, 1988; Temin, 1986; Mann et al., 1983). The media containing the recombinant retroviruses is then collected, optionally concentrated, and/or used for gene transfer. Retroviral vectors are able to infect a broad variety of cell types. However, integration and/or stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and/or modified an envelope protein so that the virus specifically bound to, and/or infected cells bearing the erythropoietin (EPO) receptor. This was achieved by inserting a portion of the EPO sequence into an envelope protein to create a chimeric protein with a new binding specificity.

d. Herpesvirus

Because herpes simplex virus (HSV) is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see (Glorioso et al., 1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotide reductase, a DNA polymerase, a ssDNA binding protein, a helicase/primase, a DNA dependent ATPase, dUTPase and others.

HSV genes from several groups whose expression is coordinately regulated and sequentially ordered in a cascade fashion (Honess and Roizman, 1974; Honess and Roizman, 1975; Roizman and Sears, 1995). The expression of a genes, the first set of genes to be expressed after infection, is enhanced by the virion protein number 16, or α-transducing factor (Post et al., 1981; Batterson and Roizman, 1983; Campbell et al., 1983). The expression of β genes requires functional γ gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene therapy contexts (U.S. Pat. No. 5,672,344).

e. Lentiviral Vectors

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997), U.S. Pat. Nos. 6,013,516 and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine 10 leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts.

Typical selection genes encode proteins that confer resistance to antibiotics and other toxic substances, e.g., histidinol, puromycin, hygromycin, neomycin, methotrexate, etc. and cell surface markers.

The vectors are introduced via transfection or infection into the packaging cell line. The packaging cell line produces viral particles that contain the vector genome. Methods for transfection or infection are well known by those of skill in the art. After 30 cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

f. Vaccinia Virus

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral, thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

g. Polyoma viruses

The empty capsids of papovaviruses, such as the mouse polyoma virus, have received attention as possible vectors for gene transfer (Barr et al., 1979), first described the use of polyoma empty when polyoma DNA and purified empty capsids were incubated in a cell-free system. The DNA of the new particle was protected from the action of pancreatic DNase. Slilaty and Aposhian (1983) described the use of those reconstituted particles for transferring a transforming polyoma DNA fragment to rat FIII cells. The empty capsids and reconstituted particles consist of all three of the polyoma capsid antigens VP1, VP2 and VP3 and there is no suggestion that pseudocapsids consisting of only the major capsid antigen VP1, could be used in genetic transfer.

Montross et al., (1991), described only the major capsid antigen, the cloning of the polyoma virus VP1 gene and its expression in insect cells. Self-assembly of empty pseudocapsids consisting of VP1 is disclosed, and pseudocapsids are said not to contain DNA. It is also reported that DNA inhibits the in vitro assembly of VP1 into empty pseudocapsids, which suggests that said pseudocapsids could not be used to package exogenous DNA for transfer to host cells. The results of (Sandig et al., 1993), showed that empty capsids incorporating exogenous DNA could transfer DNA in a biologically functional manner to host cells only if the particles consisted of all three polyoma capsid antigens VP1, VP2 and VP3. Pseudocapsids consisting of VP1 were said to be unable to transfer to exogenous DNA so that it could be expressed in the host cells, probably due the absence of $Ca^{2+}$ ions in the medium in which the pseudocapsids were prepared. Haynes et al. (1993) discuss the effect of calcium ions on empty VP1 pseudocapsid assembly.

U.S. Pat. No. 6,046,173 discloses the use of a pseudocapsid formed from papovavirus major capsid antigen and excluding minor capsid antigens, which pseudocapsid incorporates exogenous material for gene transfer.

h. Other Viral Vectors

Other viral vectors may be employed as expression constructs in the present invention. Vectors derived from viruses such as sindbis virus and/or cytomegalovirus. They offer several attractive features for various mammalian cells (Friedmann, 1989; Ridgeway, 1988; Baichwal and/or Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and/or reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and/or pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

i. Modified Viruses

In still further embodiments of the present invention, the nucleic acids to be delivered are housed within an infective virus that has been engineered to express a specific binding ligand. The virus particle will thus bind specifically to the cognate receptors of the target cell and/or deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and/or against a specific cell receptor were used. The antibodies were coupled via the biotin components by using streptavidin (Roux et al., 1989). Using antibodies against major histocompatibility complex class I and/or class II antigens, they demonstrated the infection of a variety of human cells that bore those surface antigens with an ecotropic virus in vitro (Roux et al., 1989).

j. Non-viral Transfer

DNA constructs of the present invention are generally delivered to a cell, in certain situations, the nucleic acid to be transferred is non-infectious, and can be transferred using non-viral methods.

Several non-viral methods for the transfer of expression constructs into cultured mammalian cells are contemplated by the present invention. Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945, 100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

VIII. Antibodies a. Antibody Generation

It will be understood that polyclonal or monoclonal antibodies specific for the CHT and related proteins will have utilities in several applications. These include, for example, the use of antibodies for controlling transport of CHT proteins to the brain. An additional use is to link such antibodies to therapeutic agents, and to administer the antibodies to individuals with a disease such as Parkinson's disease, Huntington's disease, Alzheimer's, schizophrenia or dysautonomia and thereby modulating CHT and treating the disease.

Thus the invention further provides antibodies specific for the CHT proteins, polypeptides or peptides, encoded by the nucleic acid segments disclosed herein and their equivalents. Means for preparing and characterizing antibodies are well known in the art (See, e.g., Antibodies: A Laboratory Manual, Cold Spring Harbor Laboratory, 1988, incorporated herein by reference) Antibodies to CHT peptides or protein have been generated using such standard techniques.

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimyde and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The procured blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix or protein A followed by antigen (peptide) affinity column for purification.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified CHT protein, polypeptide or peptide. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep, goat, monkey cells also is possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens or lymph nodes. Spleen cells and lymph node cells are preferred, the former because they are a rich source of antibody-producing cells that are in the dividing plasmablast stage.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984; each incorporated herein by reference). For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210- and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag-4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

One selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens such antibodies are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332 describes methods for the production of antibodies, or antibody fragments, which have the same binding specificity as a parent antibody but which have increased human characteristics. Humanized antibodies may be obtained by chain shuffling, perhaps using phage display technology, in as much as such methods will be useful in the present invention the entire text of U.S. Pat. No. 5,565,332 is incorporated herein by reference. Human antibodies may also be produced by transforming B cells with EBV and subsequent cloning of secretors as described by Hoon et al., (1993).

b. Cross-Reactive Antibodies and Epitopes

The invention further encompasses anti-CHT marker antibodies and antibody-based compositions, such as antibody conjugates and immunotoxins, that bind to the same antigens and/or epitopes as the antibodies disclosed herein (e.g., those raised to the peptides of SEQ ID NO:2 or SEQ ID NO:4). Such antibodies may be of the polyclonal or monoclonal type, with monoclonals being generally preferred.

The identification of an antibody that binds to CHT or an epitope thereof, in substantially the same manner as an antibody of the invention is a fairly straightforward matter. This can be readily determined using any one of variety of immunological screening assays in which antibody competition can be assessed.

For example, where the test antibodies to be examined are obtained from different source animals, or are even of a different isotype, a simple competition assay may be employed in which the control and test antibodies are premixed and then applied to an antigen composition. By "antigen composition" is meant any composition that contains a CHT or related antigen as described herein. Thus, protocols based upon ELISAs and Western blotting are suitable for use in such simple competition studies.

In such embodiments, one would pre-mix the control antibodies with varying amounts of the test antibodies (e.g., 1:1, 1:10 and 1:100) for a period of time prior to applying to an antigen composition, such as an antigen-coated well of an ELISA plate or an antigen adsorbed to a membrane (as in dot blots and Western blots). By using species or isotype secondary antibodies one will be able to detect only the bound control antibodies, the binding of which will be reduced by the presence of a test antibody that recognizes the same epitope/antigen.

In conducting an antibody competition study between a control antibody, such as an anti-CHT antibody, and any test antibody, one may first label the control with a detectable label, such as, e.g., biotin or an enzymatic, radioactive or fluorescent label, to enable subsequent identification. In these cases, one would incubate the labeled control antibodies with the test antibodies to be examined at various ratios (e.g., 1:1, 1:10 and 1:100) and, after a suitable period of time, one would then assay the reactivity of the labeled control antibodies and compare this with a control value in which no potentially competing test antibody was included in the incubation.

The assay may again be any one of a range of immunological assays based upon antibody hybridization, and the control antibodies would be detected by means of detecting their label, e.g., using streptavidin in the case of biotinylated antibodies or by using a chromogenic substrate in connection with an enzymatic label or by simply detecting a radioactive or fluorescent label. An antibody that binds to substantially the same epitope as the control antibodies will be able to effectively compete for binding and thus will significantly reduce control antibody binding, as evidenced by a reduction in bound label.

The reactivity of the labeled control antibodies in the absence of any test antibody would be the control high value. The control low value would be obtained by incubating the labeled antibodies with unlabelled antibodies of the same type, when competition would occur and reduce binding of the labeled antibodies. A significant reduction in labeled antibody reactivity in the presence of a test antibody is indicative of a test antibody that recognizes the same epitope, i.e., one that "cross-reacts" with the labeled antibody. A significant reduction is a reproducible, i.e., consistently observed, reduction in binding.

c. Antibody Conjugates

Antibody conjugates in which a CHT marker antibody is linked to a detectable label or a cytotoxic agent form further aspects of the invention. Diagnostic antibody conjugates may be used both in vitro diagnostics, as in a variety of immunoassays, and in vivo diagnostics, such as in imaging technology.

Certain antibody conjugates include those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat.

Nos. 3,817,837; 3,850,752; 3,939,350; 3,996,345; 4,277, 437; 4,275,149 and 4,366,241; each incorporated herein by reference.

D. Antibodies for Use In Vitro Also May be Radiolabeled Antibody Conjugates.

In using an antibody-based molecule as an in vivo diagnostic agent to provide an image of a tissue sample, magnetic resonance imaging, X-ray imaging, computerized emission tomography and such technologies may be employed. In the antibody-imaging constructs of the invention, the antibody portion used will generally bind to the antigen marker, such as CHT, and the imaging agent will be an agent detectable upon imaging, such as a paramagnetic, radioactive or fluorescent agent.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a.metal chelate complex employing, for example, an organic chelating agent such a DTPA attached to the antibody (U.S. Pat. No. 4,472,509). Monoclonal antibodies also may be reacted with an enzyme in the presence of a coupling agent such as glutaraldehyde or periodate. Conjugates with fluorescein markers are prepared in the presence of these coupling agents or by reaction with an isothiocyanate. Fluorescent labels include, but are not limited to rhodamine, fluorescein isothiocyanate and renographin.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99m}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as SNCl$_2$, a buffer solution such as sodium-potassium phthalate solution, and the antibody.

Intermediary functional groups which are often used to bind radioisotopes which exist as metallic ions to antibody are diethylenetriaminepentaacetic acid (DTPA) and ethylene diaminetetracetic acid (EDTA).

IX. Protein Purification

To prepare a composition comprising a CHT, or more preferentially, the hCHT or mCHT it may be desirable to purify the components or variants thereof. According to one embodiment of the present invention, purification of a peptide comprising the hCHT or mCHT can be utilized ultimately to operatively link this domain with a selective agent. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide, such as a hCHT or mCHT inhibitor. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition, such as the hCHT or mCHT inhibitor, that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

Ion exchange chromatography can be used as a method of separation. Using columns resins such as the metal affinity chromatography resin TALON are also preferred. TALON resin has an enhanced resolving power for polyhistidine-tagged proteins. This results in greater purity with less effort. TALON employs cobalt, an electropositive metal with a remarkably high affinity for polyhistidine-tagged proteins and a low affinity for other proteins. Often, no discernible binding of host proteins occurs and a separate wash step is not required. The binding properties of cobalt allow protein elution under mild pH conditions that protect protein integrity.

Further concentration of the proteins can be done on an anion exchange column, such as the MonoQ column, a high resolution, anion exchange column. This column works at pressures less than 5 MPa, has a high capacity and gives very high chromatographic resolution.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography, a particularly efficient method of purifying peptides, is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding, and it should be possible to elute the substance without destroying the sample or the ligand. One of the most common forms of affinity chromatography is immunoaffinity chromatography. The generation of antibodies that would be suitable for use in accord with the present invention.

a. Synthetic Peptides

The present invention also describes a hCHT or mCHT inhibitor, including an fusion protein, for use in various embodiments of the present invention. The peptides of the invention can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Peptides with at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95 or up to about 100 amino acid residues are contemplated by the present invention The compositions of the invention may include a peptide comprising a CHT, a CHT inhibitor, or a MEK that has been modified to enhance its activity or to render it biologically protected. Biologically protected peptides have certain advantages over unprotected peptides when administered to human subjects and, as disclosed in U.S. Pat. No. 5,028,592, incorporated herein by reference, protected peptides often exhibit increased pharmacological activity.

Compositions for use in the present invention may also comprise peptides that include all L-amino acids, all D-amino acids, or a mixture thereof. The use of D-amino acids may confer additional resistance to proteases naturally found within the human body and are less immunogenic and can therefore be expected to have longer biological half lives.

b. Protein Modification for Purification

Thirteen transmembrane domains have been predicted for the hCHT protein. Because transmembrane domains are hydrophobic and tend to make the purification and isolation of a protein more difficult, it is an aspect of the present invention that mutant proteins lacking one or more of the transmembrane domains be made by techniques described herein. These deletion varient CHTs can more easily be purified by the techniques described herein and those know in the art.

X. Recombinant Expression of CHT Peptides

Recombinant clones expressing the CHT nucleic acid segments may be used to prepare purified recombinant human CHT protein (hCHT), purified hCHT-derived peptide antigens as well as mutant or variant recombinant protein species in significant quantities. The selected antigens, and variants thereof, are proposed to have significant utility in diagnosing and treating neuromuscular, autonomic or CNS disorders. For example, it is proposed that hCHTs, peptide variants thereof, and/or antibodies against such hCHTs may also be used in immunoassays to detect the influence of cholinergic signaling or as vaccines or immunotherapeutics to treat diseases such as Parkinson's disease, Huntington's disease, Alzheimer's, schizophrenia and dysautonomia. Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be obtained from relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence.

XI. Screens: Modulators of Protein Function

The present invention further comprises methods for identifying modulators of the function of CHT. These assays may comprise random screening of large libraries of candidate substances; alternatively, the assays may be used to focus on particular classes of compounds selected with an eye towards structural attributes that are believed to make them more likely to modulate the function of CHT.

To identify a CHT modulator, one generally will determine the function of CHT in the presence and absence of the candidate substance, a modulator defined as any substance that alters function By function, it is meant that one may assay for the increase or decrease in high-affinity choline uptake. For example, a method generally comprises:
 (a) providing a candidate modulator;
 (b) admixing the candidate modulator with an isolated compound or cell, or a suitable experimental animal;
 (c) measuring one or more characteristics of the compound, cell or animal in step (c); and
 (d) comparing the characteristic measured in step (c) with the characteristic of the compound, cell or animal in the absence of said candidate modulator, wherein a difference between the measured characteristics indicates that said candidate modulator is, indeed, a modulator of the compound, cell or animal. Assays may be conducted in cell free systems, in isolated cells, or in organisms including transgenic animals such as transgenic mice.

It will, of course, be understood that all the screening methods of the present invention are useful in themselves notwithstanding the fact that effective candidates may not be found. The invention provides methods for screening for such candidates, not solely methods of finding them.

a. Modulators

As used herein the term "candidate substance" refers to any molecule that may potentially inhibit or enhance CHT activity. The candidate substance may be a protein or fragment thereof, a small molecule, or even a nucleic acid molecule. It may prove to be the case that the most useful pharmacological compounds will be compounds that are structurally related to hCHT or mCHT peptides. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on CHT. Regardless of the type of inhibitor or activator identified by the present screening methods, the effect of the inhibition or activator by such a compound results in altering CHT function as compared to that observed in the absence of the added candidate substance.

b. In vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

c. In cyto Assays

The present invention also contemplates the screening of compounds for their ability to modulate CHT in cells. Various cell lines can be utilized for such screening assays, including cells specifically engineered for this purpose.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

d. In vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

The present invention provides methods of screening for a candidate substance that modulate high-affinity choline uptake. In these embodiments, the present invention is directed to a method for determining the ability of a candidate substance to modulate HACU generally including the steps of administering a candidate substance to the animal; and determining the ability of the candidate substance to alter HACU and thereby alter Ach synthesis.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

e. Choline TransportAssay

A preferred method for screening for modulation of CHT function is a choline transport assay. The choline transport assay can be used to determine the effectiveness of candidate substances in the modulation of high-affinity choline uptake. The ion-dependence of choline transport can be determined by replacing $Na^+$ with equimolar concentrations of $Li^+$ and replacing Cl⁻ was replaced with equimolar concentrations of isethionate. Specific transport can be determined by quantifying non-specific uptake in the presence of HC-3 as determined by radioactivity and subtracting the non-specific uptake from the total uptake to yield specific transport.

Radiolabeling assays are preferred for determining uptake. [3] can be used as a radiolabel.

f. Other Cholinergic Markers

Other methods for determining modulation of cholinergic function that can be used in the current invention include acetylcholinesterase (AChE) staining, AChEs and choline acetyltransferase activities, binding to α-bungarotoxin-sensitive nAChRs (a class of nAChRs which is spared in p2−/− mice (Zoli et al., 1998) or binding to muscarinic M1 and M2-type receptors. (Zoli et al., 1999).

XII. Diagnostics for hCHT and mCHT

Agents that modulate the choline transporter function represent a novel opportunity to influence cholinergic signaling therapeutically for neuromuscular, autonomic or central nervous system (CNS) disorders. The present invention provides methods for identifying new compounds that modulate CHT, or more preferably hCHT or mCHT activity, which may be termed as "candidate substances." The candidate substance can be a small molecule, peptide, polypeptide, protein or polymer and can increase or decrease the rate of CTU.

"Modulating compounds" or "compounds that modulate high-affinity choline uptake" is meant to refer to substances that enhance, inhibit, or alter the activity of CHT. Such altered activity includes, but is not limited to, changes in binding preferences for target substrates, and changes in proteinaceous molecule-proteinaceous molecule interactions of CHT that may occur. It is contemplated that such screening techniques will prove useful in the general identification of any compound that will serve the purpose of modulating CHT, or more particularly hCHT or mCHT activity.

It is further contemplated that useful compounds in this regard will in no way be limited to proteinaceous or peptidyl compounds. In fact, it may prove to be the case that the most useful pharmacological compounds for identification through application of the screening assays will be non-peptidyl in nature and, e.g., which will serve to modulate hCHT or mCHT activity through a tight binding or other chemical interaction. Candidate substances may be obtained from, for example, libraries of synthetic chemicals, or from natural samples, such as rain forest and marine samples.

a. CHTprotease Assay

To identify a hCHT or mCHT modulator using a CHT protease assay, one would simply conduct parallel or otherwise comparatively controlled protease assays and identify a compound that modulates CHT protease activity. The candidate screening assay is quite simple to set up and perform. After obtaining a relatively purified preparation of CHT protein, polypeptide or peptide, either from native or recombinant sources, one will simply admix a candidate substance with the CHT preparation, under conditions that would allow hCHT or mCHT to perform its function but for inclusion of a modulating substance.

For example, one will typically desire to include within the admixture an amount of a CHT protease, although other substrates may be used, such as other proteases. In any event, one would measure the ability of the candidate substance to alter protease inhibition by the HCHT or mCHT protein, polypeptide, or peptide in the presence of the candidate substance. In general, one will desire to measure or otherwise determine the activity of the relatively purified CHT in the absence of the added candidate substance relative to the activity in the presence of the candidate substance in order to assess the relative modulating capability of the candidate substance.

b. Immunoassays

The antibodies and other candidate substances of the invention can be used as therapeutic agents for neuromuscular, autonomic or CNS disorders. Immunodetection methods may be used in the current invention for detecting biological components as well as binding, purifying, removing and quantifying the biological component. The encoded proteins or peptides of the present invention may be employed to detect antibodies having reactivity therewith, or, alternatively, antibodies prepared in accordance with the present invention, may be employed to detect the encoded proteins or peptides, such as CHT.

The steps of various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs), radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods of this invention include methods for detecting or quantifying the amount of a reactive component in a sample, which methods require the detection or quantitation of any immune complexes formed during the binding process. Here, one would obtain a CHT protein, peptide or a corresponding antibody, and contact it with an antibody or encoded protein or peptide, as the case may be, and then detect or quantify the amount of immune complexes formed under the specific conditions.

In terms of antigen detection, the biological sample analyzed may be any sample that is suspected of containing an antigen specific for a disorder such as a neuromuscular, autonomic or CNS disorder. The sample can be a tissue section or specimen, a homogenized tissue extract, an isolated cell, a cell membrane preparation, separated or purified forms of any of the above protein-containing compositions, or even any biological fluid that comes into contact with tissue such as blood.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present, such as CHT. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

c. Western Blot

It is contemplated that CHT proteins or peptides of the current invention can find utility in Western Blot analysis. Western Blot analysis can be used to determine the effectiveness of candidate substances in the modulation of high-affinity choline uptake. Preferred detection methods include chemiluminescence and chromagenic detection. Standard methods for Western Blot analysis can be found in, for example, Bollag et al., 1996 or Harlow et al. 1988, herein incorporated by reference.

d. ELISAs

As noted, it is contemplated that the CHT proteins or peptides of the invention, such as hCHT and mCHT, will find utility in ELISAs.

In one exemplary ELISA, antibodies binding to the encoded proteins of the invention are immobilized onto a selected surface exhibiting protein affinity, such as a well in a polystyrene microtiter plate. Then, a test composition suspected of containing a marker antigen, such as a hCHT, is added to the wells. After binding and washing to remove non-specifically bound immunocomplexes, the bound antigen may be detected.

Detection is generally achieved by the addition of a second antibody specific for the target protein, that is linked to a detectable label. This type of ELISA is a simple "sandwich ELISA". Detection also may be achieved by the addition of a second antibody, followed by the addition of a third antibody that has binding affinity for the second antibody, with the third antibody being linked to a detectable label.

In another exemplary ELISA, the CHT or other samples suspected of containing a disease or disorder marker antigen is immobilized onto the well surface and then contacted with the antibodies of the invention. After binding and washing to remove non-specifically bound immunecomplexes, the bound antibody is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides, such as CHT, are immobilized, involves the use of antibody competition in the detection. In this ELISA, labeled antibodies are added to the wells, allowed to bind to the CHT or related marker protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of a protein or antibody to the well, coating with a non-reactive material to reduce background, and washing to remove unbound material, the immobilizing surface is contacted with the control clinical or biological sample to be tested under conditions effective to allow immunocomplex (antigen/antibody) formation. Detection of the immunocomplex then requires a labeled secondary binding ligand or antibody, or a secondary binding ligand or antibody in conjunction with a labeled tertiary antibody or third binding ligand.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 h at room temperature in a PBS-containing solution such as PBS-Tween).

In other embodiments, solution-phase competition ELISA is also contemplated. Solution phase ELISA involves attachment of CHT or a related peptide to a bead, for example a magnetic bead. The bead is then incubated with sera from human and animal origin. After a suitable incubation period to allow for specific interactions to occur, the beads are washed. The specific type of antibody is the detected with an antibody indicator conjugate. The beads are washed and sorted. This complex is the read on an appropriate instrument (fluorescent, electroluminescent, spectrophotometer, depending on the conjugating moiety). The level of antibody binding can thus by quantitated and is directly related to the amount of signal present.

e. Immunohistochemistry

The antibodies of the present invention, such as anti-CHT antibodies, also may be used in conjunction with both fresh-frozen and formalin-fixed, paraffin-embedded tissue blocks prepared from study by immunohistochemistry (IHC). For example, each tissue block consists of 50 mg of residual "pulverized" tumor. The method of preparing tissue blocks from these particulate specimens has been successfully used in previous IHC studies of various prognostic factors, e.g., in breast, and is well known to those of skill in the art (Brown et al., 1990; Abbondanzo et al., 1990; Allred et al., 1990).

Briefly, frozen-sections may be prepared by rehydrating 50 ng of frozen "pulverized" tumor at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

f. FACS Analyses

Fluorescent activated cell sorting, flow cytometry or flow microfluorometry provides the means of scanning individual cells for the presence of an antigen, such as CHT. The method employs instrumentation that is capable of activating, and detecting the excitation emissions of labeled cells in a liquid medium. FACS is unique in its ability to provide a rapid, reliable, quantitative, and multiparameter analysis on either living or fixed cells. The antibodies of the present invention provide a useful tool for the analysis and quantitation of markers of individual cells.

g. Green Fluourescent Protein Staining

Green fluorescent protein can be used to stain the cholinergic neurons and thereby allow for visual analysis of a targeted animal, culture, brain slice, etc. The use of green flurescent protein has been described in U.S. patent application Ser. No. 09/888,233 "Assay for Toxin Induced Neuronal Degeneration and Viability in *C. elegans*," filed Jun. 22, 2001 and herein incorporated by reference. This application provides in vivo screening methods to detect and identify substances that affect neuronal viability, and/or prevent neurodegeneration, and/or confer neuroprotective effects using recombinant *C. elegans* expressing a detectable marker in neuronal sub-groups and neurotoxins specific to specific neuronal cells.

XIII. Pharmaceutical Preparations

Pharmaceutical compositions of the present invention comprise an effective amount of one or more hCHT or mCHT or more particularly one or more hCHT or mCHT inhibitors or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one CHT or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (et al., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (et al., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences*, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The hCHT or mCHT may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (et al. aerosol inhalation), injection, infusion, continuous infusion, localized perfusion bathing target cells directly, via a catheter, via a lavage, in cremes, in lipid compositions (et al., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (et al., methylparabens, propylparabens), chlorobutanol, phenol, sorbic acid, thimerosal or combinations thereof.

The hCHT or mCHT may be formulated into a composition in a free base, neutral or salt form. Pharmaceutically acceptable salts, include the acid addition salts, et al, those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (et al., glycerol, propylene glycol, liquid polyethylene glycol, etc), lipids (et al., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the hCHT or mCHT is prepared for administration by such routes as oral ingestion. In these embodiments, the solid composition may comprise, for example, solutions, suspensions, emulsions, tablets, pills, capsules (et al., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof, a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

The composition may be combined with secondary agent which may be an agent used to treat a disease such as Parkinson's disease, Huntington's disease, Alzheimer's, schizophrenia or dysautonomia. The secondary agent may be a muscarinic agent, an antimusciarinic agent (i.e. atropine, scopolamine, pirenzepine, blycopyrrolate methscopolamine, benztropine, homatropine cyclopentolate or eucatropine), a ganglionic agent, a neuromuscular blocking agent (i.e. tubocurarine, gallamine, pancuronium, atracurium, succinylcholine or decamethonium), a nicontinic agent or a cholinesterase inhibitor (i.e. physostigmine, neostigmine, pyridostigmine, edrophonium or ambenonium).

XIV. Kits

Any of the compositions described herein may be comprised in a kit. In a non-limiting example, a choline transporter, and additional agent, may be comprised in a kit. The kits will thus comprise, in suitable container means, a choline transporter and a lipid, and/or an additional agent of the present invention.

The kits may comprise a suitably aliquoted choline transporter, lipid and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the choline transporter, lipid, additional agent, and any other reagent containers in close confinement for commercial sale. Such containers may include injection or blow-molded plastic containers into which the desired vials are retained.

Therapeutic kits of the present invention are kits comprising a choline transporter such as SEQ ID NO. 1-4 protein, polypeptide, peptide, inhibitor, gene, vector and/or other effector. Such kits will generally contain, in suitable container means, a pharmaceutically acceptable formulation of SEQ ID NO. 1-4 protein or polypeptides, and/or a gene and/or vector expressing any of the foregoing in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The candidate substance, antibody or CHT such as SEQ ID NO. 2 or SEQ ID NO. 4 compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

The container means will generally include at least one vial, test tube, flask, bottle, syringe and/or other container means, into which the candidate substance, antibody or CHT such as SEQ ID NO. 2 or SEQ ID NO. 4 formulation are placed, preferably, suitably allocated. The kits may also comprise a second container means for containing a sterile, pharmaceutically acceptable buffer and/or other diluent.

In further embodiments, the invention provides immunological kits for use in detecting substances which modulate high-affinity choline uptake, e.g., in biological samples. Such kits will generally comprise one or more substances that have immunospecificity for proteins or peptides, such as a hCHT peptide, encoded by the nucleic acid markers of disorders such as neuromuscular, autonomic or CNS disorders identified in the present invention.

Kits comprising antibodies, will be preferred in many cases. In more preferred embodiments, it is contemplated that the antibodies will be those that bind to the CHT epitopes. Monoclonal antibodies are readily prepared and will often be preferred. Where marker proteins or peptides are provided, it is generally preferred that they be highly purified.

In certain embodiments, the CHT protein or peptide, or the first antibody that binds to the CHT protein or peptide may be bound to a solid support, such as a genechip, microbead, column matrix or well of a microtitre plate.

The immunodetection reagents of the kit may take any one of a variety of forms, including those detectable labels that are associated with, or linked to, the given antibody or antigen itself Detectable labels that are associated with or attached to a secondary binding ligand are also contemplated. Exemplary secondary ligands are those secondary antibodies that have binding affinity for the first antibody or antigen.

Further suitable immunodetection reagents for use in the present kits include the two-component reagent that comprises a secondary antibody that has binding affinity for the first antibody or antigen along with a third antibody that has binding affinity for the second antibody, wherein the third antibody is linked to a detectable label.

As noted above in the discussion of antibody conjugates, a number of exemplary labels are known in the art and all such labels may be employed in connection with the present invention. Radiolabels such as [$^3$H] hemicholinium-e, nuclear magnetic spin-resonance isotopes, fluorescent labels and enzyme tags capable of generating a colored product upon contact with an appropriate substrate are suitable examples.

The kits may contain antibody-label conjugates either in fully conjugated form, in the form of intermediates, or as separate moieties to be conjugated by the user of the kit.

The kits may further comprise a suitably aliquoted composition of the CHT protein or antigen, such as hCHT, whether labeled or unlabeled, as may be used to prepare a standard curve for a detection assay.

The kits of the invention, regardless of type, will generally comprise one or more containers into which the biological agents are placed and, preferably, suitable aliquoted. The components of the kits may be packaged either in aqueous media or in lyophilized form.

The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed.

The kits of the present invention will also typically include a means for containing the antibody, antigen, and any other reagent containers in close confinement for commercial sale. Such containers may include injection or blow-molded plastic containers into which the desired vials are retained.

The following abbriviations are used throughout this specification: high-affinity choline uptake (HACU); acetylcholine (Ach); high affinity choline transporter (CHT); human CHT (hCHT, SEQ ID NO: 2); mouse CHT (mCHT, SEQ ID NO: 4); rat CHT (rCHT1, SEQ ID NO: 6); cDNA encoding the high-affinity choline transporter from *Caenorhabditis elegans* (CHOI); and hemicholinium-3 (HC-3).

As used herein in the specification, "a" or "an" may mean one or more. As used herein in the claim(s), when used in conjunction with the word "comprising," the words "a" or "an" may mean one or more than one. As used herein "another" may mean at least a second or more.

XV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cloning of hCHT cDNA

Based on the DNA sequence information obtained from the Human Genome Sequence Database and rCHT1 (SEQ ID NO: 5), genomic sequences (GenBank Accession Number AC009933, SEQ ID NO:13) predictive of a human homologue for rCHT were identified. Based on inferred coding exons, inventors designed non-degenerate oligonucleotide primers to isolate an hCHT cDNA (SEQ ID NO:1). The sense primer of SEQ ID NO: 15 (RB855, ATAAAAATGGCTTTCCATG-TGGAAGGACTG) overlaps the putative start codon and extends by 16 nucleotides on the 5' end and 11 nucleotides on the 3' end. The antisense primer of SEQ ID NO: 16 (RB852, TCACTGTAAAT-TATCTTCCAGTCCCAGACCC) overlaps the putative stop codon. hCHT cDNA was amplified by PCR (5 min at 95° C. followed by 35 cycles of 30 sec at 95° C., 30 sec at 60° C., and 4 min at 68° C. and finally a 7 min extension at 68° C.) using human spinal cord cDNA (Clontech) as template with Pfu Turbo DNA polymerase and the ProStar Ultra HF kit (Stratagene). The PCR amplified products were inserted the NotI and XhoI sites of pcDNA3 (Invitrogen and sequence of the inserted cDNA was determined using fluorescent dye terminators and an ABI310 automated DNA sequencer (Center for Molecular Neuroscience and Neurogenomics Core, Vanderbilt University). The nucleotide sequence of hCHT cDNA and inferred translation is given as SEQ ID NO: 1 (GenBank accession number AF276871). Sequence alignments of hCHT, rCHT, and CHO-1 as well as other gene family members were performed with the MegAlign module of Lasergene software (DNASTAR).

Figure 4:
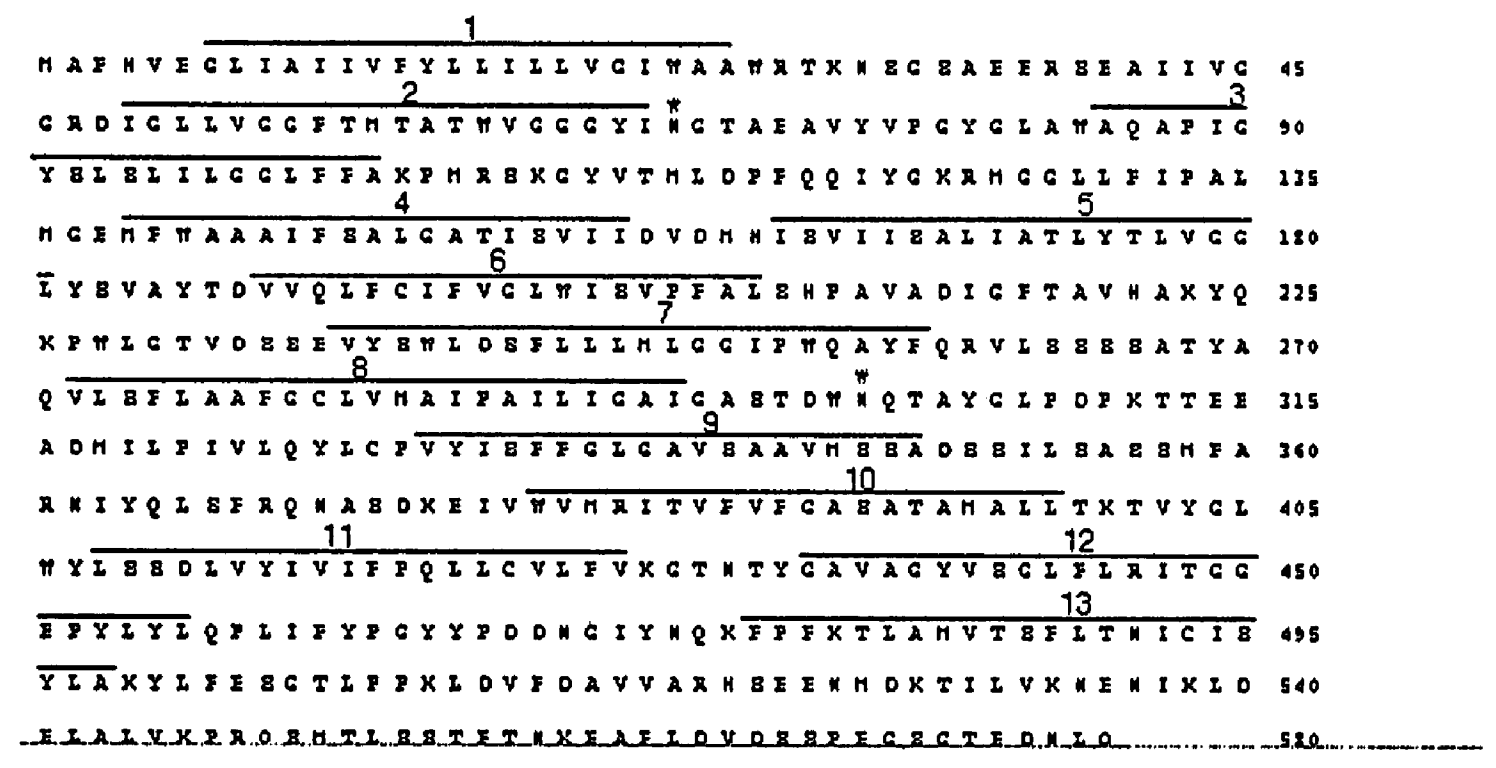

The amino acid sequence of rCHT1 (SEQ ID NO: 6) was used to search the Human Genome Sequence Database for a potential human ortholog. A GenBank BLAST search yielded bacterial artificial chromosome (BAC) sequences SEQ ID NO:13, and SEQ ID NO:14 (AC009963 and AC023672) containing unannotated sequences that display 87% nucleotide identity to rCHT coding sequence with conserved translational initiation and termination sites. Using human spinal cord cDNA as template, we amplified by PCR a 1780 bp product whose sequence matches the inferred exons of the putative hCHT gene found in the BAC sequences. The presence of an inframe stop codon in the BAC sequence (SEQ ID NO: 13) 9 nucleotides 5' of our predicted start codon supports the conclusion that hCHT protein initiates at the designated ATG. The hCHT cDNA encodes a protein of 580 amino acids (FIG. 4), a predicted mass ($M_r$) of 63,203 Da and a calculated isoletric point of 4.9. The hCHT nucleotide and amino acid sequence are given as SEQ ID NO: 1 and SEQ ID NO: 2 respectively.

Sequence analysis of the predicted hCHT protein using Kyte-Doolittle (Kyte et al., 1982), TopPred2 (von Heijne, 1992) and Signal P (Nielsen, et al., 1997) algorithms, predict the presence of 13 transmembrane spanning domains (FIGS. 3-4) and the presence of a signal peptide that would orient the initial 6 amino acids extracellularly. There are 3 canonical N-linked glycosylation residues; N69 and N301 are predicted to be localized extracellularly. It is noteworthy that SGLT1 and NIS were also originally predicted to have 12 TMDs with $NH_2$ and COOH terminus oriented towards the cytoplasm (Dai et al., 1996; Turk et al., 1997). However, more recent N-linked glycosylation site mutagenesis and immunofluoroscence studies reveal the presence of an extracellular $NH_2$ terminus (Turk et al., 1997; Levy et al., 1998). Recently, SGLT1 has been predicted to contain 14 TMDs with the last TMD established by a hydrophobic domain at the very COOH terminus (Turk et al., 1997). Unlike SGLT1, but more like NIS, hCHT lacks such a domain, resulting in cytoplasmic COOH terminus (Turk et al., 1997; Levy et al., 1998). Canonical sites for phosphorylation by protein kinase C are present on the putative cytoplasmic domain between TMD9 and TMD10(S367 and S373) as well as in the COOH terminus (T558). Canonical sites for protein kinase A are also present between TMD7 and TMD8 (S263) and on the COOH terminus (S522 and S550). Moreover, there are an additional 12 serine and 10 threonine residues in predicted cytoplasmic domains of hCHT that may represent noncanonical sites for regulatory phosphorylation.

Sequence alignments reveal hCHT protein to exhibit 93% amino acid identity to rCHT1 and 51% amino acid identity to the C. elegans gene product CHO-1. Outside of putative species orthologs, hCHT is distantly related to the SLC5A family of solute carriers that includes the $Na^+$-coupled glucose transporter 1 (SGLT1; 25% AA identity) (Turk et al., 1997; Hediger et al., 1987) and the $Na^+/I^-$-iodide symporter (NIS; 21% AA identity) (Dai et al., 1996).

Example 2

Cloning of mCHT cDNA

Degenerate oligonucleotides were used to amplify a 1780 bp product by RT-PCR from mouse spinal cord RNA. The PCR product comprises is what is expect for a full-length open reading frame for mCHT and exhibits a 98% nucleotide identity to rCHT1. BLAST analysis of the Celera Discovery System™ v3.01 mouse genomic DNA assembly using our mCHT cDNA yielded an identical sequence for the coding exons of mCHT and conserved intron/exon boundaries with the human CHT gene. The mCHT cDNA (GenBank accession number AF276872) encodes a protein of 580 amino acids and has a predicted mass of 63 kDa with a calculated isoelectric point of 4.9 (FIG. 2). Consistent with our predicted model for the secondary structure of hCHT (Apparsundaram et al., 2000) and the recently reported model for Limulus ChCoT (Wang et al., 2001), hydropathy analysis of mCHT amino acid sequence indicates the presence of 13 transmembrane domains (TMDs) with a short extracellular $NH_2$ and large intracellular COOH terminus. There are 3 canonical sites for N-linked glycosylation with N69 and N301 oriented extracellularly. Canonical sites for phosphorylation by protein kinase C are present on the putative cytoplasmic domain between TMD9 and TMDlO (S367 and S373) as well as in the COOH terminus (T558). Canonical sites for protein kinase A are also present on the cytoplasmic (S263) and COOH terminus (S522 and S550). Sequence alignments reveal that the mCHT protein exhibits a 93% and 98% AA identity with hCHT and rCHT1, respectively and 50% and 46% AA identity with Caenorhabditis elegans CHO-1 and Limulus polyphemus ChCoT, respectively (FIG. 2). Overall there is 39% AA identity among all the known choline transporters and a 93% AA identity among mCHT, hCHT and rCHT1. Conserved residues are likely to play a role in choline recognition or in conserved aspects of substrate translocation. Together, these proteins constitute a new a family of proteins distantly related to the SLC5A family of solute carriers which includes the $Na^+$-coupled glucose transporters SGLT1 (25% amino acid identity) and $Na^+$/1-Symporter (NIS; 21% amino acid identity) (Turk et al., 1997; Dai et al., 1996).

Figure 5:
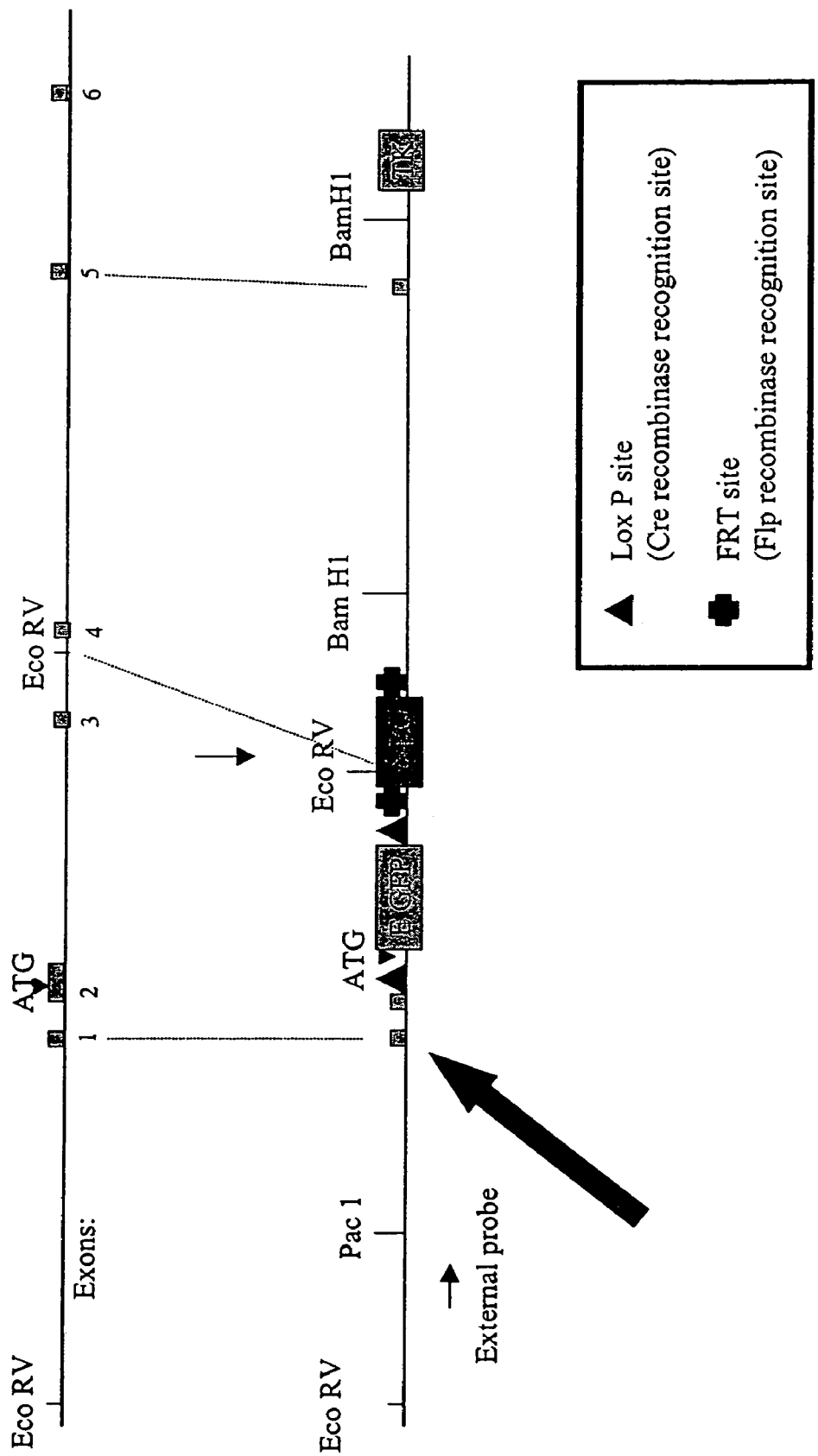
FIG. 5-S*trategy* for the "knockout" of the mouse choline transporter gene. The gene is shown before and after creation of the knockout line. Enhanced GFP (EGFP) is being introduced into the line to allow for regulated GFP production from the endogenous choline transporter promoter. When cut with Eco RV and probed with the 5' external probe the DNA from a targeted ES cell clone should give: 7 kb wild type allele band size and 5.3 kb targeted allele band size.

The "knockout" of the mouse choline transporter gene is shown in FIG. 5. This figure depicts the gene before and after creation of the knockout line. Enhanced GFP (EGFP) was introduced into the line to allow for regulated GFP production from the endogenous choline transporter promoter. When cut with Eco RV and probed with the 5' external probe the DNA from a targeted ES cell clone should give a 7 kb wild type allele band size and 5.3 kb targeted allele band size.

Example 3

Chromosomal Localization

The chromosomal localization of the hCHT gene was determined by radiation hybrid mapping (Stewart, et al., 1997). Briefly, oligonucleotide primers were selected to amplify a 616 bp fragment of genomic DNA corresponding to a region that overlaps with the hCHT1 stop codon. The sense primer RB885 (5'-CTGTGTATGGGCTCTGGTA CC-3'; SEQ ID NO:16) is complementary to bases 1202-1220 of the hCHT coding sequence. The antisense primer of SEQ ID NO:17 (RB934, 5'-GCTGCATACCATCTCTCC-3'; SEQ ID NO:15) was designed based on analysis of the genomic sequence immediately 3' from the hCHT stop codon (SEQ ID NO:19, GenBank Accession Number AC009963). PCR mapping with SEQ ID NOS: 17-18 was performed using the Stanford G3 Human/Hamster Radiation Hybrid panel (Research Genetics) as template. The PCR conditions were: 5 min at 95° C. followed by 35 cycles of 30 sec at 95° C., 30 sec at 60° C., and 30 sec at 72° C. and finally a 7 min extension at 72° C. PCR products were denatured for 30 min at 37° C. in a solution of 0.4 N NaOH/25 mM EDTA and blotted onto Hybond N nylon membrane (Amersham). The blot was UV cross-linked (Stratalinker, Stratagene) and then baked at 80° C. under vacuum for 30 min and then hybridized with a 463 bp hCHT Kpn1/Stu1 restriction fragment (bp 1221-1684), labeled by random priming (Prime-It II, Stratagene) in the presence of $[^{32}P]$-αdCTP (Amersham). Hybridization was performed for 1 hour at 68° C. in ExpressHyb (Clontech) with a probe concentration of $10^6$ cpm/ml. The membrane was washed to a final stringency of 0.1×SSC 0.1% SDS for 1 hour at 68° C. prior to X-ray film development. Hybridization results were submitted for scoring on the Stanford Human Genome Center (SHGC) G3 radiation hybrid panel (shgc.stanford. edu/RH/index.html).

Altered cholinergic function is a feature of multiple cognitive, neuromuscular, motor and autonomic disorders (Coyle et al., 1983; Calabresi et al., 2000; Tandon 1999; Lange et al., 1992; Baron et al., 1996; Rodriguez-Puertas et al., 1994; Alvarez et al., 1996). Assessment of the involvement of hCHT as a risk factor in such syndromes first requires the high resolution mapping of the hCHT gene. Using human and hamster genomic DNA, the inventors defined PCR conditions such that oligonucleotide primers specifically amplify a 616 bp product from human but not from hamster templates. This allowed for the assessment of the distribution of human specific amplicons on the SHGC radiation human/hamster hybrid panel, with amplifications confirmed as hCHT-derived by hybridization with a hCHT cDNA probe. Results revealed that the hCHT1 locus is tightly linked to markers of SEQ ID NOS: 20-21 on chromosome 2 (D2S340, GenBank Accession Number Z23978 and D2S176, GenBank Accession Number Z17178). The proximity of hCHT to these two markers corresponds to a cytogenetic location of 2q12. In addition, a search of BAC clone of SEQ ID NO: 19 (RP11-368F12, AC009963) which contains the hCHT gene, reveals that this BAC also encodes a portion of the Ran binding protein 2 (RanBP2) gene. RanBP2 has been localized with high resolution to 2q12 between SEQ ID NO: 20 and SEQ ID NO: 22 (D2S1893, GenBank Accession Number Z53730) by a combination of fluorescence in situ hybridization (FISH) analysis, sequence analysis, and physical mapping (Nothwang et al., 1998).

Figure 6:
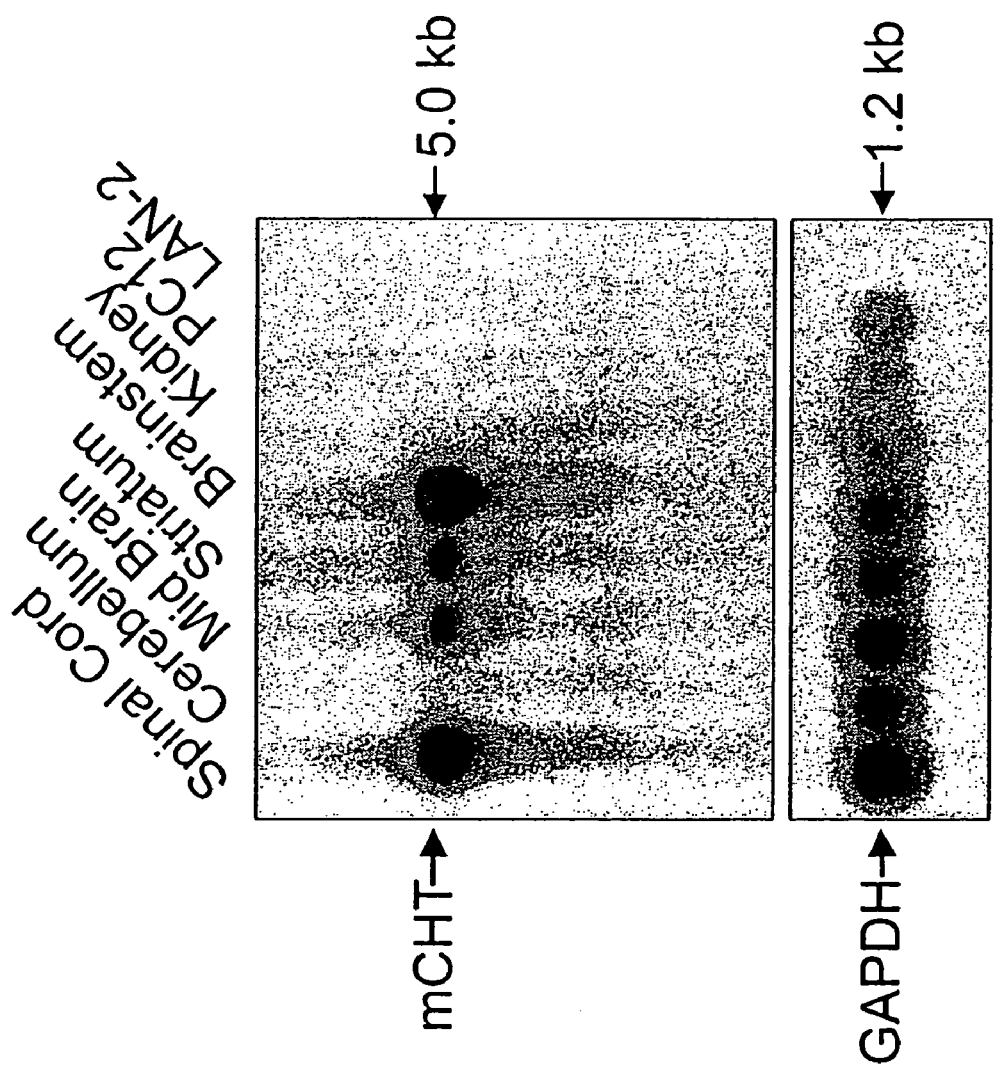
FIG. 6-N*orthern* blot analysis of mCHT. Mouse tissue mRNA, mRNA electrophoresis and Northern transfer and hybridization were carried out as described in "Materials and Methods". Each lane was loaded with poly A+ enriched RNA isolated from 100 µg of total RNA. A single 5 kb species is observed in cholinergic rich brain regions such as spinal cord, brainstem and striatum but not in cerebellum, kidney as well as rat pheochromocytoma PC12 and human neuroblastoma LA-N-2 cells.

To ascertain the expression pattern and possible mRNA heterogeneity of mCHT, a Northern analysis was done using as a probe a 547-bp cDNA fragment corresponding to the most 3' region of the mCHT coding sequence. Consistent with the distribution of cholinergic cell bodies in mouse CNS (Erickson et al., 1994; Naciff et al., 1997), the Northern blot analysis revealed a restricted regional distribution of mCHT mRNA as a single transcript of ~5 kb in spinal cord, brainstem, midbrain and striatum (FIG. 6). No hybridization was evident in cerebellum, kidney, rat pheochromocytoma PC12, and human neuroblastoma LA-N2, despite evidence of control hybridization with GAPDH probe. Studies with CHT fusion protein and peptide-directed antibodies (Apparsundaram et al., 2001) also support a localization of CHT protein in cholinergic soma and terminals.

Example 4

RT-PCR for CHT cDNA

Based on the sequence information of rCHT1 and the information provided by human genomic sequence database (SEQ ID NO: 19), degenerate oligonucleotides were designed to be suitable for the amplification of the full open reading frame of mCHT from mouse spinal cord RNA. The sense primer (SEQ ID NO: 26, RB892 5'-CTGGATC-CAAAATGG/CCTTTCCATGTA/GGAAGG-3') overlaps the putative start codon (underlined) and extends by 21 nucleotides on the 5' end and 7 nucleotides on the 3' end. The antisense primer (SEQ ID NO: 27, RB893; 5'-GACTCGAG-GTCAC/-TTGTAAA/GTTATCTTCAGTCCC-3') begins 15 bases 3' of the putative stop codon (underlined). Mouse spinal cord total RNA was isolated using TRIZOL reagent (Life Technologies) and the RT-PCR amplification was carried out using the Prostar Ultra HF RT-PCR system (Stratagene) using oligo dT primers following manufacturer's protocols. PCR amplified products from mouse spinal cord were inserted into pcDNA3 (Invitrogen) between the Not1 and Xho1 sites and the nucleotide sequences of the inserted cDNA was determined using fluorescent dye terminators and an ABI310 automated DNA sequencer (Center for Molecular Neuroscience Neurogenomics Core, Vanderbilt University). The nucleotide sequence of mCHT cDNA and inferred translation can be obtained in SEQ ID NO: 23. Comparisons against mouse genomic DNA to validate cDNA sequence and to establish intron/exon boundaries were made using the Celera Discovery System™ v3.01 database assembly of the mouse genome. Sequence alignments of the mCHT orthologs were performed with version 1.6.3 of Lasergene (DNAStar, Inc.)

Example 5

Northern Analysis

The regional distribution of hCHT mRNA was examined using the human brain multiple tissue Northern Brain Blot II panel (Clontech). A 463 bp cDNA probe corresponding to hCHT bases 1221-1684(Kpn1/Stu1 restriction fragment) was labeled with by random priming (Prime-It II, Stratagene) in the presence of [$\alpha$-$^{32}$P] CTP (Amersham). Hybridization was carried out for 1 hour at 68° C. in Expresshyb (Clontech) with a probe concentration of $1.5\times10^6$ cpm/ml. The membrane was washed at high stringency (30 min at 25° C. in 2×SSC 0.05% SDS followed by 1 hour at 68° C. in 0.1×SSC 0.1% SDS) and exposed to X-ray film (Kodak X-AR) for 112 hours before development. To validate evenness of loading, the blot was reprobed using a human $\alpha$-actin cDNA (Clontech) probe at $10^6$ cpr/ml.

Figure 7:
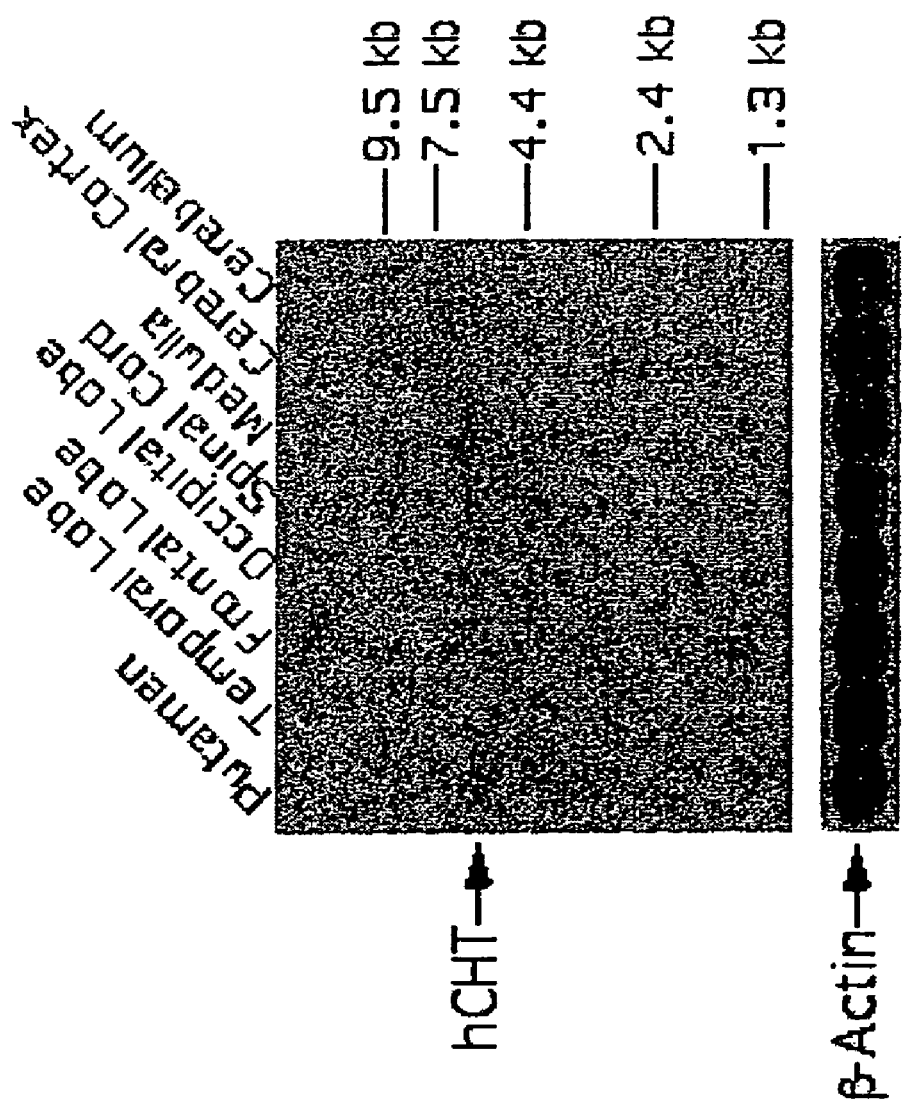
FIG. 7-Kyte-Doolittle hydrophilicity plot (window=15 amino acids) of hCHT amino acid sequence revealing the presence of 13 hydrophobic regions and a hydrophilic COOH terminal domain. Northern blot analysis of hCHT reveals a 5 kb transcript which is specifically expressed in the putamen, spinal cord, and medulla, cholinergic neuron rich brain regions; probing for α-actin reveals that the lanes are evenly loaded.

To examine the distribution of hCHT mRNA in human brain, a Northern Blot analysis was done using a 463 bp fragment comprising the 3' end of our hCHT1 cDNA. Results show hCHT mRNA to exhibit a restricted regional distribution in the CNS, consistent with the distribution of cholinergic cell bodies. Thus, a single transcript of ~5 kb was detected in the putamen, spinal cord, and medulla (FIG. 7). This pattern of expression is consistent with the distribution of cholinergic neurons including the large, aspiny interneurons of the basal ganglia and the motoneurons of the midbrain, brainstem and spinal cord (Kato et al., 1985; Mizukawa et al., 1986; Mesulam et al., 1992). No hybridization was evident in temporal lobe, frontal lobe, occipital lobe, cerebral cortex and cerebellum despite evidence of control hybridization products with $\alpha$-actin. (FIG. 7).

Figure 8:
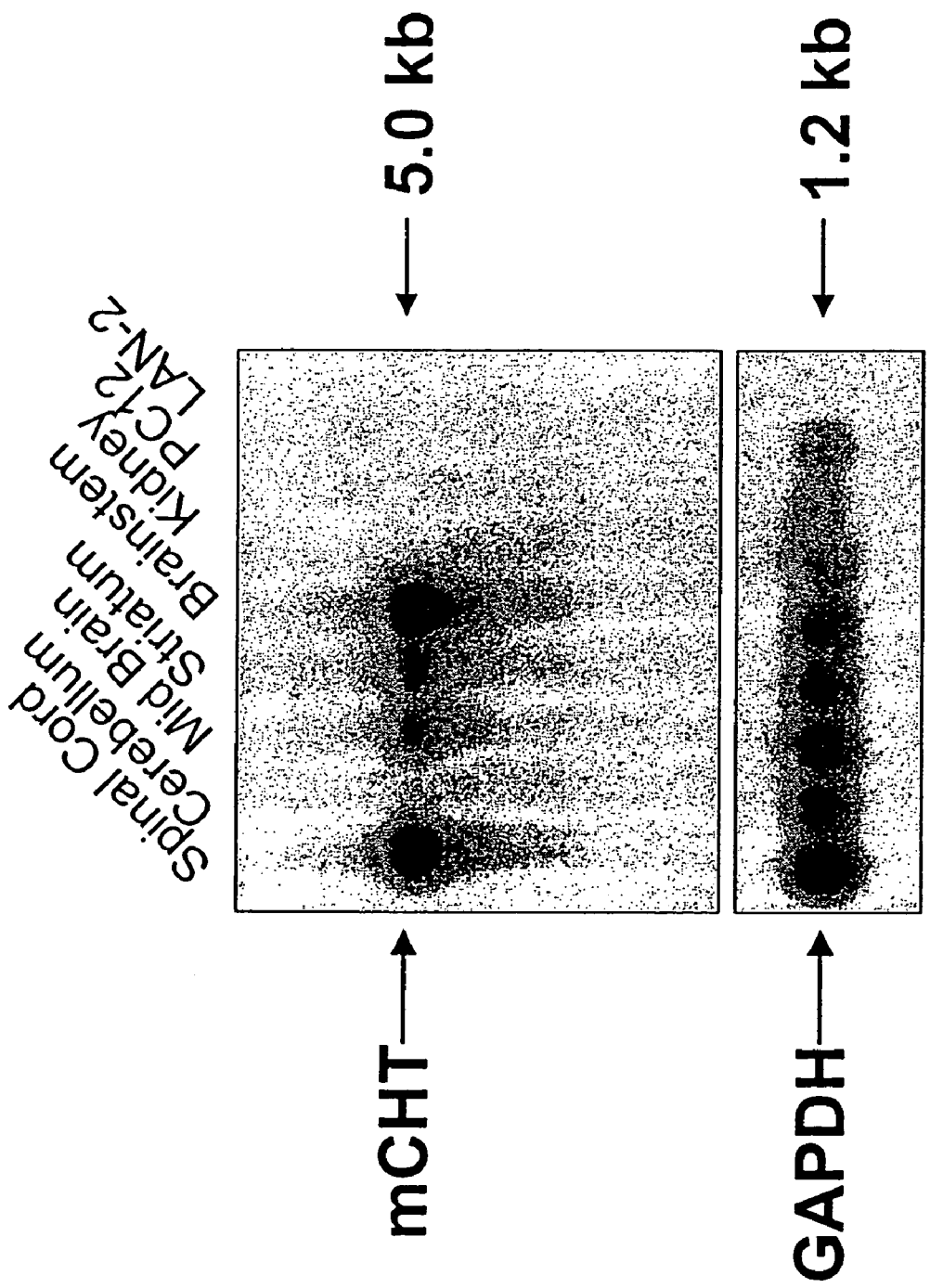
FIG. 8—Northern Blot analysis of mCHT expression. Northern blot of mouse choline transporter mRNA expression in different tissues. GAPDH is used as a positive control for mRNA loading.
Figure 9:
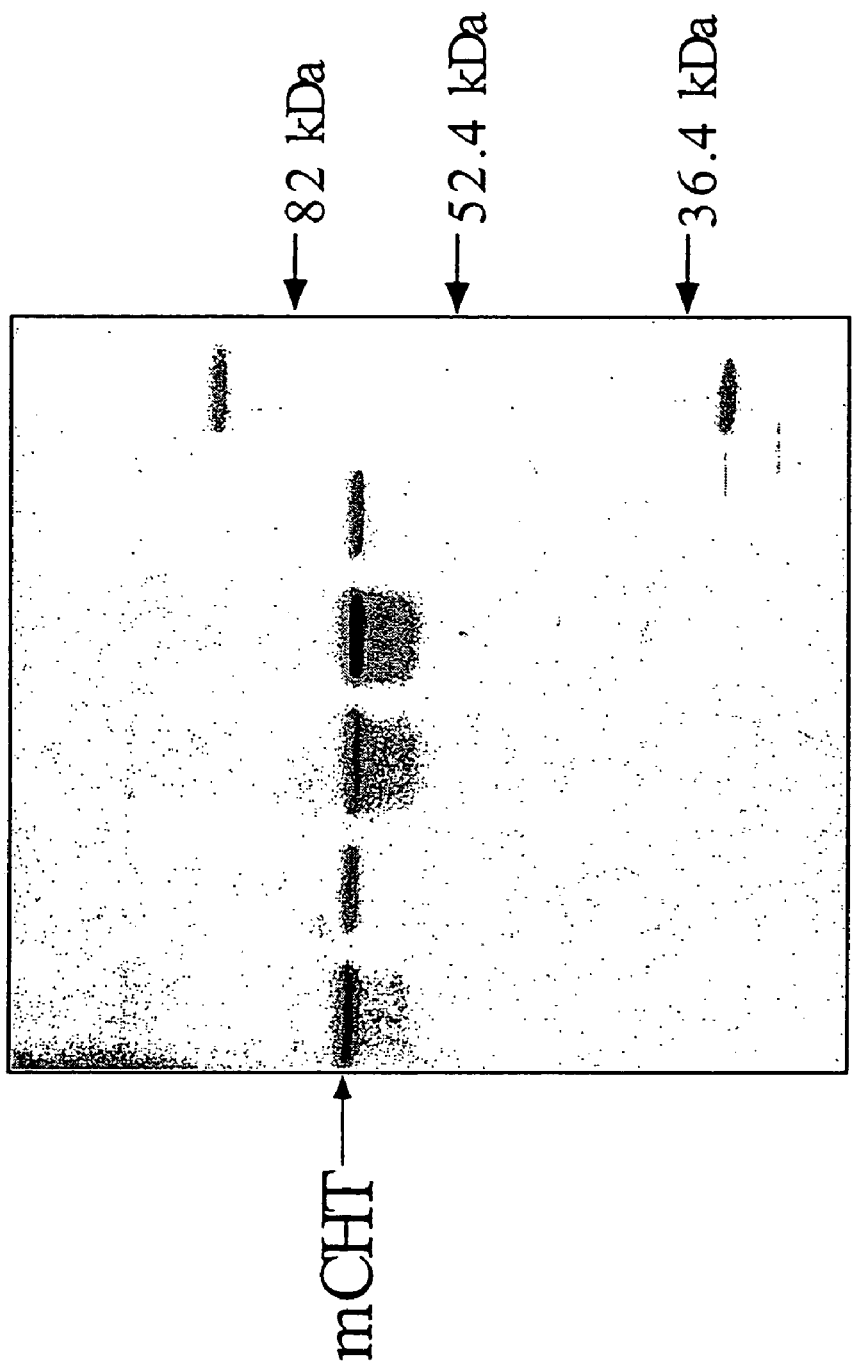
FIG. 9—Western Blotting with affinity purified antibody 97520 reveals a 70 kDa band in cholinergic tissues. The immunizing peptide corresponds to the human, mouse, and rat CHT C-terminus 15 amino acids (SEQ ID NO: 25, VDSSPEGSGTEDNLQ). The kidney was used as a negative control.

Expression of mCHT mRNA was determined using a Northern Blot analysis for different tissues as shown in FIG. 8. GAPDH is used as a positive control for mRNA loading. Western Blotting was also perfomed with mCHT with affinity purified antibody 97520 (FIG. 9). This analysis reveals a single 70 kDa band in cholinergic tissues distributed in accord with the known distribution of cholinergic terminals. The immunizing peptide corresponds to the human, mouse, and rat CHT C-terminus 15 amino acids (SEQ ID NO: 25). No such band was detected in kidney as a negative control.

Example 6

Radioligand Binding Assays

COS-7 cells were transfected with a pcDNA3 vector containing hCHT cDNA using the FuGene 6 transfection reagent (Roche Diagnostics) following the manufacturer's protocols. Briefly, COS-7 cells were cultured in Dulbecco's modified Eagles' medium (DMEM) supplemented with 10% fetal bovine serum (Hyclone), 100 µg/ml of penicillin and streptomycin at a density of 3-4 million cells in 150 mm culture dishes or $5\times10^4$ cells per well in 24 well dishes (Falcon). After 24 hr, cells were transfected and 48 hr later, the cells were harvested and processed for membrane binding and whole cell or vesicle transport assays.

Monolayers of hCHT transfected COS-7 cells were washed with 30 ml of HTE buffer and harvested in 10 ml of homogenization buffer (0.32 M sucrose in HTE buffer). Cells were homogenized at 20,000 rpm for 25 sec using a Polytron tissue homogenizer (Brinkman). The homogenate was centrifuged at 100,000×g for 45 min at 4° C. The resulting pellet was suspended in 2 ml of HTE buffer, assayed for protein content (Bradford method; BioRad) and 50 µg of the membrane suspension (1 µg/µl) was transferred to each tube in triplicate. Unless otherwise indicated, all binding assays were performed in the presence of 150 mM NaCl in HTE buffer. Assays were initiated by the addition of [$^3$H]HC-3 (127 Ci per mmol; NEN Life Science Products, 10 nM final concentration). After a 1 hr incubation at room temperature, membranes were rapidly filtered through glass fiber GF/B filters (Brandel) soaked in 0.3% polyethylenimine (Sigma) in HTE buffer and accumulated radioactivity was quantified using liquid scintillation spectrometry (Packard). To test the ion dependence of hCHT binding activity, Na$^+$ was replaced in the assay buffer with equimolar concentrations of Li$^+$ whereas Cl$^-$ was replaced with equimolar concentrations of isethionate. Non-specific binding was quantified by measuring [$^3$H] HC-3 binding in the presence of 1 µM unlabeled HC-3 and subtracted from the total counts to yield specific binding. Data for binding and transport assays (see below) were analyzed using nonlinear least squares curve fitting and Scatchard transformations (Kaleidagraph, Abelbeck).

Figure 10:
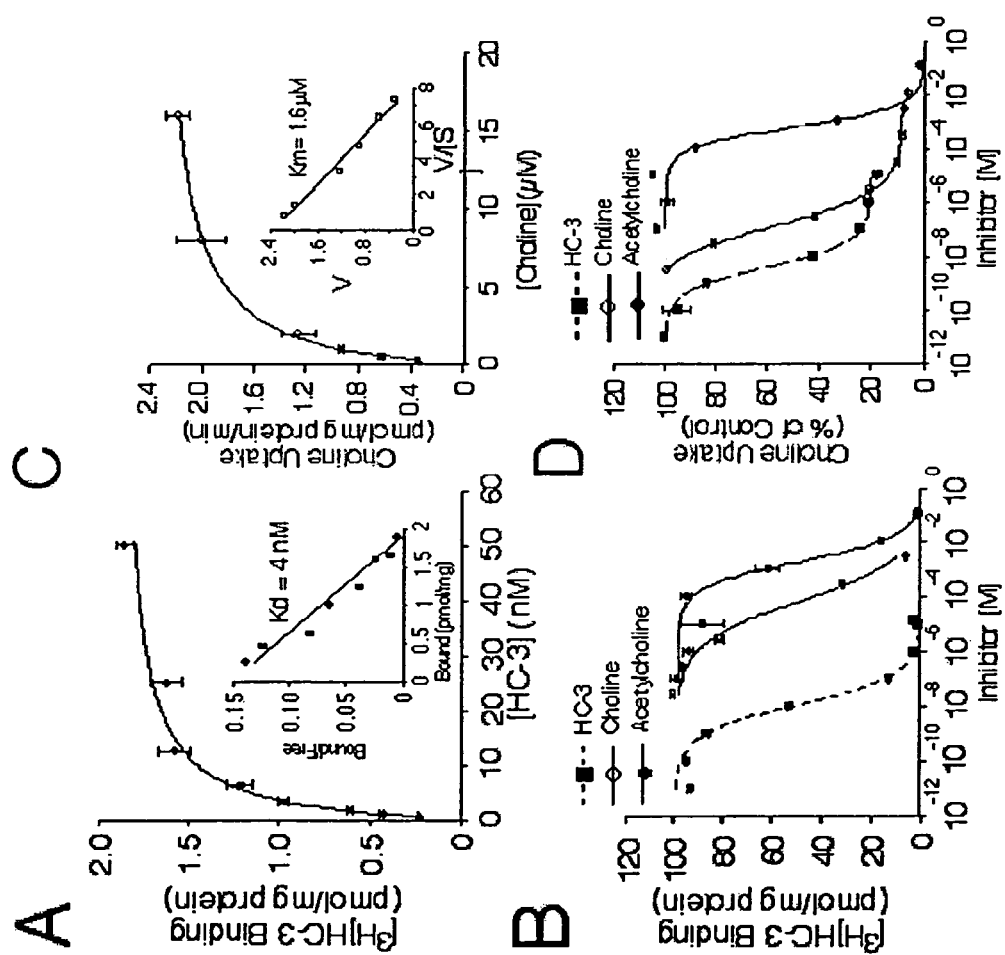
FIGS. 10A-10D—[$^3$H]HC-3 binding sites and [$^3$H]choline uptake are evident following transfection of hCHT1 in COS-7 cells. Binding of [$^3$H] HC-3 in membrane fractions of hCHT transfected COS-7 cells is saturable and has high-affinity. Binding obtained in membrane fractions from pcDNA3 transfected cells were subtracted to define CHT-mediated [3H] HC-3 binding. Insert: Scatchard transformation of CHT-mediated [$^3$H] HC-3 binding (FIG. 10A). Unlabeled HC-3, choline and Ach dose-dependently inhibit [$^3$H] HC-3 binding in membrane fractions of COS-7 cells. Inhibition assays were performed using 10 nM [$^3$H] HC-3. ACh was examined in the presence of 10 µM physostigmine to inhibit cholinesterase activity (FIG. 10B). Uptake of [$^3$H]choline in resealed membrane vesicles derived from transfected COS-7 cells is saturable and has high-affinity for choline. In all assays, [$^3$H] choline uptake determined in the presence of 1 µM HC-3 is defined as non-specific uptake. Insert: Eadie-Hofstee-Scatchard transformation of CHT-mediated [3H] choline uptake (FIG. 10C). Unlabeled HC-3, choline and ACh dose-dependently inhibit [$^3$H] HC-3 binding in membrane fractions of COS-7 cells (FIG. 10D). The results in FIGS. 10A-D are presented as mean +/−SEM of triplicate experiments.

The radiolabeled HACU antagonist [$^3$H]HC-3 has been used to identify CHT protein in human brain membranes (Pascual et al., 1990). Using [$^3$H]HC-3, it was confirmed that the presence of hCHT protein in hCHT1-transfected COS-7 membranes (FIGS. 10A,B). As compared to vector-transfected cells, transfection of hCHT cDNA produced marked increase in [$^3$H]HC-3 binding in membrane fractions of COS-7 cells (data not shown). The binding of [$^3$H]HC-3 is saturable (FIG. 10A) and Scatchard analyses of [$^3$H]HC-3 binding indicate single site kinetics (Hill coefficient n=0.99) with an equilibrium dissociation constant (Kd) of 4 mM. Replacement of either Na$^+$ or Cl$^-$ with lithium or isethionate, respectively, reduced [$^3$H]HC-3 binding to levels seen in vector-transfected cells (data not shown). The low level of non-specific [$^3$H]HC-3 binding detected in vector transfected cells is also insensitive to the removal of either Na$^+$ or Cl$^-$. Unlabeled HC-3, and choline dose-dependently inhibit [$^3$H]HC-3 binding in hCHT transfected COS-7 cell membranes with Hill coefficients not significantly different from 1 (FIG. 10B). The Ki values for HC-3, choline and ACh in inhibiting [$^3$H]HC-3 binding were 4 nM, 21CM and 433 µM, respectively.

Example 7

Transport Assaysfor hCHT

To assay CHT activity in resealed membrane vesicles from hCHT-transfected mammalian cells, the inventors transiently transfected COS-7 cells with hCHT as described herein above and prepared membrane fractions as described for binding assays. After obtaining the membrane fractions, resealed membrane vesicles were prepared as described by Fisher et al., 1992 (Fishe et al., 1992) with slight modifications. The membrane pellets were resuspended in 2 ml of HTE buffer (~2 µg/µl) and the suspension was rotated gently at 4° C. for 45 min. Membrane vesicle suspensions were centrifuged (27,000×g) for 20 min at 4° C. and the resulting pellet suspended in 2 ml of Na$^+$ and Cl$^-$ free HTE buffer. Protein content of the suspension was determined (Bradford; BioRad) and 50 µg of the vesicle suspension (1 µg/µl) was transferred to each tube for triplicate assays. [$^3$H]choline transport assays were initiated by the addition of [$^3$H]choline and NaCl diluted in HTE buffer to reach a final concentration of 20 nM and 150 mM, respectively. After a 5 min incubation at room temperature, vesicles were rapidly filtered through Whatman GF/B filters soaked in 0.3% polyethylenimine in HTE buffer and the accumulated radioactivity quantified as described for binding assays. In experiments designed to determine the ion-dependence of choline transport, Na$^+$ was replaced with equimolar concentrations of Li$^+$ and Cl$^-$ was replaced with equimolar concentrations of isethionate. In all experiments, non-specific uptake was quantified by determining uptake in the presence of 1 µM HC-3 and subtracted from the total uptake to yield specific transport.

Initial transport studies in cRNA-injected *Xenopus laevis* oocytes and intact, transfected COS-7 cells demonstrated a modest increase in [$^3$H]choline uptake, with activity too low to permit extensive kinetic or pharmacologic studies. We hypothesized that intracellular retention of CHTs in a cytoplasmic pool might be limiting choline transporter activity measurements with intact cells. Therefore, we determined CHT-mediated [$^3$H]choline transport using resealed membrane vesicles prepared from total cell membranes. In contrast to intact cell studies, we readily detected hCHT-mediated choline transport activity in resealed membrane-vesicles prepared from hCHT transfected COS-7 cells but not in vesicles prepared from vector transfected controls and addition of HC-3 reduced [$^3$H]choline uptake to levels seen in vector transfected COS-7 membrane vesicles (data not shown). The specific uptake of [$^3$H]choline is saturable and displays single-site kinetics (Hill coefficient n=0.99) with a Km of 1.6 µM (FIG. 10C). Replacement of either Na$^+$ with Li$^+$ or Cl$^-$ with isethionate reduced [$^3$H]choline uptake to levels seen in vector-transfected cells (data not shown). Unlabeled HC-3, choline and ACh inhibited [$^3$H]choline uptake in a dose-dependent fashion (FIG. 4D), yielding K$_i$ values of 5 nM, 123 nM, and 570 nM respectively.

Example 8

Transport Assays for mCHT

Figure 11:
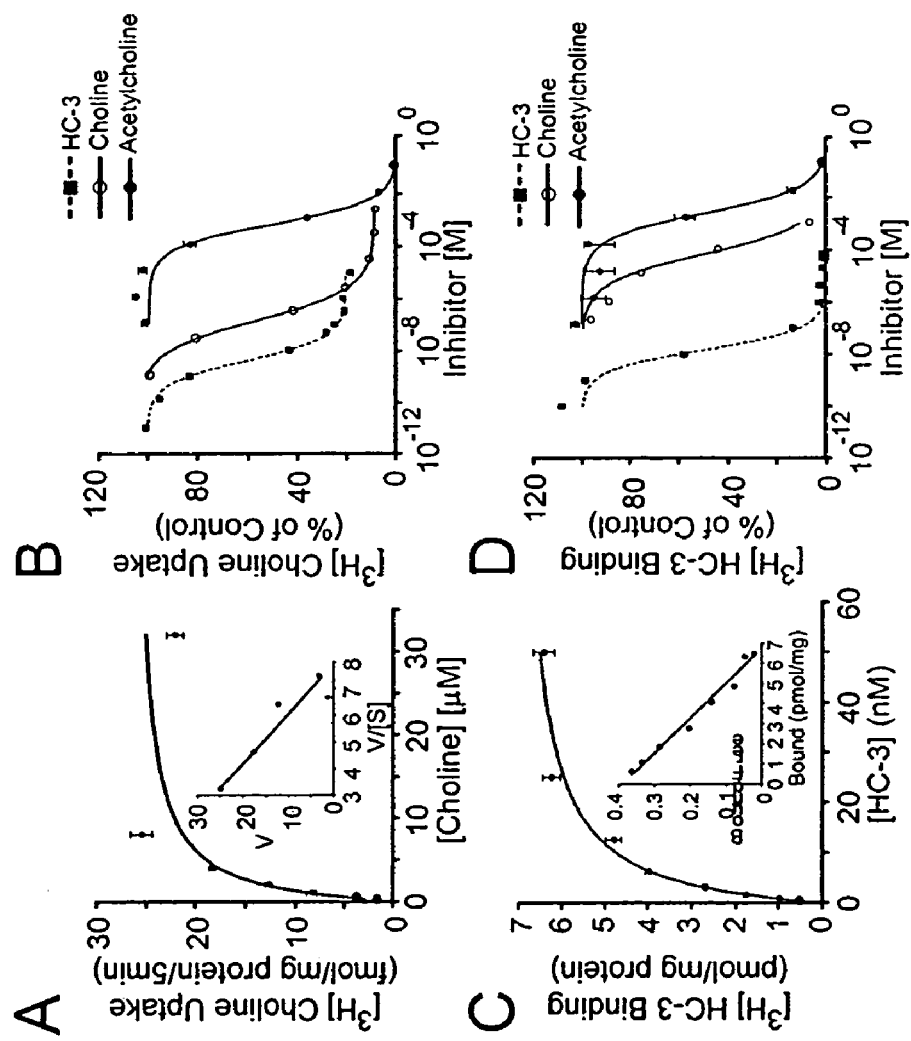
FIGS. 11A-11D—High-affinity choline uptake and hemicholinium-3 binding sites are evident following transient expression of mCHT in COS-7 cells. Resealed membrane vesicles obtained from mCHT transfected COS-7 cells exhibit saturable and high-affinity choline uptake. Insets are Eadie-Hofstee transformations of mCHT-mediated choline uptake in resealed membrane vesicles (FIG. 11A). Unlabeled HC-3, choline and ACh dose-dependently inhibit [$^3$H] choline uptake in resealed membrane vesicles of COS-7 cells (FIG. 11B). Unlabeled HC-3, choline and acetylcholine were co-incubated with labeled HC-3.

Initial transport studies in intact, transfected cells revealed that induced choline transport activity was too low to permit reliable kinetic analyses or pharmacological characterization. Similar to hCHT (Apparsundaram et al., 2000) functional mCHT protein is likely sequestered in non-trafficked, intracellular membranes. In order to access the intracellular pool of CHTs, CHT transport was evaluated in resealed membrane vesicles prepared from total cell membranes. Using this strategy, a specific accumulation of labeled choline that was absent from vesicles prepared from vector transfected COS-7 cells was readily detected. Furthermore, the presence of 1 µM HC-3 reduced choline uptake to levels seen in vector transfected COS-7 membrane vesicles. The specific uptake of labeled choline was found to be saturable and of high-affinity (FIG. 11A). The Eadie-Hofstee plot reveals the presence of a single-site for the specific uptake of choline with Km 2 µM. As with hCHT (Apparsundaram et al., 2000; Okuda et al., 2000), replacement of either Na$^+$ with Li$^+$ or Cl$^-$ with isoethionate reduced choline uptake to levels seen in vector-transfected cells. Co-application of unlabeled HC-3 and choline dose-dependently inhibited mCHT-mediated choline uptake (FIG B). The IC$_{50}$ for HC-3 and choline at mCHT were 5 nM and 123 nM, respectively. ACh in the presence of cholinesterase blockade also inhibited CHT-mediated choline uptake with an IC$_{50}$ of 570 µM.

The binding characteristics of the selective CHT antagonist HC-3 were also determined (Tamaru et al., 1988). As compared to vector-transfected cells, expression of mCHT cDNA in COS-7 cells produced a marked increase in [$^3$H] HC-3 binding in membrane fractions. Like choline transport, binding of [$^3$H] HC-3 was of high affinity and saturable (FIG. 6). Scatchard transformation of [$^3$H] HC-3 binding in mCHT expressing membranes indicated single site kinetics with an equilibrium dissociation constant (K$_d$) of 5 nM. Replacement of either Na$^+$ or Cl$^-$ with Li$^+$ or isoethionate reduced [$^3$H] HC-3 binding in mCHT expressing cells to levels seen in vector-transfected cells (data not shown). Unlabeled HC-3, choline and ACh (in the presence of physostigmine) dose-dependently inhibit [$^3$H] HC-3 binding in mCHT transfected COS-7 cell membrane. The $K_i$ values for HC-3, choline and ACh in inhibiting [$^3$H] HC-3 binding were 5 nM, 22 µM and 433 µM, respectively (FIG. 11D).

The cloning and functional expression studies as describe herein, along with the pattern of mRNA expression revealed in Northern hybridizations, suggest that mCHT encodes the protein that supports HACU in murine cholinergic neurons. The availability of mCHT and access to its genomic DNA should permit the generation of models useful for the study of high-affinity choline transport function and regulation in vitro and in vivo.

Example 9

Anti-ChT Antibody Generation

Polyclonal antibodies were raised in rabbits against the peptide of SEQ ID NO: 25 (VDSSPEGSGTEDNLQ, Research Genetics). This sequence corresponds to the COOH terminal 15 amino acids of the human, mouse, and rat choline transporters SEQ ID NOS: 2, 4 and 6 (Genbank Accession Numbers AF276871, AF276872, and AB030947 respectively). Antibodies were purified from the crude serum via affinity chromatography over an Affi-Gel 15 column (BioRad) to which was conjugated the immunizing peptide. Antibodies were eluted from the column in 0.15M glycine pH 2.5 and 1 ml fractions were collected and rapidly neutralized in 2M Tris (Sigma) pH 8.0. The fractions containing the peak absorbance at 280 nm were pooled and dialyzed overnight against PBS. Goat serum (Jackson ImmunoResearch Laboratories) was added to 10% (v/v) and aliquots were stored at −20° C. Antibodies were also effectively purified over an affinity column consisting of a GST fusion protein containing the hCHT COOH terminal 80 amino acids covalently attached to Reactigel beads (Pierce).

Example 10

Immunocytochemistry

Figure 12:
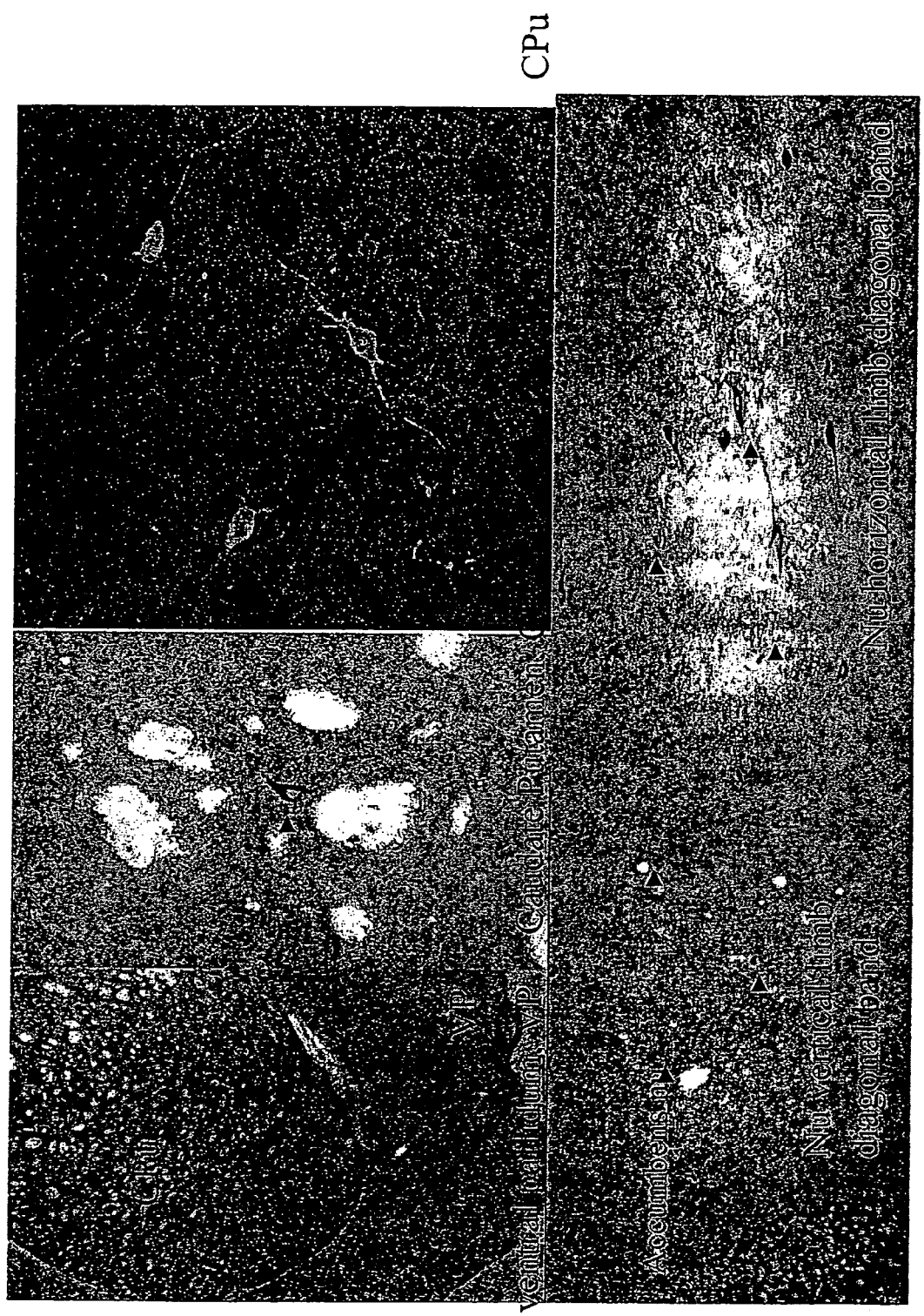
FIG. 12—Image of ChT-ir in striatum and basal ganglia. Immunocytochemistry with anti-peptide CHT antibody reveals staining of cholinergic neurons and terminals in the mouse striatum and basal forebrain FIG. 13—Image of ChT-ir in septum. Choline transporter antibodies stain cholinergic neurons and processes in the septal nucleus.
Figure 13:
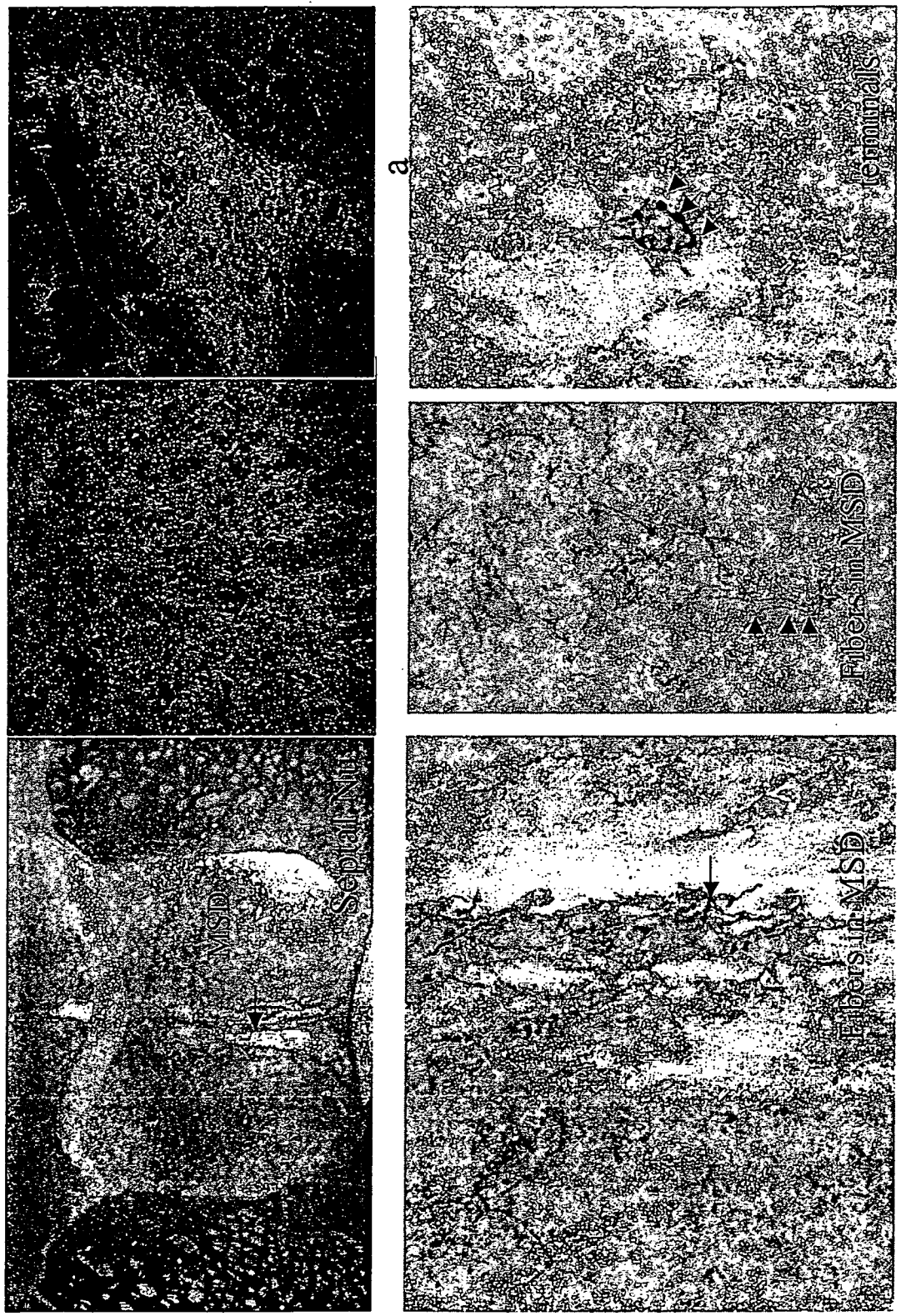
Figure 14:
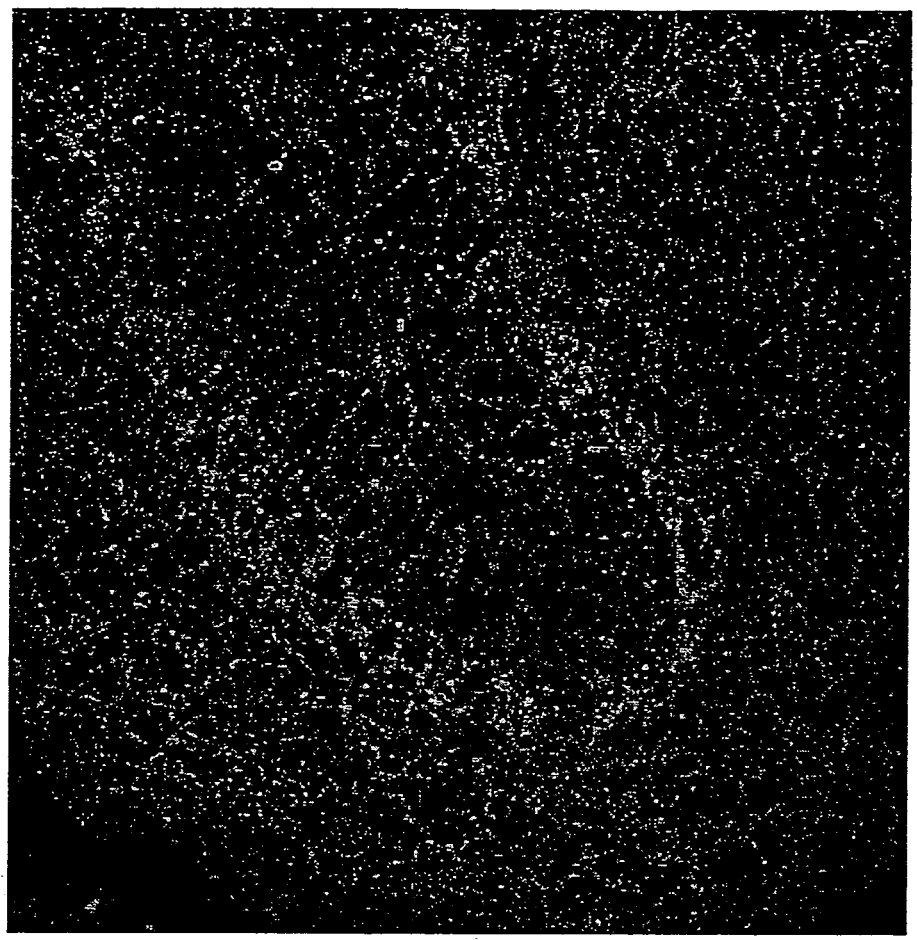
FIGS. 14A-B—Images of ChT-ir fibers in the hippocampus. Choline transporter antibodies reveal cholinergic fibers in the mouse hippocampus.
Figure 14:
Figure 14:
Figure 15:
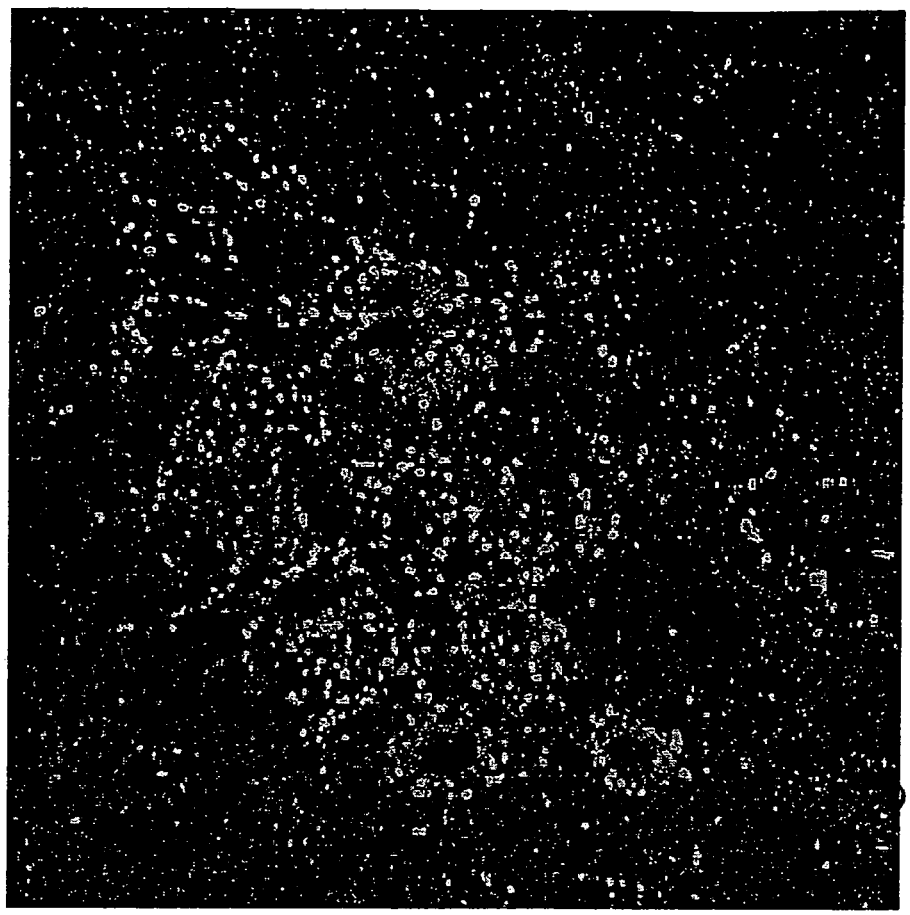
FIGS. 15A-15B—Image of ChT-ir fibers in the medulla oblongata (FIG. 15A) and a 3D confocal reconstruction (FIG. 15B). Choline transporter antibodies reveal staining of cholinergic motor neurons in the brainstem. Note the concentration of cholinergic synapses, revealed as dots, decorating cholinergic neurons.
Figure 15:
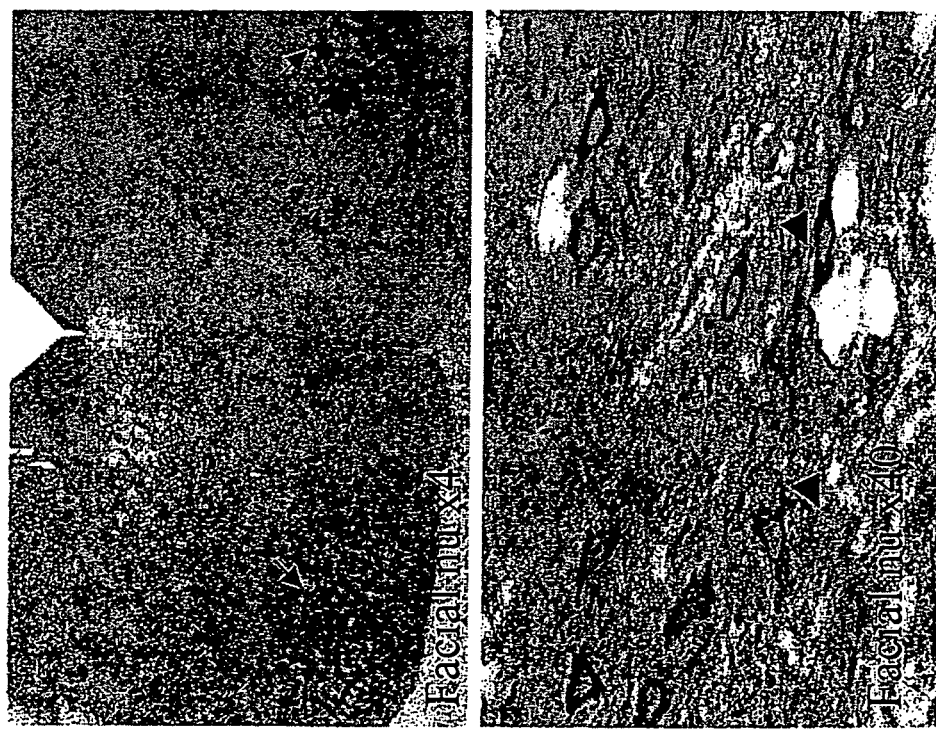
Figure 16:
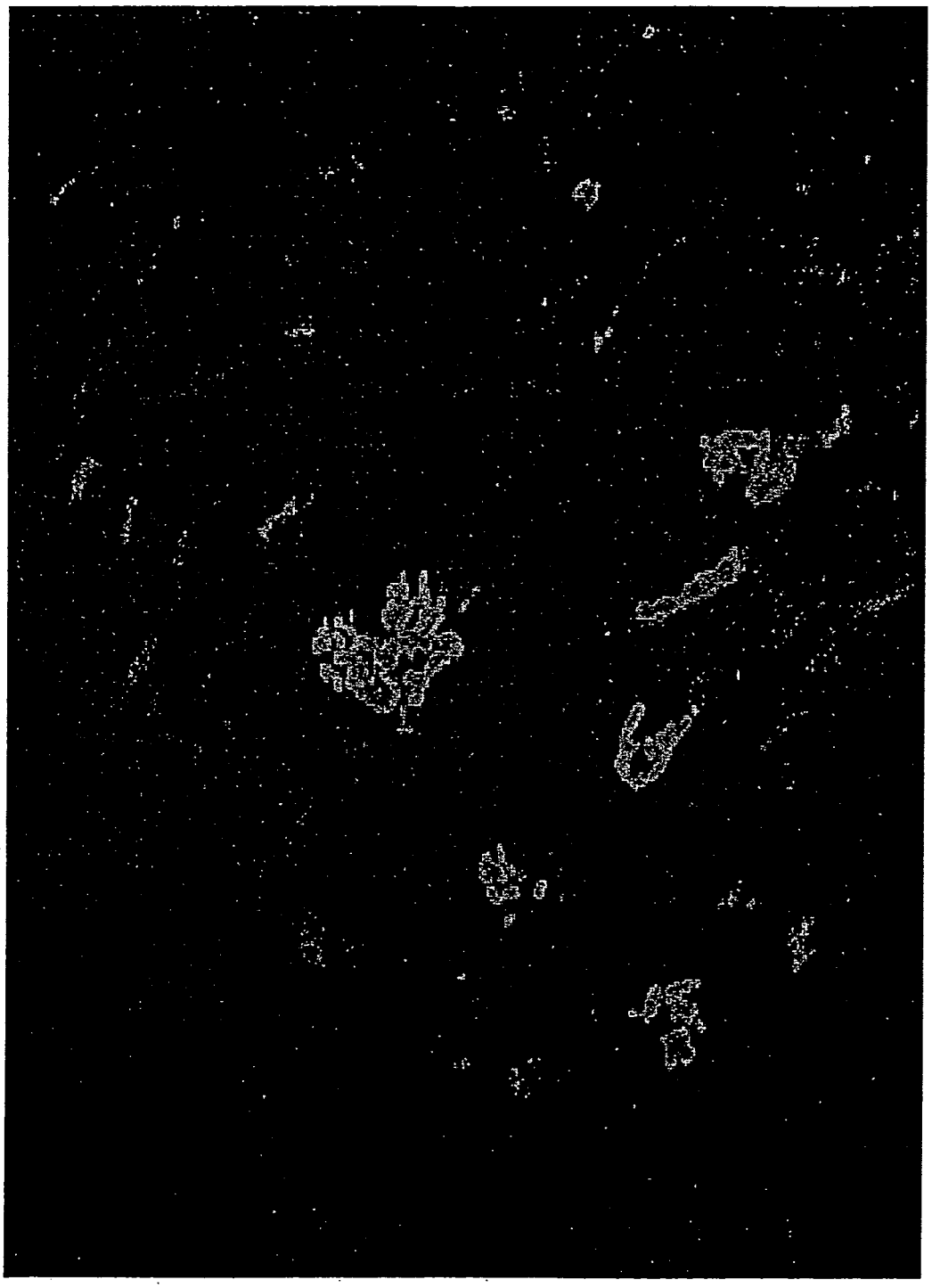
Figure 17:
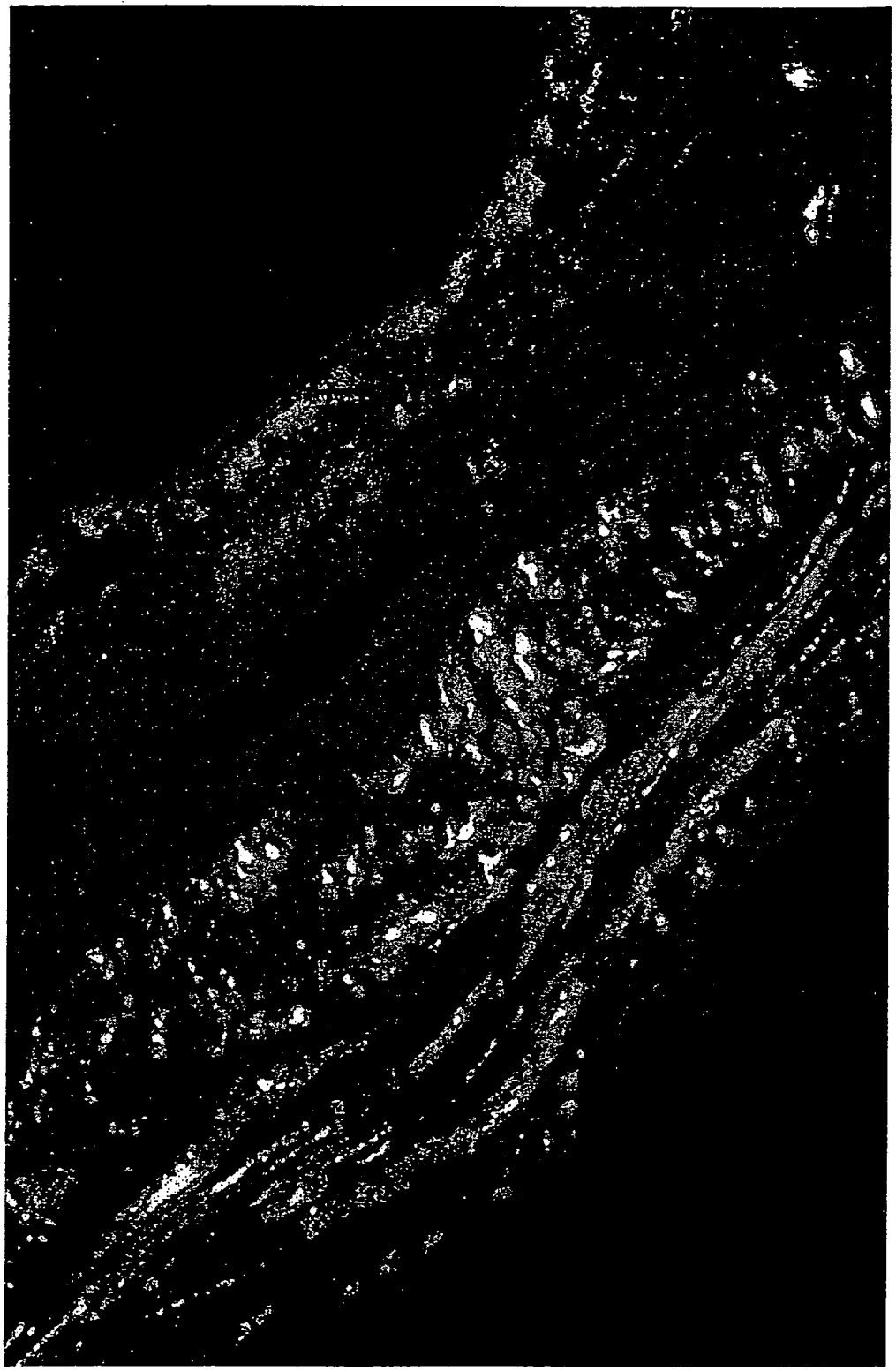

Immunocytochemistry reveal cholinergic neurons, terminals, fibers, synapses and other tissues associated with cholinergic function. Green fluorescent protein, or other visible markers can be used, suc a β-glacticidase (See, for example U.S. Pat. No. 6 894,205). Images of ChTt-ir in striatum and basal ganglia (FIG. 12), septum (FIG. 13), hipocampus. (FIG. 14), medulla oblongata (FIG. 15), neuromuscular junction of the diaphragm (FIG. 16) and the neuromuscular junction of the bladder (FIG. 17) demonstrate the use of immunocytochemistry for determining cholinerigic associated tissues. These images reveal the choline transporter antibodies stainging of cholinergic neurons and terminals in the mouse striatum and basal forebrain (FIG. 12) cholinergic neurons and processes in the septal nucleus (FIG. 13), cholinergic fibers in the mouse hippocampus (FIG. 14), cholinergic motor neurons in the brainstem (FIG. 15), cholinergic synapses on muscle cell (FIG. 16) and parasympathetic neuronal terminals on smooth muscle in the bladder.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Akil, H.; Watson, S. J.; Young, E.; Lewis, M. E.; Khachaturian, H. and Walker, J. M. Endogenous opioids: Biology and function. *Annual Review of Neuroscience* 1984, 7: 223-255.

Alvarez, E., Ferrer, T., Perez-Conde, C., Lopez-Terradas, J. M., Perez-Jimenez, A., and Ramos, M. J. (1996) Neuropediatrics 27:26-31.

Angel et al., Cell, 49:729, 1987b.

Angel et al., Mol. Cell. Biol., 7:2256, 1987a.

Antibodies: A Laboratory Manual, Cold Spring Harbor Laboratory, 1988

Apparsundaram, S., Ferguson, S., and Blakely, R. D. (2000) Soc Neurosci. Abstr. 26:15350.

Apparsundaram, S., Ferguson, S., and Blakely, R. D. (2001) Biochemical Society Transactions, in press.

Apparsundaram, S., Ferguson, S. M., George, A. L., Blakely R. D. "Molecular cloning of a human, hemicholinium-3-senstitive choline transporter" Biochem. Biophys. Research Comm. 276, 862-867, 2000.

Atchison and Perry, Cell, 48:121, 1987.

Attali et al., *J. Neurochem.* 52:360, 1989.

Atweh, S., Simon, J. R., and Kuhar, M. J. (1975) Life Sciences 17:1535-1544.

Avidor-Reiss, Nevo, Levy, Pfeuffer, Vogel, "Chronic opioid treatment induces adenylyl cyclase V superactivation," *Journal of Biological Chemistry,* 271:21309-21315, 1996.

Baichwal and Sugden, In: Gene Transfer, Kucherlapati R, ed., New York, Plenum Press, pp. 117-148, 1986.

Banerji et al., Cell, 27:299, 1981.

Banerji et al., Cell, 35:729, 1983.

Barnwell, J. F., Chaudhuri, G., Townsel, J. G. "Cloning and sequencing of a cDNA encoding a novel member of the human brain GABA/noradrenaline neurotransmitter transporter family" Gene 159, 287-288, 1995.

Baron, R., and Engler, F. (1996) J Neurol 243:18-24.

Benvenisty and Neshif, Proc. Nat. Acad. Sci. USA, 83:9551-9555, 1986.

Berkhout et al., Cell, 59:273, 1989.

Bero et al., *Mol. Pharmacol.,* 34:614, 1988.

Bertolucci et al., *Neurosci. Abstr.* 18L1368.

Berzal-Herranz et al., *Genes and DeveL,* 6:129-134, 1992.

Bierer, L. M., Haroutunian, V., Gabriel, S., Knott, P. J., Carlin, L. S., Purohit, D. P., Perl, D. P., Schmeidler, J., Kanof P., Davis, K. L., *J. Neurochem,* 64, 749-760, 1995.

Blanar et al., EMBO J., 8:1139, 1989.

Blusztajn, J. K. (1998) Science 281:794-5.

Bodine and Ley, EMBO J., 6:2997, 1987.

Bollag, D. M., Rozycki, M. D., and Edelstein, S. J. (1996). Protein Methods, Second Edition. New York: Wiley-Liss, 195-227.

Boshart et al., Cell, 41:521, 1985.

Bosze et al., EMBO J., 5:1615, 1986.

Bradbury et al., *Nature* 260:165, 1976.
Braddock et al., Cell, 58:269, 1989.
Breer, H., and Knipper, M. (1990) The Journal of Neurobiology 21:269-275.
Brogden, Speight, Avery, "Pentazocine: a review of its pharmacological properties, therapeutic efficacy and dependence liability," *Drugs,* 5:6-91, 1973.
Bulla and Siddiqui, J. Virol., 62:1437, 1986.
Calabresi, P., Centonze, D., Gubellini, P., Pisani, A., and Bernardi, G. (2000) Trends Neurosci 23:120-6.
Campbell and Villarreal, Mol. Cell. Biol., 8:1993, 1988.
Campere and Tilghman, Genes and Dev., 3:537, 1989.
Campo et al., Nature, 303:77, 1983.
Cancela, J. M., Bertrand, N., and Beley, A. (1995) Biochemical And Biophysical Research Communications 213:944-9.
Capaldi et al., *Biochem. Biophys. Res. Comm.,* 76:425, 1977.
Carter and Flotte, Ann. N.Y. Acad. Sci., 770:79-90, 1995.
Cech et al., "In vitro splicing of the ribosomal RNA precursor of Tetrahymena: involvement of a guanosine nucleotide in the excision of the intervening sequence," *Cell,* 27:487-496, 1981.
Celander and Haseltine, J. Virology, 61:269, 1987.
Celander et al., J. Virology, 62:1314, 1988.
Chandler et al., Cell, 33:489, 1983.
Chang et al., "Foreign gene delivery and expression in hepatocytes using a hepatitis B virus vector," *Hepatology,* 14:134 A, 1991.
Chang et al., Mol. Cell. Biol., 9:2153, 1989.
Chatterjee et al., *Proc. Natl. Acad. Sci. USA.,* 86:9114, 1989.
Chen and Okayama, Mol. Cell. Biol., 7:2745-2752, 1987.
Choi et al., Cell, 53:519, 1988.
Chowrira et al., "In vitro and in vivo comparison of hammerhead, hairpin, and hepatitis delta virus self-processing ribozyme cassetyes," *J. Biol. Chem.,* 269:25856-25864, 1994.
Chowrira et al., *Biochemistry,* 32:1088-1095, 1993.
Clark, Voulgaropoulou, Fraley, and Johnson, "Cell lines for the production of recombinant adeno-associated virus," *Human Gene Therapy,* 6:1329-1341, 1995.
Coffin, "Retroviridae and their replication," In: *Virology,* Fields et al (eds.), New York: Raven Press, pp. 1437-1500, 1990.
Coombs, Saunders, Lachance, Savage, Ragnarsson, Jensen, "Intrathecal morphine tolerance: Use of intrathecal clonidine, DADLE, and intraventricular morphine," *Anesthesiology,* 62: 358-363, 1985.
Costa et al., Mol. Cell. Biol., 8:81, 1988.
Cotecchia et al. *Proc. Natl. Acad. Sci. USA* 85:7159, 1988.
Couch et al., "Immunization with types 4 and 7 adenovirus by selective infection of the intestinal tract," *Am. Rev. Resp. Dis.,* 88:394-403, 1963.
Coupar et al., "A general method for the construction of recombinant vaccinia virus expressing multiple foreign genes," *Gene,* 68:1-10, 1988.
Coyle, J. T., Price, D. L., and DeLong, M. R. (1983) Science 219:1184-90.
Cripe et al., EMBO J., 6:3745, 1987.
Culotta and Hamer, Mol. Cell. Biol., 9:1376, 1989.
Dai, G., Levy, O., and Carrasco, N. (1996) Nature 379:458-459.
Dai, G., Levy, O., and Carrasco, N. (1996) Nature 379:458-60.
Dandolo et al., J. Virology, 47:55, 1983.
De Villiers et al., Nature, 312:242, 1984.
Deschamps et al., Science, 230:1174, 1985.
Di Chiara et al., *Trends Pharmacol. Sci.,* 13:185, 1992.
Dohlman, *Annu. Rev. Biochem.,* 60:166-170; 174-s176; 653-688, 1991.
Dohlman, *Biochemistry,* 26:2657, 1987.
Dubensky et al., Proc. Nat. Acad. Sci. USA, 81:7529-7533, 1984.
Duvoisin, Arch. Neurol., 17: 124, 1967
Edbrooke et al., Mol. Cell. Biol., 9:1908, 1989.
Edlund et al., Science, 230:912, 1985.
Elliott, Hynansky, Inturrisi, "Dextromethorphan attenuates and reverses analgesic tolerance to morphine," *Pain,* 59:361-368, 1994.
EPA 320,308
EPA 329,822
Erickson, J. D., Varoqui, H., Schafer, M. K. H., Modi, W., Diebler, M., Weihe, E., R and, J., Eiden, L. E., Bonner, T. I. and Usdin, T. B. (1994) The Journal of Biological Chemistry 269, 21929-21932
Fechheimer et al., *Proc. Natl. Acad. Sci. USA.* 84:8463-8467, 1987.
Feng and Holland, Nature, 334:6178, 1988.
Ferkol et al., FASEB J., 7:1081-1091, 1993.
Fibiger, H. C. (1991) Trends in Neuroscience 14:220-223.
Firak and Subramanian, Mol. Cell. Biol., 6:3667, 1986.
Fisher, A. B., Dodia, C., Chander, A., and Kleinzeller, A. (1992) Am J Physiol 263:C1250-7.
Flotte, Afione, Conrad, McGrath, Solow, Oka, Zeitlin, Guggino, and Carter, "Stable in vivo expression of the cystic fibrosis transmembrane conductance regulator with an adeno-associated virus vector," *Proc Natl. Acad. Sci. USA,* 90:10613-10617, 1993.
Foecking M K, Hofstetter H. *Gene.* 45(1):101-105, 1986.
Foley, "Opioid analgesics in clinical pain management. In: *Handbook of Experimental Pharmacology,* Herz, (Ed.), Vol. Vol. 104/II: Opioids II., Springer-Verlag, Berlin, pp. 693-743, 1993.
Forster and Symons, "Self-cleavage of plus and minus RNAs of a virusoid and a structural model for the active sites," *Cell,* 49:211-220, 1987.
Forster and Symons, "Self-cleavage of plus and minus RNAs of a virusoid and a structural model for the active sites," *Cell,* 49:211-220, 1987.
Fraley et al., *Proc. Natl. Acad. Sci. USA,* 76:3348-3352, 1979.
Friedmann, "Progress toward human gene therapy," *Science,* 244:1275-1281, 1989.
Frohman, *In: PCR Protocols: A Guide To Methods And Applications,* Academic Press, N.Y., 1990.
Fujita et al., Cell, 49:357, 1987.
GB 2202,328
Gerlach et al., "Construction of a plant disease resistance gene from the satellite RNA of tobacco rinspot virus," *Nature (London),* 328:802-805, 1987.
Ghosh and Bachhawat, In: Liver diseases, targeted diagnosis and therapy using specific receptors and ligands, (Wu G, Wu C ed.), New York: Marcel Dekker, pp. 87-104, 1991.
Ghosh-Choudhury et al., "Protein IX, a minor component of the human adenovirus capsid, is essential for the packaging of full-length genomes," *EMBO J,* 6:1733-1739, 1987.
Gilles et al., Cell, 33:717, 1983.
Gioannini et al., *J. Mol. Recogn.,* 2:44, 1989.
Gloss et al., EMBO J., 6:3735, 1987.
Godbout et al., Mol. Cell. Biol., 8:1169, 1988.
Gomez-Flores and Weber, "Differential effects of buprenorphine and morphine on immune and neuroendocrine functions following acute administration in the rat mesencephalon periaqueductal gray," *Immunopharm,m,* 48:145-156, 2000.

Gomez-Foix et al., "Adenovirus-mediated transfer of the muscle glycogen phosphorylase gene into hepatocytes confers altered regulation of glycogen," *J. Biol. Chem.,* 267:25129-25134, 1992.

Goodbourn and Maniatis, *Proc. Natl. Acad. Sci. USA,* 85:1447, 1988.

Goodbourn et al., Cell, 45:601, 1986.

Gopal, Mol. Cell. Biol., 5:1188-1190, 1985.

Graham and Prevec, "Adenovirus-based expression vectors and recombinant vaccines," *Biotechnology,* 20:363-390, 1992.

Graham and Prevec, "Manipulation of adenovirus vectors," In. Gene Transfer and Expression Protocols, Murray, E. J., ed., Humana, New Jersey, vol. 7, 109-128, 1991.

Graham and Van Der Eb, Virology, 52:456-467, 1973.

Gramsch et al., *J. Biol. Chem.,* 263:5853, 1988.

Gramsch et al., *J. Biol. Chem.,* 263:5853, 1988.

Greene et al., Immunology Today, 10:272, 1989.

Grosschedl and Baltimore, Cell, 41:885, 1985.

Grunhaus and Horwitz, "Adenovirus as cloning vector," *Seminar in Virology,* 3:237-252, 1992.

Guimbal, C., and Kilimann, M. W. (1993) *J Biol Chem* 268:8418-21.

Guyenet, P., Lefresne, P., Rossier, J., Beaujouan, J. C., and Glowinski, J. (1973) Mol Pharmacol 9:630-9.

Harlow, E. and Lane, D. (1988). Antibodies: A Laboratory Manual. Cold Spring Harbor, N.Y.: Cold Spring Harbor Laboratory Press, 471-510.

Haseloff and Gerlach, "Simple RNA enzymes with new and highly specific endoribonuclease activities," *Nature,* 334: 585-591, 1988.

Haslinger and Karin, *Proc. Natl. Acad. Sci.* USA., 82:8572, 1985.

Hauber and Cullen, J. Virology, 62:673, 1988.

Hediger, M. A., Coady, M. J., Ikeda, T. S., and Wright, E. M. (1987) Nature 330:379-81.

Hen et al., Nature, 321:249, 1986.

Hensel et al., Lymphokine Res., 8:347, 1989.

Hermonat and Muzyczka, "Use of adeno-associated virus as a mammalian DNA cloning vector; transduction of neomycin resistance into mammalian tissue culture cells," *Proc Nat'l. Acad. Sci. USA,* 81:6466-6470, 1984.

Herr and Clarke, Cell, 45:461, 1986.

Hersdorffer et al., "Efficient gene transfer in live mice using a unique retroviral packaging line," *DNA Cell Biol.,* 9:713-723, 1990.

Herz and Gerard, "Adenovirus-mediated transfer of low density lipoprotein receptor gene acutely accelerates cholesterol clearance in normal mice," *Proc. Nat'l. Acad. Sci. USA* 90:2812-2816, f993.

Hirochika et al., J. Virol., 61:2599, 1987.

Hirsch et al., Mol. Cell. Biol., 10: 1959, 1990.

Holbrook et al., Virology, 157:211, 1987.

Horlick and Benfield, Mol. Cell. Biol., 9:2396, 1989.

Horwich et al. "Synthesis of hepadenovirus particles that contain replication-defective duck hepatitis B virus genomes in cultured HuH7 cells," *J. Virol.,* 64:642-650, 1990.

Hsia et al. *J. Biol. Chem.,* 259:1086, 1984.

Huang et al., Cell, 27:245, 1981.

Hughes, J.; Smith, T. W.; Kosterlitz, H.; Fothrgill, L.; Morgan, B. and Morris, H. Identification of two related pentapeptides from the brain with potent opiate agonist activity. *Nature* 1975, 258: 577-579.

Hwang et al., Mol. Cell. Biol., 10:585, 1990.

Imagawa et al., Cell, 51:251, 1987.

Imbra and Karin, Nature, 323:555, 1986.

Imler et al., Mol. Cell. Biol., 7:2558, 1987.

Imperiale and Nevins, Mol. Cell. Biol., 4:875, 1984.

Jakobovits et al., Mol. Cell. Biol., 8:2555, 1988.

Jameel and Siddiqui, Mol. Cell. Biol., 6:710, 1986.

Jaynes et al., Mol. Cell. Biol., 8:62, 1988.

Ji, R.-R., Baba, H., et al. (1999) Nature Neuroscience 2, 1114-9.

Johnson et al., Mol. Cell. Biol., 9:3393, 1989.

Jones and Shenk, "Isolation of deletion and substitution mutants of adenovirus type 5," *Cell,* 13:181-188, 1978.

Joyce, "RNA evolution and the origins of life," *Nature,* 338:217-244, 1989.

Kadesch and Berg, Mol. Cell. Biol., 6:2593, 1986.

Kaeppler et al., *Plant Cell Reports* 9: 415-418, 1990.

Kaneda et al., Science, 243:375-378, 1989.

Kanner, B. I. and Schuldiner, S. CRC Crit, rev. Biochem. 22, 1-38. 1987.

Karin et al., Mol. Cell. Biol., 7:606, 1987.

Karlin, et al., 1986

Karlsson et al., *EMBO J.,* 5:2377-2385, 1986.

Kasahara et al., *Science,* 266: 1373-1376, 1994.

Kase et al., A potent inhibitor of protein kinase C from microbial origin," *J. Antibiot.,* (8):1059-1065, 1986

Katinka et al., Cell, 20:393, 1980.

Katinka et al., Nature, 290:720, 1981.

Kato et al., J. Biol. Chem., 266:3361-3364, 1991.

Kato, A. C., Touzeau, G., Bertrand, D., and Bader, C. R. (1985) J Neurosci 5:2750-61.

Kawamoto et al., Mol. Cell. Biol., 8:267, 1988.

Kiledjian et al., Mol. Cell. Biol., 8:145, 1988.

Kim and Cech, "Three dimensional model of the active site of the self-splicing rRNA precursor of Tetrahymena," *Proc. Natl. Acad. Sci. USA,* 84:8788-8792, 1987.

Klamut et al., Mol. Cell. Biol., 10: 193, 1990.

Klein et al., Nature, 327:70-73, 1987.

Knipper, M., Boekhoff, I., and Breer, H. (1989) Federation of Experimental Biological Sciences 245:235-237.

Knipper, M., Kahle, C., and Breer, H. (1991) Biochimica et Biophysica Acta 1065:107-113.

Kobilka et al. *J. Biol. Chem.,* 262:7321, 1987.

Koch et al., Mol. Cell. Biol., 9:303, 1989.

Kolesnikov, Pick, Ciszewska, Pasternak, "Blockade of tolerance to morphine but not kappa opioids by a nitric oxide synthase inhibitor," *Proc. Natl Acad. Sci. USA.,* 90:5162-5166, 1993.

Kotin, Siniscalco, Samulski, Zhu, Hunter, McLaughlin, Muzyczka, and Berns, "Site-specific integration by adeno-associated virus," *Proc Nail Acad. Sci. USA,* 87:2211-2215, 1990.

Kriegler and Botchan, In: Eukaryotic Viral Vectors, Y. Gluzman, ed., Cold Spring Harbor: Cold Spring Harbor Laboratory, NY, 1982.

Kriegler and Botchan, Mol. Cell. Biol., 3:325, 1983.

Kriegler et al., Cell, 38:483, 1984a.

Kriegler et al., Cell, 53:45, 1988.

Kriegler et al., In: Cancer Cells 2/Oncogenes and Viral Genes, Van de Woude et al., eds, Cold Spring Harbor, Cold Spring Harbor Laboratory, 1984b.

Kriegler et al., In: Gene Expression, D. Hamer and M. Rosenberg, eds., New York: Alan R. Liss, 1983.

Kuhl et al., Cell, 50:1057, 1987.

Kunz et al., Nucl. Acids Res., 17:1121, 1989.

Kyte, J., and Doolittle, R. F. (1982) J Mol Biol 157:105-32.

LaFace, Hermonat, Wakeland, and Peck, "Gene transfer into hematopoietic progenitor cells mediated by an adeno-associated virus vector," *Viology*, 162:483-486, 1988.

Lange, K. W., Javoy-Agid, F., Agid, Y., Jenner, P., and Marsden, C. D. (1992) J Neurol 239:103-4.

Larsen et al., *Proc. Natl. Acad. Sci. USA.*, 83:8283, 1986.

Laspia et al., Cell, 59:283, 1989.

Latimer et al., Mol. Cell. Biol., 10:760, 1990.

Laughlin, Cardellichio, and Coon, "Latent infection of kb cells with adeno-associated virus type 2," *J. Virol*, 60:515-524, 1986.

Le Gal La Salle et al., "An adenovirus vector for gene transfer into neurons and glia in the brain," *Science*, 259:988-990, 1993.

Lebkowski, McNally, Okarma, and Lerch, "Adeno-associated virus: a vector system for efficient introduction and integration of DNA into a variety of mammalian cell types," *Mol. Cell. Biol.*, 8:3988-3996, 1988.

Lee et al., Nature, 294:228, 1981.

Lee, Tomasetto, Sager, *Proc. Natl. Acad. Sci. USA*, 88:2825, 1991.

Levinson et al., Nature, 295:79, 1982.

Levrero et al., "Defective and nondefective adenovirus vectors for expressing foreign genes in vitro and in vivo," *Gene*, 101: 195-202, 1991.

Levy, O., De la Vieja, A., Ginter, C. S., Riedel, C., Dai, G., and Carrasco, N. (1998) J Biol Chem 273:22657-63.

Lieber and Strauss, "Selection of efficient cleavage sites in target RNAs by using a ribozyme expression library." *Mol. Cell. Biol.*, 15: 540-551, 1995.

Lin et al., Mol. Cell. Biol., 10:850, 1990.

Loh et al., *Annu. Rev. Pharmacol. Toxicol.*, 30:123, 1990.

Lomasney et al., *Proc. Natl. Acad. Sci. USA*, 87:5094, 1990.

Luo, Zhou, Cooper, Munshi, Boswell, Broxmeyer, and Srivastava, "Adeno-associated virus 2 mediated transfer and functional expression of a gene encoding the human granulocyte-macrophage colony-stimulating factor," *Blood*,82 (Supp.):1,303A, 1994.

Luria et al., EMBO J., 6:3307, 1987.

Lusky and Botchan, *Proc. Natl. Acad. Sci. USA.*, 83:3609, 1986.

Lusky et al., Mol. Cell. Biol., 3:1108, 1983.

Lutz et al., J. Receptor Res., 12:267, 1992.

Majors and Varmus, *Proc. Natl. Acad. Sci. USA.*, 80:5866, 1983.

Mann et al., "Mammalian protein serine/threonine phosphatase 2C: cDNA cloning and comparative analysis of amino acid sequences," *Biochim. Biophys. Acta*, 1130: 100-104, 1992.

Markowitz et al., "A safe packaging line for gene transfer: Separating viral genes on two different plasmids," *J. Virol*, 62:1120-1124, 1988.

Mayser, W., Schloss, P. Betz, H. "Primary structure and functional expression of a choline transporter expressed in the rat nervous system" FEBS, 305(1), 31-36, 1992.

Mayser, W., Schloss, P., and Betz, H. (1992) Febs Letters 305:31-6.

McCarthy M P, Earnest J P, Young E F, Choe S, Stroud R M. "The molecular neurobiology of the acetylcholine receptor" (1986) Annu Rev Neurosci. 9:383-413.

McCarty, Christensen, and Muzyczka, "Sequences Required for Coordinate Induction of Adeno-Associated Virus p19 and p40 Promoters by Rep Protein," *J. Virol*, 65:2936-2945, 1991.

McLaughlin, Collis, Hermonat, and Muzyczka, "Adeno-Associated Virus General Transduction Vectors Analysis of Proviral Structures," *J. Virol.*, 62:1963-1973, 1988.

McNeall et al., Gene, 76:81, 1989.

Mestek, Hurley, Bye, Campell, Chen, Tian, Liu, Schulman, Yu, "The human 1 opiod receptor: modulation of function desensitizatiion by calcium/calmodulin-dependent protein kinase and protein kinase," C. *Neuroscience*, 15:2396-2406, 1995.

Mesulam, M. M., Mash, D., Hersh, L., Bothwell, M., and Geula, C. (1992) J Comp Neurol 323:252-68.

Michel and Westhof, "Modeling of the three-dimensional architecture of group I catalytic introns based on comparative sequence analysis," *J. Mol. Biol.*, 216:585-610, 1990.

Miksicek et al., Cell, 46:203, 1986.

Miller, *Curr. Top. Microbiol. Immunol.*, 158:1, 1992.

Miyomoto and Takemore, "Inhibition of naloxone-precipitated withdrawal jumping by i.c.v. and i.t. administration of saline in morphine-dependent mice," *Life Sci.*, 52(13): 1129-1134, 1993b.

Miyomoto and Takemore, "Relative involvement of supraspinal and spinal mu opioid receptors in morphine dependence in mice," *Life Sci.*, 52(12):1039-1044, 1993a.

Mizukawa, K., McGeer, P. L., Tago, H., Peng, J. H., McGeer, E. G., and Kimura, H. (1986) Brain Res 379: 39-55.

Mordacq and Linzer, Genes and Dev., 3:760, 1989.

Moreau et al., Nucl. Acids Res., 9:6047, 1981.

Muesing et al., Cell, 48:691, 1987.

Murrin, L. C., DeHaven, R. N., and Kuhar, M. J. (1977) The Journal of Neurochemistry 29:681-687.

Muzyczka, "Use of Adeno-Associated Virus as a General Transduction Vector for Mammalian Cells," *Curr. Top. Microbiol. Immunol.*, 158:97-129, 1992.

Naciff, J. M., Misawa, H. and Dedman, J. R. (1997) Neuroreport 8, 3467-73.

Narita, Nartia, Mizoguchi, Tseng, "Inhibition of Protein Kinase C, but not of Protein Kinase A, blocks the development of acute antinociceptive tolerance to an intrathecally administered µ-opioid receptor agonist in the mouse," *European Pharmacology*, 280:R1-R3, 1995.

Nathans et al., *Science*, 232:193, 1986a.

Nathans et al., *Science*, 232:203, 1986b.

Ng et al., Nuc. Acids Res., 17:601, 1989.

Nicolas and Rubinstein, "Retroviral vectors," *In: Vectors: A survey of molecular cloning vectors and their uses*, Rodriguez and Denhardt (eds.), Stoneham: Butterworth, 494-513, 1988.

Nicolau and Sene, Biochim. Biophys. Acta, 721:185-190, 1982.

Nicolau et al., Methods Enzymol., 149:157-176, 1987.

Nielsen, H., Engelbrecht, J., Brunak, S., and von Heijne, G. (1997) Protein Eng 10:1-6.

Nikawa, J., Hosaka, K., Tsukagoshi, Y., Yamashita, S. "Primar structure of the yeast choline transport gene and regulation of its expression" J. Biolog. Chem. 265(26) 15996-16003, 1990.

Nothwang, H. G., Rensing, C., Kubler, M., Denich, D., Brandl, B., Stubanus, M., Haaf, T., Kurnit, D., and Hildebrandt, F. (1998) Genomics 47:383-92.

Ohi, Dixit, Tillery, and Plonk, "Construction and replication of an adeno-associated virus expression vector that contains human lambda.-globin cDNA," *Gene*, 89L:279-282, 1990.

Okuda, T, Haga, T., Kanai, Y., Endou, H., Ishihara, T., Katsura, I. "Identification and characterization of the high-affinity choline transporter" *Nature Neuroscience* 3(2) 2000.

Okuda, T., Haga, T., Kanai, Y., Endou, H., Ishihara, T., and Katsura, I. (2000) Nat Neurosci 3:120-5.

Olson et al., *Peptides,* 10: 1253, 1988.

Omirulleh et al., "Activity of a chimeric promoter with the doubled CaMV 35S enhancer element in protoplast-derived cells and transgenic plants in maize," *Plant Mol. Biol.,* 21:415-28, 1993.

Ondek et al., EMBO J., 6:1017, 1987.

O'Regan, S., Traiffort, E., Ruat, M., Cha, N., Compaore, D., and Meunier, F. M. (2000) Proc Natl Acad Sci USA 97:1835-40.

Ornitz et al., Mol. Cell. Biol., 7:3466, 1987.

Palmiter et al., Nature, 300:611, 1982.

Palukaitis et al., "Characterization of a viroid associated with avacado sunblotch disease," *Virology,* 99:145-151, 1979.

Pascual, J., Gonzalez, A. M., and Pazos, A. (1990) J Neurochem 54:792-800.

Paskind et al., "Dependence of moloney murine leukemia virus production on cell growth," *Virology,* 67:242-248, 1975.

PCT Application No. US87/00880

PCT Application No. US89/01025

Pech et al., Mol. Cell. Biol., 9:396, 1989.

Pei, Kieffer, Lefkowitz, Freedman, "Agonist-dependent phosphorylation of the mouse□ α-opiod receptor: Involvement of G protein-coupled receptor kinases but not protein kinase C," *Molecular Pharmacology,* 48:173-177, 1995.

Perales et al., *Proc. Natl. Acad. Sci.* 91:40864090, 1994.

Perez-Stable and Constantini, Mol. Cell. Biol., 10: 1116, 1990.

Perriman et al., "Extended target-site specificity for a hammerhead ribozyme," *Gene,* 113:157-163, 1992.

Pert and Snyder, "Opiate receptor; demonstration in nervous tissue," *Science,* 179:1011-1014, 1973.

Pfeiffer, Brantl, Herz, Emrich, "Psychotomimesis mediated by kappa opiate receptors," *Science,* 233:774-776, 1986.

Picard and Schaffner, Nature, 307:83, 1984.

Pick, Roques, Gacel, Pasternak, "Supraspinal $mu_2$ receptors mediate spinal/supraspinal morphine synergy," *Eur. J. Pharmacol,* 220:275-277, 1992a.

Pinkert et al., Genes and Dev., 1:268, 1987.

Ponta et al., *Proc. Natl. Acad. Sci.* USA., 82:1020, 1985.

Porton et al., Mol. Cell. Biol., 10: 1076, 1990.

Potrykus et al., *Mol. Gen. Genet.,* 199:183-188, 1985.

Potter et al., Proc. Nat. Acad. Sci. USA, 81:7161-7165, 1984.

Prody et al., "Autolytic processing of dimeric plant virus satellite RNA." *Science,* 231:1577-1580, 1986.

Puttfarcken et al., *Mol. Pharmacol,* 33:520, 1988.

Queen and Baltimore, Cell, 35:741, 1983.

Quinn et al., Mol. Cell. Biol., 9:4713, 1989.

Racher et al., *Biotechnology Techniques,* 9:169-174, 1995.

Radler et al., Science, 275:810-814, 1997.

Ragot et al., "Efficient adenovirus-mediated transfer of a human minidystrophin gene to skeletal muscle of mdx mice," *Nature,* 361:647-650, 1993.

Redondo et al., Science, 247:1225, 1990.

Regan et al., *Proc. Natl. Acad. Sci. USA,* 85:6301, 1988.

Reinhold-Hurek and Shub, "Self-splicing introns in tRNA genes of widely divergent bacteria," *Nature,* 357:173-176, 1992.

Reisman and Rotter, Mol. Cell. Biol., 9:3571, 1989.

Remington's Pharmaceutical Sciences, 18th Ed. Mack Printing Company, 1990.

Resendez Jr. et al., Mol. Cell. Biol., 8:4579, 1988.

Ridgeway, "Mammalian expression vectors," *In: Vectors: A survey of molecular cloning vectors and their uses.* Rodriguez and Denhardt, eds. Stoneham: Butterworth, pp. 467-492, 1988.

Ripe et al., Mol. Cell. Biol., 9:2224, 1989.

Rippe et al., Mol. Cell. Biol., 10:689-695, 1990.

Rittling et al., Nucl. Acids Res., 17:1619, 1989.

Rodriguez-Puertas, R., Pazos, A., and Pascual, J. (1994) Brain Res 636:327-32.

Rosen et al., Cell, 41:813, 1988.

Rosenfeld, Siegfried, Yoshimura, Yoneyama, Fukayama, Stier, Paakko, Gilardi, Stratford-Perricaudet, Perricaudet, Jallat, Pavirani, Lecocq, Crystal, "Adenovirus-mediated transfer of a recombinant alpha. 1-antitrypsin gene to the lung epithelium in vivo," *Science,* 252:431-434, 1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, "In vivo transfer of the human cystic fibrosis transmembrane conductance regulator gene to the airway epithelium," *Cell,* 68:143-155, 1992.

Rossi, Pasternak, Bodnar, "Synergistic brainstem interactons for morphine analgesia," *Brain Res.,* 624: 171-180, 1993.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA,* 86:9079-9083, 1989.

Rylett, R. J. (1988) The Journal of Neurochemistry 51:1942-1945.

Rylett, R. J., Ball, M. J., and Colhoun, E. H. (1983) Brain Res 289:169-75.

Rylett, R. J., Walters, S. A., and Davis, W. (1996) Brain Research. Molecular Brain Research 35:354-8.

Sakai et al., Genes and Dev., 2:1144, 1988.

Saltarelli M D, Bauman A L, Moore K R, Bradley C C, Blakely R D. "Expression of the rat brain creatine transporter in situ and in transfected HeLa cells." Dev Neurosci. 1996; 18(5-6):524-34.

Sambrook, Fritsch, Maniatis, In: Molecular Cloning: A Laboratory Manual 2 rev.ed., Cold Spring Harbor: Cold Spring Harbor Laboratory Press, 1989.

Sarver et al., "Ribozymes as potential anti-HIV-1 therapeutic agents," *Science,* 247:1222-1225, 1990.

Satake et al., J. Virology, 62:970, 1988.

Scanlon et al., "Ribozyme-mediated cleavages of c-fos mRNA reduce gene expression of DNA synthesis enzymes and metallothionein," *Proc Natl Acad Sci USA,* 88:10591-10595, 1991.

Schaffner et al., J. Mol. Biol., 201:81, 1988.

Schloss, P., Mayser, W., and Betz, H. (1994) Biochem Biophys Res Commun 198:637-45.

Schnider and Levinson, *Anesthesia for Obsterics,* Williams & Wilkins, Baltimore, 566 pp, 1987.

Searle et al., Mol. Cell. Biol., 5:1480, 1985.

Sharma, Klee, Nirenberg, "Opiate-dependent modution of adenylate cyclase,". *Proc. Natl. Acad. Sci. U.S.A.,* 74:3365-3369, 1977.

Sharp and Marciniak, Cell, 59:229, 1989.

Sharp and Yaksh, "Pain killers of the immune system," *Nature Medicine,* 3:831-832, 1997.

Shaul and Ben-Levy, EMBO J., 6:1913, 1987.

Shelling and Smith, *Gene Therapy,* 1: 165-169, 1994.

Sherman et al., Mol. Cell. Biol., 9:50, 1989.

Simon, J. R., and Kuhar, M. G. (1975) Nature 255:162-3.
Simon, *Medicinal Res. Rev.,* 11:357, 1991.
Sioud et al., "Preformed ribozyme destroys tumour necrosis factor mRNA in human cells," *J Mol. Biol,* 223:831-835, 1992.
Sleigh and Lockett, J. EMBO, 4:3831, 1985.
Spalholz et al., Cell, 42:183, 1985.
Spandau and Lee, J. Virology, 62:427, 1988.
Spandidos and Wilkie, EMBO J., 2:1193, 1983.
Stephens and Hentschel, Biochem. J., 248:1, 1987.
Stewart, E. A., et al. (1997) Genome Res 7:422-33.
Stratford-Perricaudet and Perricaudet., *In: Human Gene Transfer,* Eds, Cohen-Haguenauer and Boiron, Editions John Libbey Eurotext, France, pp. 51-61, 1991a.
Stratford-Perricaudet et al., *Hum. Gene. Ther.* 1:241-256, 1991b.
Strotchman and Simon (1991).
Stuart et al., Nature, 317:828, 1985.
Sullivan and Peterlin, Mol. Cell. Biol., 7:3315, 1987.
Swartzendruber and Lehman, J. Cell. Physiology, 85:179, 1975.
Symons, "Avacado sunblotch viroid: primary sequence and proposed secondary structure." *Nucl. Acids Res.,* 9:6527-6537, 1981.
Symons, "Small catalytic RNAs." *Annu. Rev. Biochem.,* 61:641-671, 1992.
Takebe et al., Mol. Cell. Biol., 8:466, 1988.
Tamaru, M. and Roberts, E. (1988) Brain Research 473, 205-26.
Tandon, R. (1999) Br J Psychiatry Suppl 37:7-11.
Tavernier et al., Nature, 301:634, 1983.
Taylor and Kingston, Mol. Cell. Biol., 10:165, 1990a.
Taylor and Kingston, Mol. Cell. Biol., 10:176, 1990b.
Taylor et al., J. Biol. Chem., 264:15160, 1989.
Taylor, in Goodman and Gilman's The Pharmacological Basis of Therapeutics, 18th Ed., Gilman et al., eds., Pergamon Press, pp. 166-186 (1990).
Temin, "Retrovirus vectors for gene transfer: Efficient integration into and expression of exogenous DNA in vertebrate cell genome," *In: Gene Transfer,* Kucherlapati (ed.), New York: Plenum Press, pp. 149-188, 1986.
Thiesen et al., J. Virology, 62:614, 1988.
Thompson et al., "Ribozymes in gene therapy." *Nature Medicine,* 1:277-278, 1995.
Top et al., "Immunization with live types 7 and 4 adenovirus vaccines. II. Antibody response and protective effect against acute respiratory disease due to adenovirus type 7," *J. Infect. Dis.,* 124:155-160, 1971.
Tratschin, Miller, Smith, and Carter, "Adeno-associated virus vector for high-frequency integration, expression and rescue of genes in mammalian cells," *Mol. Cell. Biol.,* 5:3258-3260, 1985.
Tronche et al., Mol. Biol. Med., 7:173, 1990.
Tronche et al., Mol. Cell. Biol., 9:4759, 1989.
Trudel and Constantini, Genes and Dev., 6:954, 1987.
Turk, E., and Wright, E. M. (1997) J Membr Biol 159:1-20.
Tur-Kaspa et al., Mol. Cell. Biol., 6:716-718, 1986.
Tyndall et al., Nuc. Acids. Res., 9:6231, 1981.
U.S. Pat. No. 4,682,195
U.S. Pat. No. 4,683,195
U.S. Pat. No. 4,683,202
U.S. Pat. No. 4,684,611
U.S. Pat. No. 4,797,368
U.S. Pat. No. 4,800,159
U.S. Pat. No. 4,883,750
U.S. Pat. No. 4,946,773
U.S. Pat. No. 4,952,500
U.S. Pat. No. 5,082,592
U.S. Pat. No. 5,139,941
U.S. Pat. No. 5,175,166
U.S. Pat. No. 5,279,721
U.S. Pat. No. 5,302,523
U.S. Pat. No. 5,322,783
U.S. Pat. No. 5,354,855
U.S. Pat. No. 5,384,253
U.S. Pat. No. 5,403,845
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,618,818
U.S. Pat. No. 5,656,610
U.S. Pat. No. 5,670,488
U.S. Pat. No. 5,672,344
U.S. Pat. No. 5,702,932
U.S. Pat. No. 5,726,179
U.S. Pat. No. 5,736,524
U.S. Pat. No. 5,780,448
U.S. Pat. No. 5,789,215
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 6,046,173
U.S. Pat. No. 6,096,767
U.S. Pat. No. 6,136,550
U.S. Pat. No. 6,177,451
Ueda, Miyamae, Hayashi, Watanabe, Fukushima, Sasaki, Iwamura, Misu, "Protein kinase C involvement in homologous desensitization of α-opioid receptor coupled to Gil-phosoholipase C activation in xenopus oocytes," *Journal of Neuroscience,* 15:7485-7499, 1995.
Vannice and Levinson, J. Virology, 62:1305, 1988.
Vasseur et al., *Proc. Natl. Acad. Sci. USA.,* 77:1068, 1980.
Vogelsberg, V., Neff, N. H., and Hadjiconstantinou, M. (1997) J. Neurochem. 68:1062-1070.
von Heijne, G. (1992) J Mol Biol 225:487-94.
Wagner et al., *Proc. Natl. Acad. Sci.* 87(9):3410-3414, 1990.
Wagner et al., Science, 260:1510-1513, 1993.
Walsh, Nienhuis, Samulski, Brown, Miller, Young, and Liu, *J. Clin. Invest,* 94:1440-1448, 1994.
Wang and Calame, Cell, 47:241, 1986.
Wang, Johnson, Persico, Hawkins, Griffin, Uhl, "Human a opiate receptor: cDNA and genomic clones, pharmacologic characterization and chromosomal assignment," *FEBS Letters,* 338: 217-222, 1994.
Wang, Y., Cao, Z., Newkirk, R. F., Ivy, M. T. and Townsel, J. G. (2001) Gene 268, 123-31.
Watt et al., Proc. Natl. Acad. Sci., 83(2): 3166-3170, 1986.
Weber et al., Cell, 36:983, 1984.
Weinberger et al., Mol. Cell. Biol., 8:988, 1984.
Whistler, J. and vonZastrow, M. (1998) *Proc. Natl. Acad. Sci.* 95, 9914-9.
Winoto and Baltimore, Cell, 59:649, 1989.
WO 88/10315
WO 89/06700
WO 90/07641

WO 94/09699
WO 95/06128
Wong et al., Gene, 10:87-94, 1980.
Wu and Wu, Adv. Drug Delivery Rev., 12:159-167, 1993.
Wu and Wu, Biochem., 27:887-892, 1988.
Wu and Wu, J. Biol. Chem., 262:4429-4432, 1987.
Xie et al., *Proc. Natl. Acad. Sci* USA, 89:4124, 1992.
Yamada, K., Saltarelli, M. D., and Coyle, J. T. (1991) Brain Research 542:132-134.
Yamamura, H. I., and Snyder, S. H. (1972) Science 178: 626-8.
Yang et al., *Proc. Natl. Acad Sci* USA, 87:9568-9572, 1990.
Yang, Chen, Trempe, "Characterization of cell lines that inducibly express the adeno-associated virus Rep proteins," *J. Virol,* 68:4847-4856, 1994.
Yuan and Altman, "Selection of guide sequences that direct efficient cleavage of mRNA by human ribonuclease P," *Science,* 263:1269-1273, 1994.
Yuan et al., "Targeted cleavage of mRNA by human RNase P," *Proc. Natl. Acad. Sci. USA,* 89:8006-8010, 1992.

Yutzey et al., Mol. Cell. Biol., 9:1397, 1989.
Zheng C F. Guan K L. (1993) Cloning and characterization of two distinct human extracellular signal-regulated kinase activator kinases, MEK1 and MEK2. J. Biol. Chem. 268, 11435-11439.
Zhou et al., *Plant Cell Reports,* 12(11).612-616, 1993.
Zoli, M., Guidolin, D., Agnati, L. F. (1992) "Morphometric evaluation of populations of neuronal profiles (cell bodies, dendrites and nerve terminals) in the central nervous system." Microsc. Res. Tech., 21, 315-337.
Zoli, M; Lena, C., Picciotto, M. R., Changeux, J.-P. (1998) "Identification of four classes of brain nicotinic receptors using P2-mutant mice." J. Neuroscie, 18, 44614472.
Zoli, M; Picciotto, M. R.; Ferrari, R. Cocchi, D, Changeux, J. P. "Increased neurodegeneration during ageing in mice lacking high-affinity nicotine receptors" EMBO Journal 18:5 1235-1244, 1999.

What is claimed is:

1. An isolated polynucleotide encoding a polypeptide comprising the amino acid sequence as set forth in SEQ ID NO: 4.

2. The isolated polynucleotide of claim 1, wherein said polynucleotide comprises the nucleic acid sequence as set forth in SEQ ID NO:3.

3. The polynucleotide of claim 2, wherein said polynucleotide is operatively linked to a promoter.

4. The polynucleotide of claim 2, further defined as a cDNA segment.

5. The polynucleotide of claim 2, wherein said polynucleotide is in a vector.

6. An isolated recombinant host cell comprising a DNA segment encoding a murine choline transporter having the amino acid sequence as set forth in SEQ ID NO:4 wherein the DNA segment is under the control of a heterologous promoter.

7. A recombinant vector comprising a DNA segment encoding a mouse choline transporter polypeptide having the sequence of SEQ ID NO:4 under the control of a promoter.

* * * * *

UNITED STATES PATENT AND TRADEMARK OFFICE
CERTIFICATE OF CORRECTION

PATENT NO. : 7,338,799 B2  
APPLICATION NO. : 10/724806  
DATED : March 4, 2008  
INVENTOR(S) : Randy D. Blakely et al.

Page 1 of 1

It is certified that error appears in the above-identified patent and that said Letters Patent is hereby corrected as shown below:

In column 1, line 15, please delete "may have" and insert --has-- therefor.

In claim 7, column 164, line 50, please insert --wherein the DNA segment is-- after "SEQ ID NO:4".

In claim 7, column 164, line 50, please insert --heterologous-- after "control of a".

Signed and Sealed this

Tenth Day of June, 2008

JON W. DUDAS  
*Director of the United States Patent and Trademark Office*